(12) United States Patent
Meyer et al.

(10) Patent No.: US 12,171,688 B2
(45) Date of Patent: Dec. 24, 2024

(54) OCULAR CANNULA GUIDE

(71) Applicant: Genentech, Inc., South San Francisco, CA (US)

(72) Inventors: Thomas E. Meyer, Philadelphia, PA (US); Mark Hedgeland, Norristown, PA (US); Benjamin Ko, Cincinnati, OH (US); Thomas Gernetzke, Cincinnati, OH (US); Olivia Enneking, Cincinnati, OH (US); Eric Kennedy, Cincinnati, OH (US); Robert Roth, Cincinnati, OH (US); Michael Auld, Cincinnati, OH (US); Jacob Schubert, Cincinnati, OH (US); Samuel Ridgley, Cincinnati, OH (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 18/268,749

(22) PCT Filed: Dec. 15, 2021

(86) PCT No.: PCT/IB2021/000864
§ 371 (c)(1),
(2) Date: Jun. 21, 2023

(87) PCT Pub. No.: WO2022/136913
PCT Pub. Date: Jun. 30, 2022

(65) Prior Publication Data
US 2023/0390111 A1    Dec. 7, 2023

Related U.S. Application Data

(60) Provisional application No. 63/128,936, filed on Dec. 22, 2020.

(51) Int. Cl.
*A61F 9/00* (2006.01)
*A61B 17/34* (2006.01)

(52) U.S. Cl.
CPC .... *A61F 9/0017* (2013.01); *A61B 2017/3405* (2013.01); *A61B 2017/3454* (2013.01)

(58) Field of Classification Search
CPC .... A61F 9/0017; A61F 9/0008; A61F 9/0026; A61F 9/00736; A61F 9/00781;
(Continued)

(56) References Cited

U.S. PATENT DOCUMENTS

| 7,413,734 B2 | 8/2008 | Mistry et al. |
| 10,226,379 B2 | 3/2019 | Oberkircher et al. |

(Continued)

FOREIGN PATENT DOCUMENTS

| WO | WO 2015/102963 A2 | 7/2015 |
| WO | WO 2016/196841 A1 | 12/2016 |

OTHER PUBLICATIONS

International Search Report and Written Opinion dated May 6, 2022, for International Application No. PCT/IB2021/000864, 10 pages.

*Primary Examiner* — Scott J Medway
*Assistant Examiner* — Anh Bui
(74) *Attorney, Agent, or Firm* — Frost Brown Todd LLP

(57) ABSTRACT

An apparatus includes a body, and anchoring feature, and a guide feature. The body is sized and configured to be positioned on an eye of a patient. The anchoring feature is configured to secure the body to the eye of the patient. The guide feature is configured to guide a cannula into a scleral incision formed in the eye of the patient along a path that is substantially tangential relative to the eye of the patient. The (Continued)

guide feature is sized and configured to allow the cannula to pivot laterally through a range of angular motion at the scleral incision.

19 Claims, 51 Drawing Sheets

(58) Field of Classification Search
CPC ............ A61F 9/007; A61B 2017/3405; A61B 2017/3454; A61M 2210/0612; A61M 2005/1416; A61M 2005/1585
See application file for complete search history.

(56) References Cited

U.S. PATENT DOCUMENTS

| | | |
|---|---|---|
| 10,478,553 B2 | 11/2019 | Meyer et al. |
| 10,646,374 B2 | 5/2020 | Price et al. |
| 2013/0168432 A1* | 7/2013 | Vold ................ A61B 17/105 227/175.1 |
| 2013/0296893 A1* | 11/2013 | Dean ............... A61B 17/06166 606/228 |
| 2015/0223977 A1* | 8/2015 | Oberkircher .......... A61F 9/0017 604/521 |
| 2016/0354244 A1* | 12/2016 | Horvath ............... A61F 9/0017 |
| 2017/0360605 A1* | 12/2017 | Oberkircher .......... A61F 9/0026 |
| 2017/0360606 A1 | 12/2017 | Price et al. |
| 2018/0256394 A1 | 9/2018 | Price et al. |

* cited by examiner

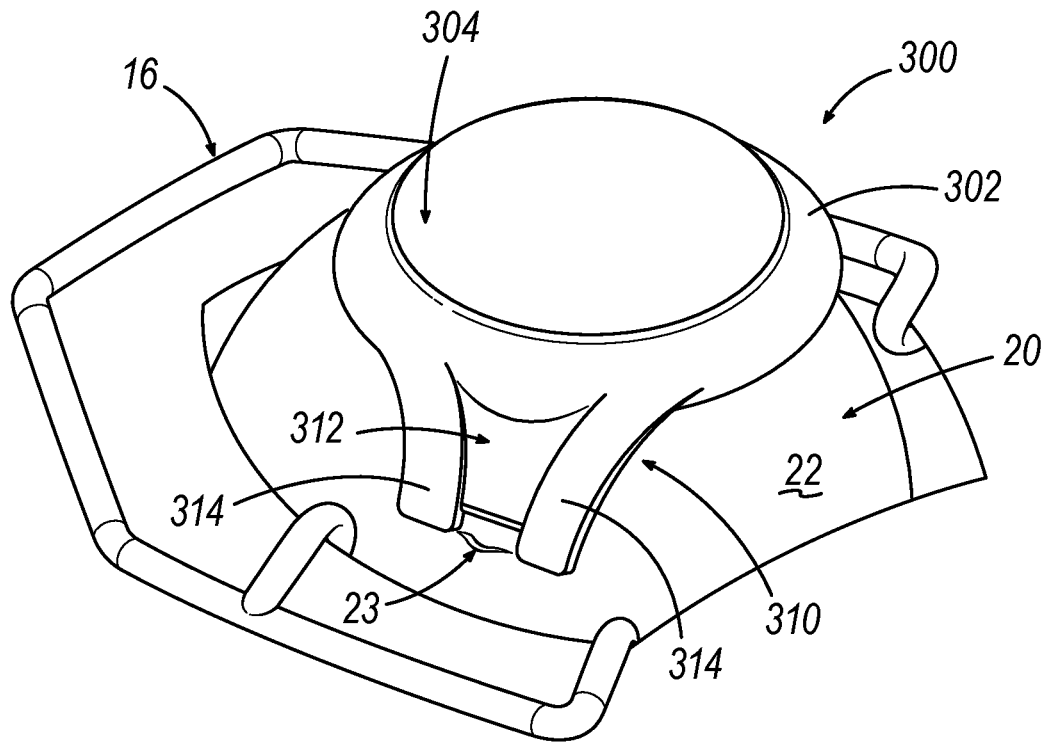
FIG. 9
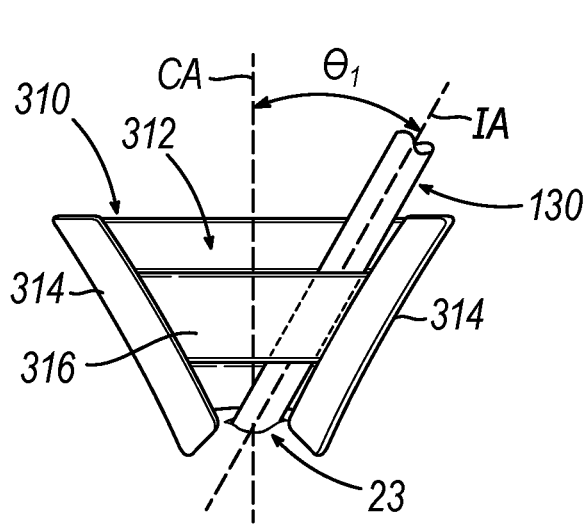 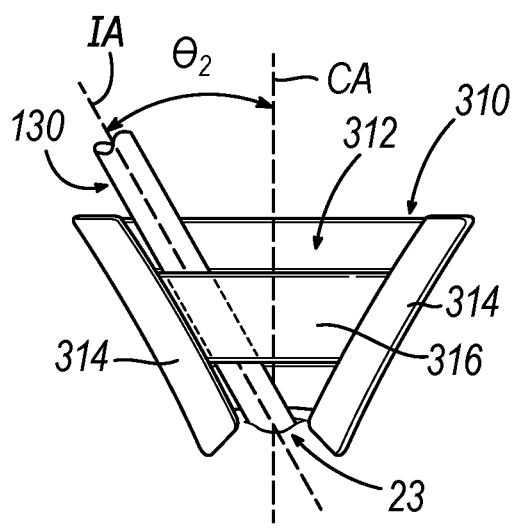
FIG. 10A  FIG. 10B

OCULAR CANNULA GUIDE

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and, in some cases, may disappear as well. It may therefore be desirable to provide treatment for macular degeneration to prevent or reverse the loss of vision caused by macular degeneration. In some cases, it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9 depicts a perspective view of an example of a cannula guide that may be secured to an eye of a patient;

FIG. 10A depicts a plan view of a cannula inserted into an eye of a patient via the cannula guide of FIG. 9, with the cannula positioned at a first angular orientation;

FIG. 10B depicts a plan view of a cannula inserted into an eye of a patient via the cannula guide of FIG. 9, with the cannula positioned at a second angular orientation;

Figure 1:
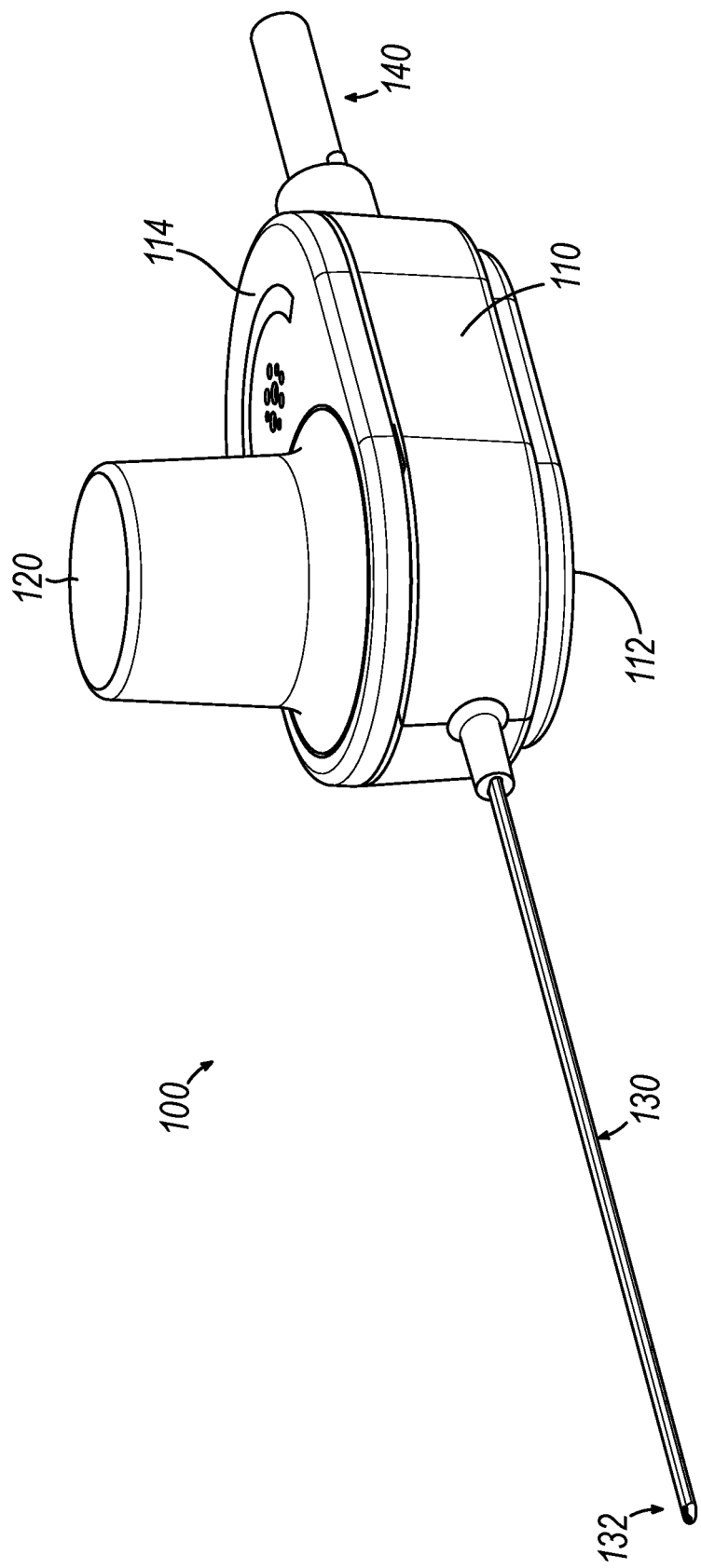
FIG. 1 depicts a perspective view of an example of an instrument for subretinal administration of a therapeutic agent from a suprachoroidal approach.
Figure 2:
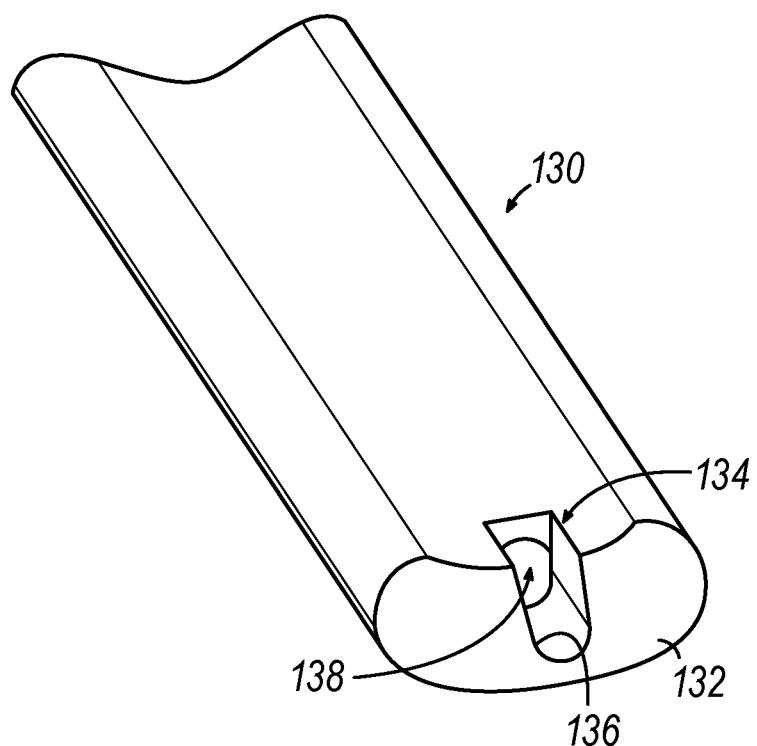
FIG. 2 depicts a perspective view of a distal portion of a cannula of the instrument of FIG. 1.
Figure 3:
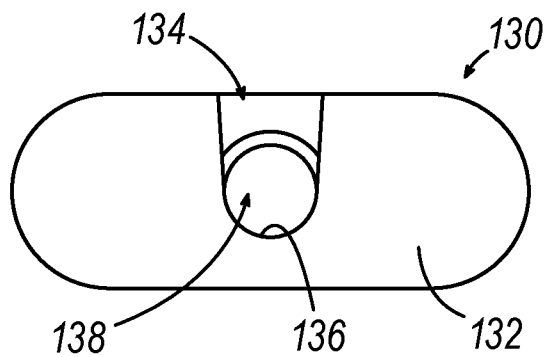
FIG. 3 depicts a front elevation view of the distal portion of the cannula of FIG. 2.
Figure 4:
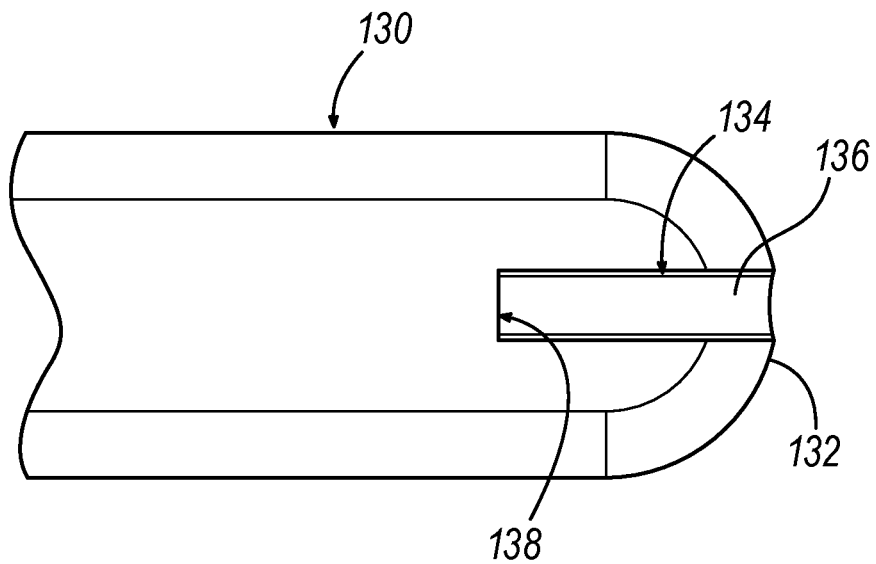
FIG. 4 depicts a top plan view of the distal portion of the cannula of FIG. 2.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. INSTRUMENT FOR SUBRETINAL ADMINISTRATION OF THERAPEUTIC AGENT

FIG. 1 shows an example of an instrument (100) that is configured for use in a procedure for the subretinal administration of a therapeutic agent to an eye of a patient from a suprachoroidal approach. Instrument (100) comprises a body (110) and a flexible cannula (130) extending distally from body (110). Cannula (130) of the present example has a generally rectangular cross section, though any other suitable cross-sectional profile (e.g., elliptical, etc.) may be used. The generally rectangular cross-sectional profile of cannula (130) is configured to enable cannula (130) to be passed atraumatically along the suprachoroidal space, as will be described in greater detail below. Cannula (130) is generally configured to support a needle (150) that is slidable within cannula (130), as will be described in greater detail below.

In the present example, cannula (130) comprises a flexible material such as Polyether block amide (PEBA), though any other suitable material or combination of materials may be used. In some versions, cannula (130) has a cross-sectional profile dimension of approximately 1.6 mm (width) by approximately 0.6 mm (height), with a length of approximately 80 mm. Alternatively, any other suitable dimensions may be used. Cannula (130) of the present example is flexible enough to conform to specific structures and contours of the patient's eye, yet cannula (130) has sufficient column strength to permit advancement of cannula (130) between the sclera and choroid of patient's eye without buckling. As best seen in FIGS. 2-5, cannula (130) includes a transversely oriented opening (134) near the distal end (132) of cannula (130). Opening (134) of the present example is formed by a U-shaped lateral recess (136) in cannula (130), which leads to an open distal end (138) of a needle guide lumen within cannula (130). Distal end (132) is atraumatic such that distal end (132) is configured to provide separation between the sclera and choroid layers via blunt dissection, as will be described in greater detail below, to thereby enable cannula (130) to be advanced between such layers while not inflicting trauma to the sclera or choroid layers.

By way of example only, cannula (130) may be configured and operable in accordance with at least some of the teachings of U.S. Pat. No. 10,226,379, entitled "Method and Apparatus for Subretinal Administration of Therapeutic Agent," issued Mar. 12, 2019, the disclosure of which is incorporated by reference herein; U.S. Pat. No. 10,646,374, entitled "Apparatus and Method to From Entry Bleb for Subretinal Delivery of Therapeutic Agent," issued May 12, 2020, the disclosure of which is incorporated by reference herein; and/or in any other suitable fashion.

Figure 5:
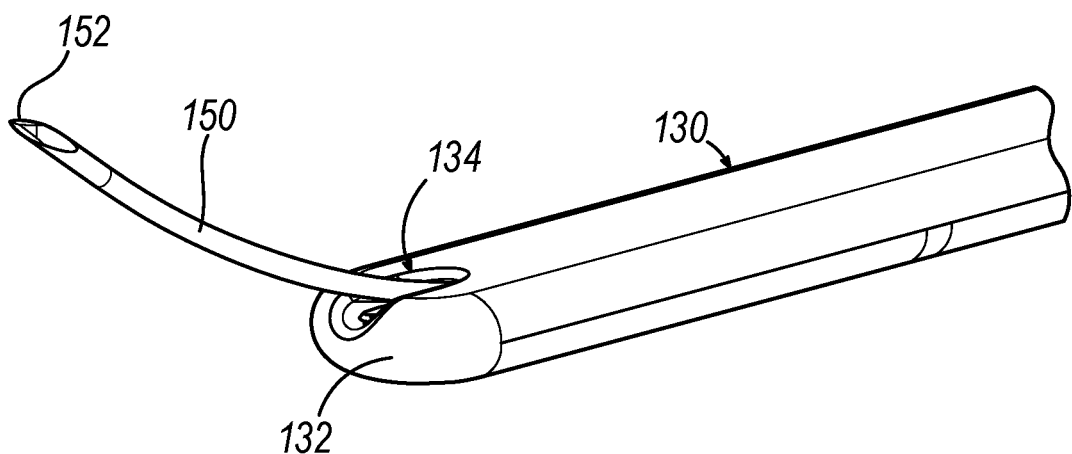
FIG. 5 depicts a perspective view of the distal end of a cannula of FIG. 2, with a needle extending from the cannula.

As shown in FIG. 5, needle (150) may be advanced distally to protrude from opening (134). Needle (150) of the present example has a sharp distal tip (152) and defines a lumen (not shown). Distal tip (152) of the present example has a lancet configuration. In some other versions, distal tip (152) has a tri-bevel configuration or any other configuration as described in U.S. Pat. No. 10,226,379, the disclosure of which is incorporated by reference herein. Still other suitable forms that distal tip (152) may take will be apparent to those skilled in the art in view of the teachings herein. In the present example, the generally rectangular, generally elliptical, or otherwise generally flat cross-sectional profile of cannula (130) prevents cannula (130) from rotating about the longitudinal axis of cannula (130) when cannula (130) is disposed in the suprachoroidal space as will be described in greater detail below. This provides a consistent and predictable orientation of opening (134), thereby providing a consistent and predictable exit path for needle (150) when needle (150) is advanced distally relative to cannula (130) as will be described in greater detail below.

By way of example only, the angle defined between the exposed portion of needle (150) and cannula (130), after needle (150) has been advanced distally relative to cannula (130), may be within the range of approximately 5° to approximately 30° relative to the longitudinal axis of cannula (130); or more particularly within the range of approximately 5° to approximately 20° relative to the longitudinal axis of cannula (130); or more particularly within the range of approximately 5° to approximately 10° relative to the longitudinal axis of cannula (130); or more particularly within the range of approximately 7° and approximately 9° relative to the longitudinal axis of cannula (130). In the present example, needle (150) is resiliently biased to assume a bent configuration to thereby provide an exit angle that varies based on the extent to which needle (130) is advanced distally relative to cannula (130). By way of further example only, needle (150) may include a preformed bend in accordance with at least some of the teachings of U.S. Pat. No. 10,478,553, entitled "Apparatus for Subretinal Administration of Therapeutic Agent via a Curved Needle," issued Nov. 19, 2019, the disclosure of which is incorporated by reference herein.

As shown in FIG. 1, instrument (100) of the present example further comprises an actuation knob (120) located at a top portion (114) of body (110). Actuation knob (120) is rotatable relative to body (110) to thereby selectively translate needle (150) longitudinally relative to cannula (130). In particular, actuation knob (120) is rotatable in a first angular direction to drive needle (150) distally relative to cannula (130); and in a second angular direction to drive needle (150) proximally relative to cannula (130). By way of example only, instrument (100) may provide such functionality through knob (120) in accordance with at least some of the teachings of U.S. Pat. No. 10,646,374, the disclosure of which is incorporated by reference herein. Other suitable ways in which rotary motion of knob (120) may be converted to linear translation of needle (150) will be apparent to those skilled in the art in view of the teachings herein. Similarly, other suitable ways in which needle (150) may be actuated (150) longitudinally relative to cannula (130) will be apparent to those skilled in the art in view of the teachings herein. As also shown in FIG. 1, a conduit assembly (140) extends proximally from body (110). Conduit assembly (140) is configured to contain one or more fluid conduits (not shown) that are in fluid communication with needle (150). In some versions such fluid conduits are coupled with sources of leading bleb fluid and therapeutic agent.

II. PROCEDURE FOR INDUCING SEPARATION BETWEEN RETINA AND CHOROID TO ENHANCE DELIVERY OF A THERAPEUTIC AGENT

As described in U.S. Pat. No. 10,226,379, it may be desirable to inject a therapeutic agent into the subretinal space of an eye (20) to treat macular degeneration or some other condition. By way of example only, the therapeutic agent may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. While treatment of macular degeneration is an example provided herein, instrument (100) and the methods described herein are not intended to necessarily be limited to treatment of the particular medical conditions that are specifically identified herein. A non-exhaustive, non-limiting listing of other conditions that may be addressed by instrument (100) and the examples of methods described herein may include diabetic macular edema, inherited retinal diseases, retinitis pigmentosa, retinal vein occlusion, diabetic retinopathy, posterior uveitis, Stargardt disease, etc.

In the procedures described in U.S. Pat. No. 10,226,379, a relatively small volume of a leading bleb fluid (e.g., balanced salt solution or "BSS") is injected into the subretinal space to provide a barrier between distal tip (152) of needle (150) and the retina (26), to thereby reduce the risk of the retina being inadvertently pierced by distal tip (152). In these procedures, the relatively small volume (e.g., approximately 50 μL) of leading bleb fluid provides a highly localized separation of the retina from the choroid. A relatively small volume (e.g., approximately 50 μL) of therapeutic agent is then delivered to this same region of sub-retinal space, mixing with the leading bleb fluid. As the therapeutic agent is delivered to the subretinal space, the additional volume may provide some degree of additional separation of the retina from the choroid, though this separation may still be substantially localized and only apply to a relatively small region of the retina. The therapeutic agent is primarily absorbed by the relatively small region of the retina that was separated from the choroid by the leading bleb fluid and the therapeutic agent.

In some scenarios, it may be desirable to enhance the absorption of the therapeutic agent by increasing the surface area of the retina that is directly exposed to the therapeutic agent. This may be carried out by providing additional, intentional separation of the retina from the choroid. As described in U.S. Pub. No. 2018/0256394, entitled "Method of Performing Subretinal Drainage and Agent Delivery," published Sep. 13, 2018, the disclosure of which is incorporated by reference herein, a substantial region of the retina may be intentionally separated from the choroid by injecting a substantial volume of leading bleb fluid to the subretinal space. Another merely illustrative example of such a procedure is described in greater detail below.

Figure 6:
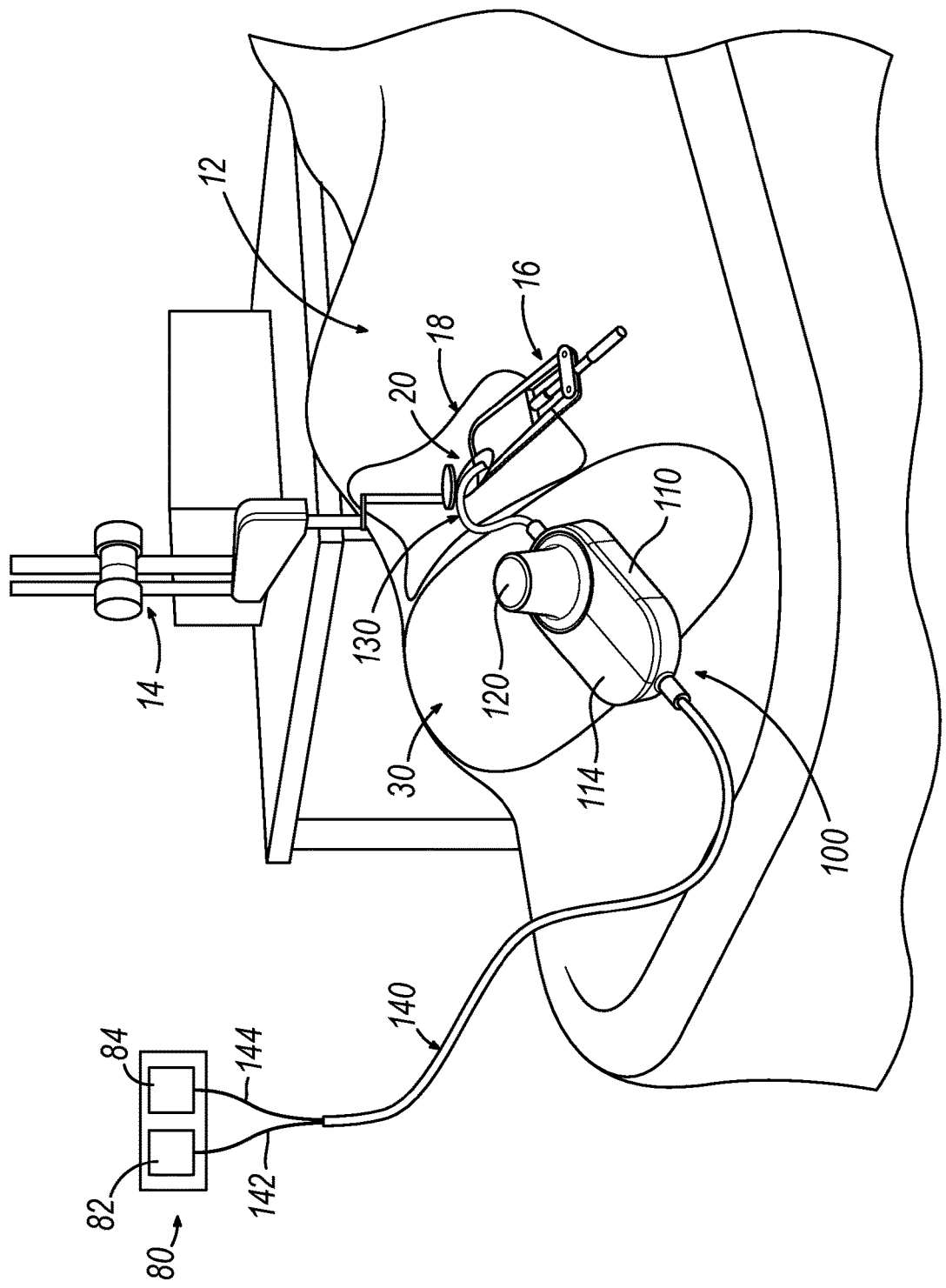
FIG. 6 depicts a perspective view of the instrument of FIG. 1, mounted near a patient, in combination with a combination of medical equipment.

In the scenario depicted in FIG. 6, instrument (100) is positioned in relation to a patient. In this example, a drape (12) is disposed over the patient, with an opening (18) formed in drape (12) near the patient's eye (20). A speculum (16) is used to keep the eye (20) open. A fixture (14) is positioned adjacent to the eye (20). Fixture (14) may be used to secure instrumentation, such as a viewing scope, relative to the patient. A magnetic pad (30) is adhered to drape (12) near the opening (18) adjacent to the eye (20). Instrument (100) is placed on magnetic pad (30); and is removably secured thereto via magnetic attraction. For instance, one or more permanent magnets (not shown) may be positioned within body (110) near bottom portion (112); and these magnets are magnetically attracted to one or more ferrous elements (not shown) contained within magnetic pad (30). These magnets and magnetic pad (30) may be configured in accordance with at least some of the teachings of U.S. Pub. No. 2017/0360606, entitled "Injection Device for Subretinal Delivery of Therapeutic Agent," published Dec. 21, 2017, the disclosure of which is incorporated by reference herein. Instrument (100) is oriented to enable insertion of flexible cannula (130) of instrument (100) into the eye (20). Examples processes for inserting and positioning cannula (130) in the eye (20) are described in greater detail below with reference to FIGS. 7A-8B.

In the present example, instrument (100) is coupled with a fluid delivery system (80) via conduit assembly (140). In this example, fluid delivery system (80) comprises a bleb fluid source (82) and a therapeutic agent fluid source (84). Bleb fluid source (82) is coupled with a bleb fluid conduit (142) of conduit assembly (140); and therapeutic agent fluid source (84) is coupled with a therapeutic agent conduit (144) of conduit assembly (140). Conduits (142, 144) are in fluid communication with needle (150). In some versions, fluid sources (82, 84) comprise syringes. In some other versions, fluid sources (82, 84) comprise separate reservoirs and one or more associated pumps and/or valves, etc.

FIGS. 7A-8B depict an exemplary procedure in which a leading bleb fluid is delivered to the subretinal space from more than one site in the suprachoroidal space. Delivering the bleb fluid from more than one site instead of just one single site may be preferable for various reasons. For instance, in some cases, delivering a substantial amount of bleb fluid from just one single site may cause a detached portion of the retina to stretch, which may be undesirable. Delivering the same total volume of bleb fluid from two or more sites may reduce the risk of stretching in the detached portion of the retina. Moreover, delivering a certain total volume of bleb fluid from two or more sites may ultimately result in a detached portion of the retina with a surface area that is larger than the surface area that could be achieved by delivering the same volume of bleb fluid from just one single site.

As noted below, the separate subretinal delivery sites for bleb fluid may be far enough apart such that the corresponding resulting hemispheres under the detached portion of the retina remain isolated from each other, such that the retina is detached from the choroid in a plurality of discrete regions. Alternatively, separate delivery sites for bleb fluid may be close enough such that the corresponding resulting hemispheres under the detached portion of the retina merge with each other, resulting in a single continuous region of the detached portion. Even in these scenarios, the total surface area of ocular tissue that can be subsequently contacted by the delivered therapeutic agent (92) may still exceed the total surface area of ocular tissue that could be subsequently contacted by the delivered therapeutic agent (92) after having the same total volume of bleb fluid (90) being delivered to just one single site.

Figure 7A:
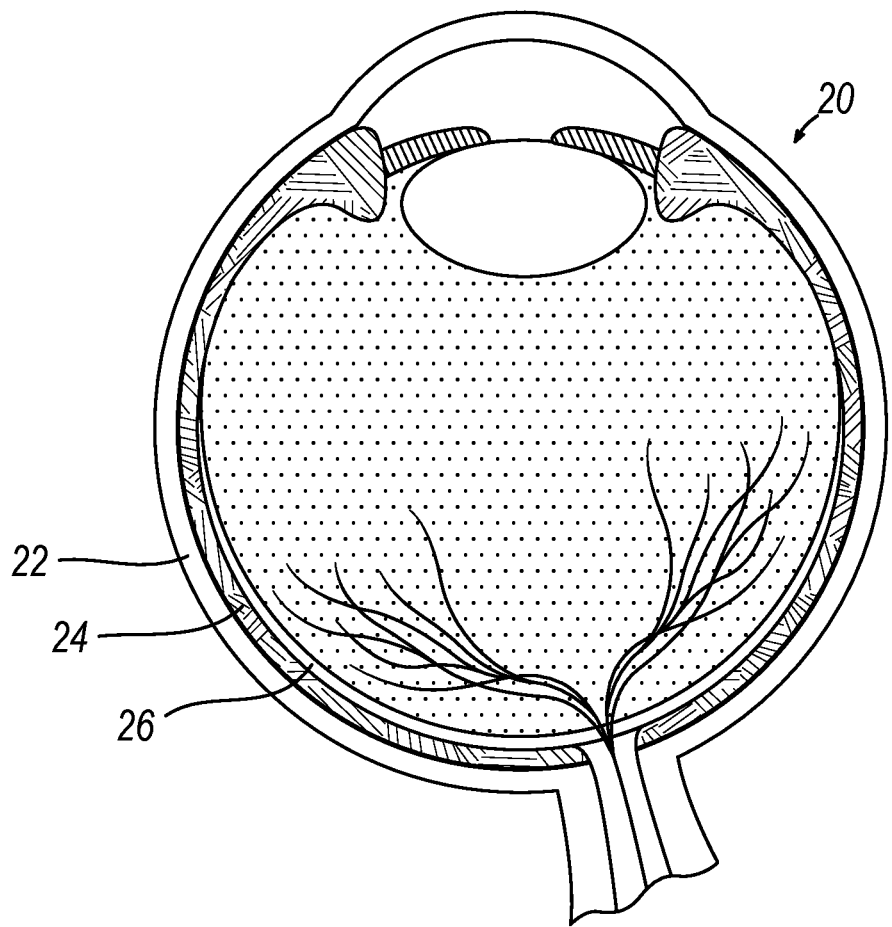
FIG. 7A depicts a cross-sectional side view of an eye of a patient.

FIG. 7A shows an eye (20) before the procedure is initiated. At this stage, the operator may immobilize tissue surrounding the patient's eye (20) (e.g., the eyelids), using speculum (16) and/or any other instrument suitable for immobilization. While immobilization described herein with reference to tissue surrounding eye (20), eye (20) itself may remain free to move. In some versions, once the tissue surrounding eye (20) has been immobilized, an eye chandelier port (not shown) is inserted into eye (20), to provide intraocular illumination when the interior of eye (20) is viewed through the pupil. Alternatively, an eye chandelier port need not necessarily be used.

Figure 7B:
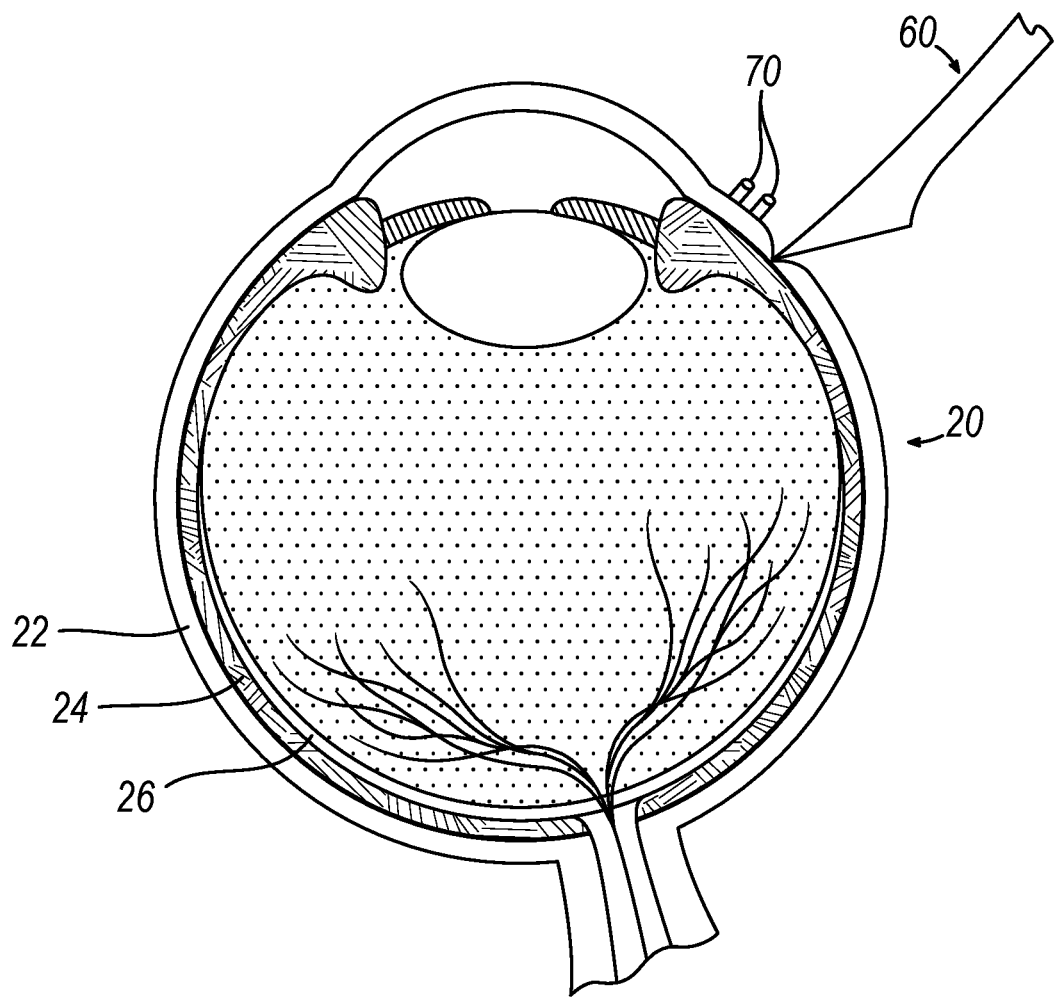
FIG. 7B depicts a cross-sectional side view of the eye of FIG. 7A, with a suture loop attached to the eye, and with a sclerotomy being performed.

Once the tissue surrounding the eye (20) has been sufficiently immobilized (and, optionally, an eye chandelier port installed), the sclera (22) may be accessed by dissecting the conjunctiva by incising a flap in the conjunctiva and pulling the flap posteriorly. After such a dissection is completed, the exposed surface of the sclera (22) may optionally be blanched using a cautery tool to minimize bleeding. Once conjunctiva dissection is complete, the exposed surface of the sclera (22) may optionally be dried using a WECK-CEL or other suitable absorbent device. A template may then be used to mark the eye (20), as described in U.S. Pat. No. 10,226,379, the disclosure of which is incorporated by reference herein; and/or U.S. Pub. No. 2017/0360605, entitled "Guide Apparatus for Tangential Entry into Suprachoroidal Space," published Dec. 21, 2017, the disclosure of which is incorporated by reference herein. The operator may then use a visual guide created using the template to attach a suture loop assembly (70) and to perform a sclerotomy, as shown in FIG. 7B, using a conventional scalpel (60) or other suitable cutting instrument. By way of example only, suture loop assembly (70) may be formed in accordance with at least some of the teachings of U.S. Pat. No. 10,226,379. Alternatively, in lieu of suture loop assembly (70), the operator may install a guide tack in accordance with at least some of the teachings of U.S. Pub. No. 2017/0360605. Other devices that may be secured to the eye (20) to guide cannula (130) into the eye (20) will be described in greater detail below.

The sclerotomy procedure with scalpel (60) forms a small incision through the sclera (22) of the eye (20). The sclerotomy is performed with particular care to avoid penetration of the choroid (24). Thus, the sclerotomy procedure provides access to the space between the sclera (22) and the choroid (24). Once the incision is made in the eye (20), a blunt dissection may optionally be performed to locally separate the sclera (22) from the choroid (24). Such a dissection may be performed using a small blunt elongate instrument, as will be apparent to those skilled in the art in view of the teachings herein.

Figure 7C:
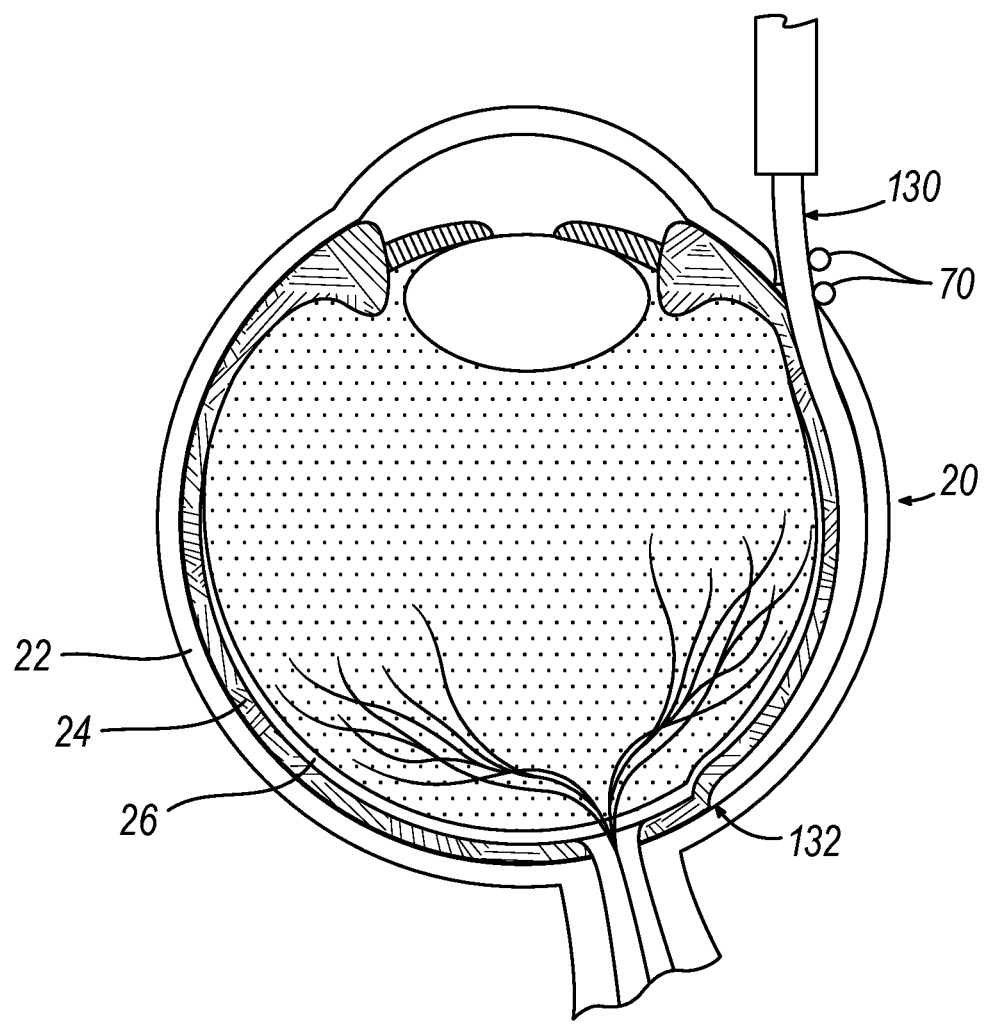
FIG. 7C depicts a cross-sectional side view of the eye of FIG. 7A, with the cannula of FIG. 2 being inserted through a sclerotomy opening and in between the sclera and choroid of the eye, with the distal end of the cannula at a first position.

With the sclerotomy procedure performed, the operator may insert cannula (130) of instrument (100) through the incision and into the space between the sclera (22) and the choroid (24). As can be seen in FIG. 7C, cannula (130) is directed through suture loop assembly (70) and into the incision. Suture loop assembly (70) may stabilize cannula (130) during insertion. Additionally, suture loop assembly (70) maintains cannula (130) in a generally tangential orientation relative to the incision. Such tangential orientation may reduce trauma as cannula (130) is guided through the incision. As cannula (130) is inserted into the incision through suture loop assembly (70), an operator may use forceps or other instruments to further guide cannula (130) along an atraumatic path. As noted above, a guide tack (or other device) may be used in lieu of suture loop assembly (70). Cannula (130) is advanced until distal end (132) is located at a first position at the posterior region of the retina (26). Various suitable ways of visualizing distal end (132) to thereby observe proper positioning of distal end (132) will be apparent to those skilled in the art in view of the teachings herein.

Figure 7D:
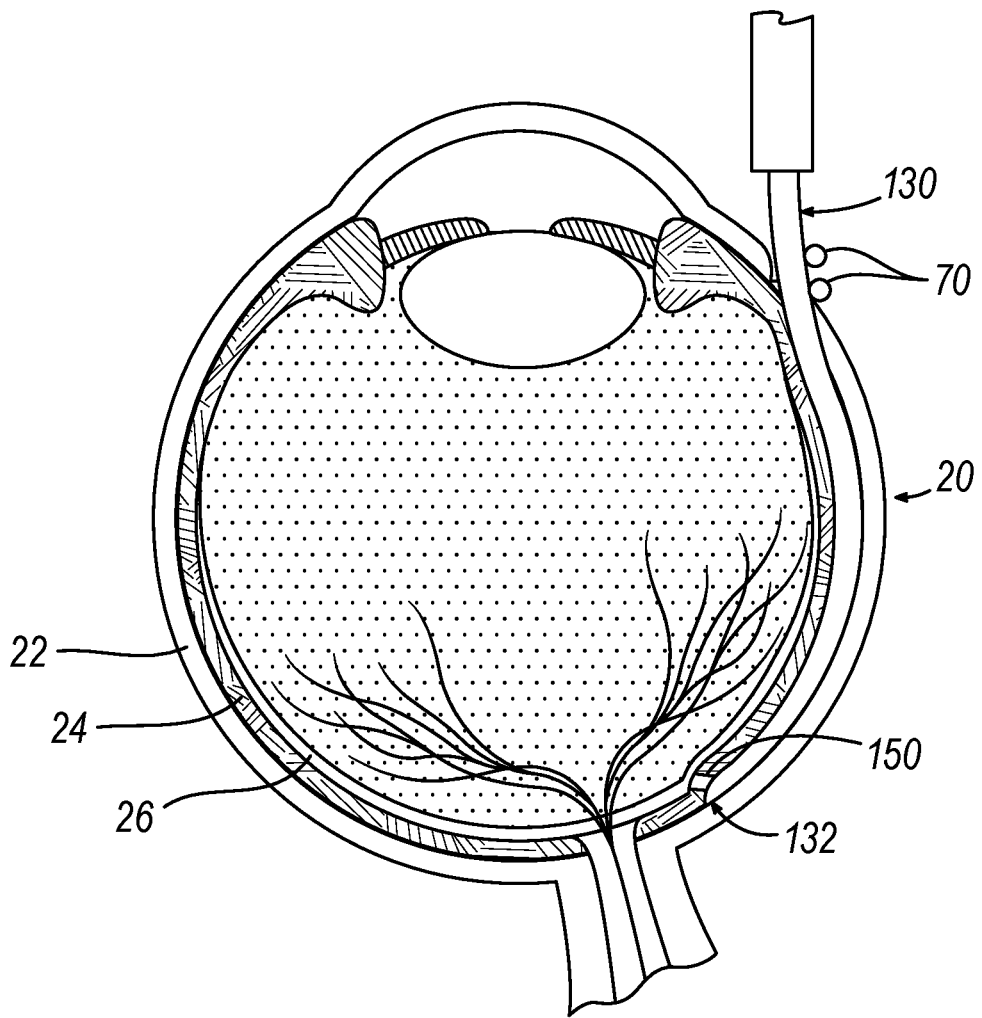
FIG. 7D depicts a cross-sectional side view of the eye of FIG. 7A, with the distal end of the cannula at the first position, and with the needle of FIG. 5 being advanced through the choroid to access the subretinal space from the first position.
Figure 7E:
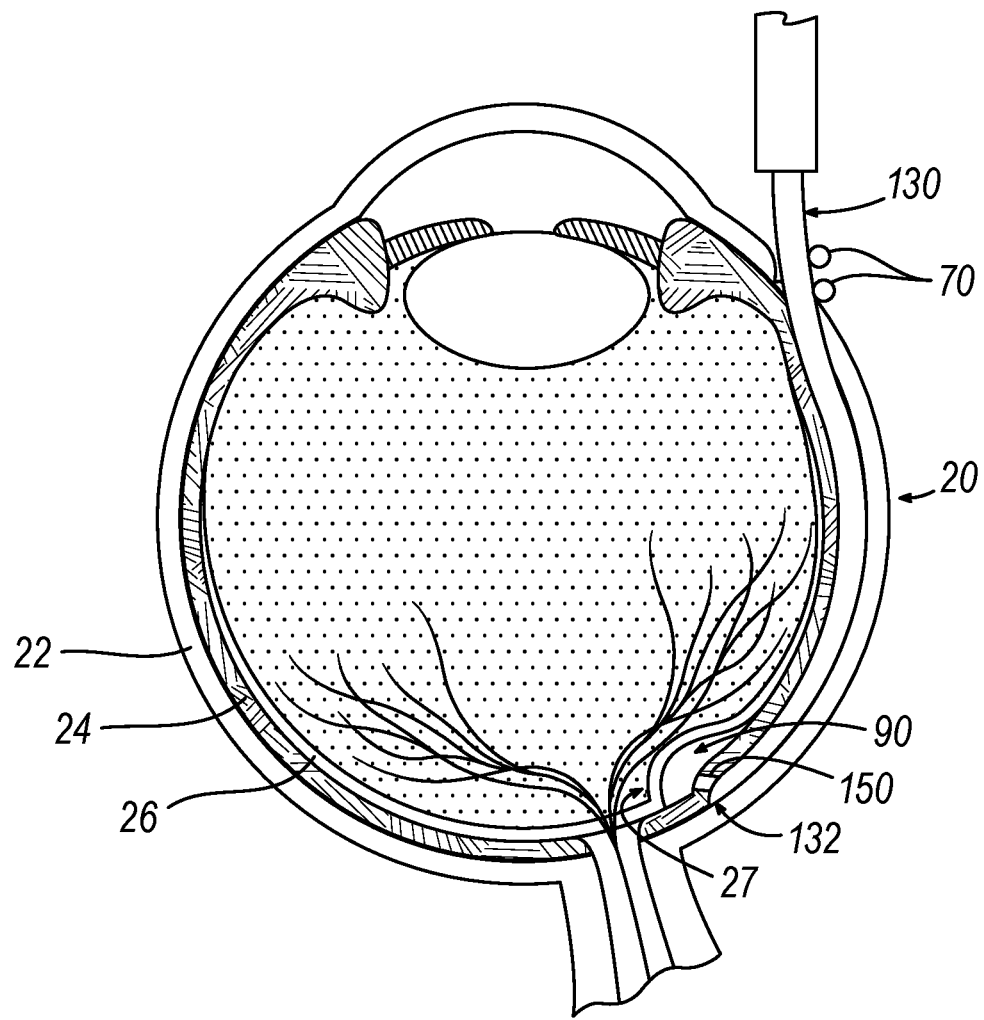
FIG. 7E depicts a cross-sectional side view of the eye of FIG. 7A, with the needle of FIG. 5 dispensing a first volume of leading bleb fluid from the first position to provide separation between a first region of the retina and the choroid.

Once cannula (130) has been advanced to the position shown in FIG. 7C, the operator may advance needle (150) of instrument (100) distally as described above by actuating knob (120). As can be seen in FIG. 7D, needle (150) is advanced relative to cannula (130) such that needle (150) pierces through the choroid (24) without penetrating the retina (26). The operator then actuates fluid delivery system (80) to drive bleb fluid from bleb fluid source (82), thereby delivering a first volume of bleb fluid (90) to the subretinal space from the first position, as shown in FIG. 7E. This forms a first region of a detached portion (27) of the retina (26).

Figure 7F:
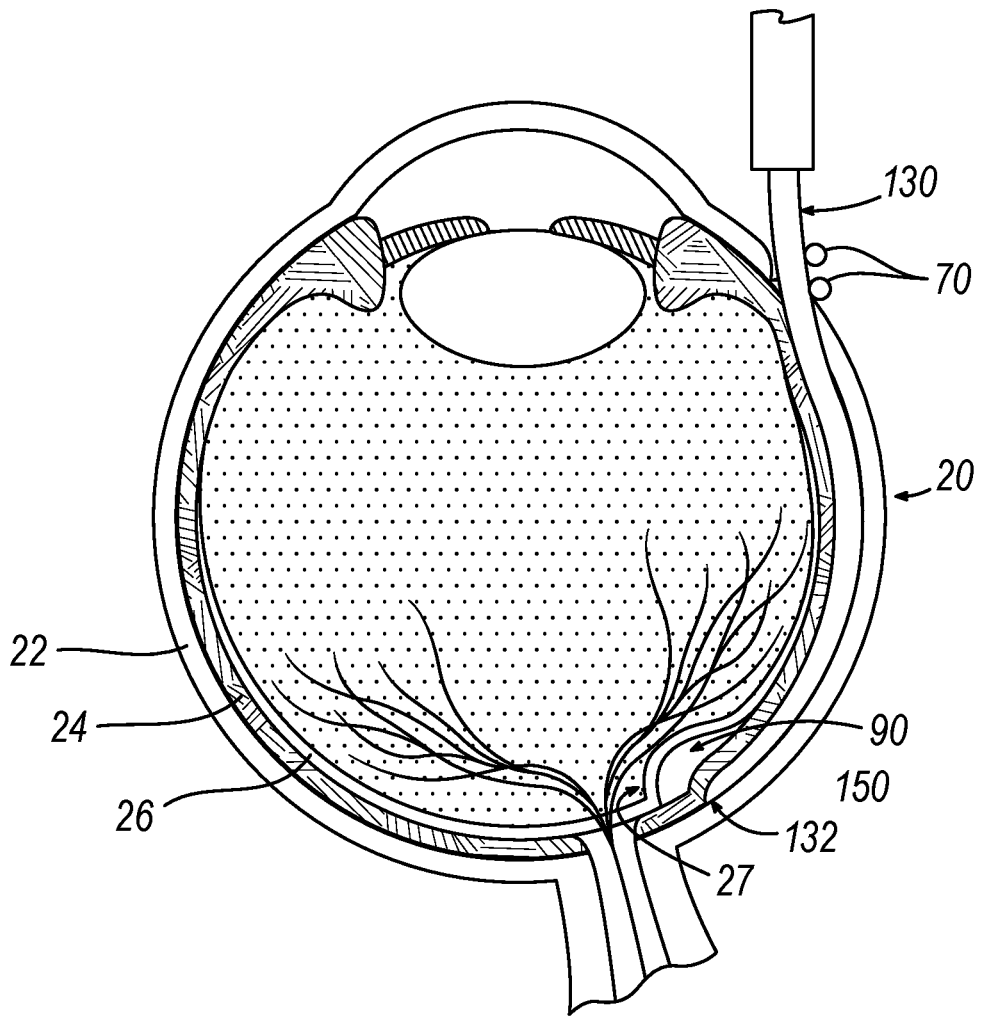
FIG. 7F depicts a cross-sectional side view of the eye of FIG. 7A, with the distal end of the cannula at the first position, and with the needle of FIG. 5 being retracted back into the cannula after dispensing the first volume of leading bleb fluid.
Figure 7G:
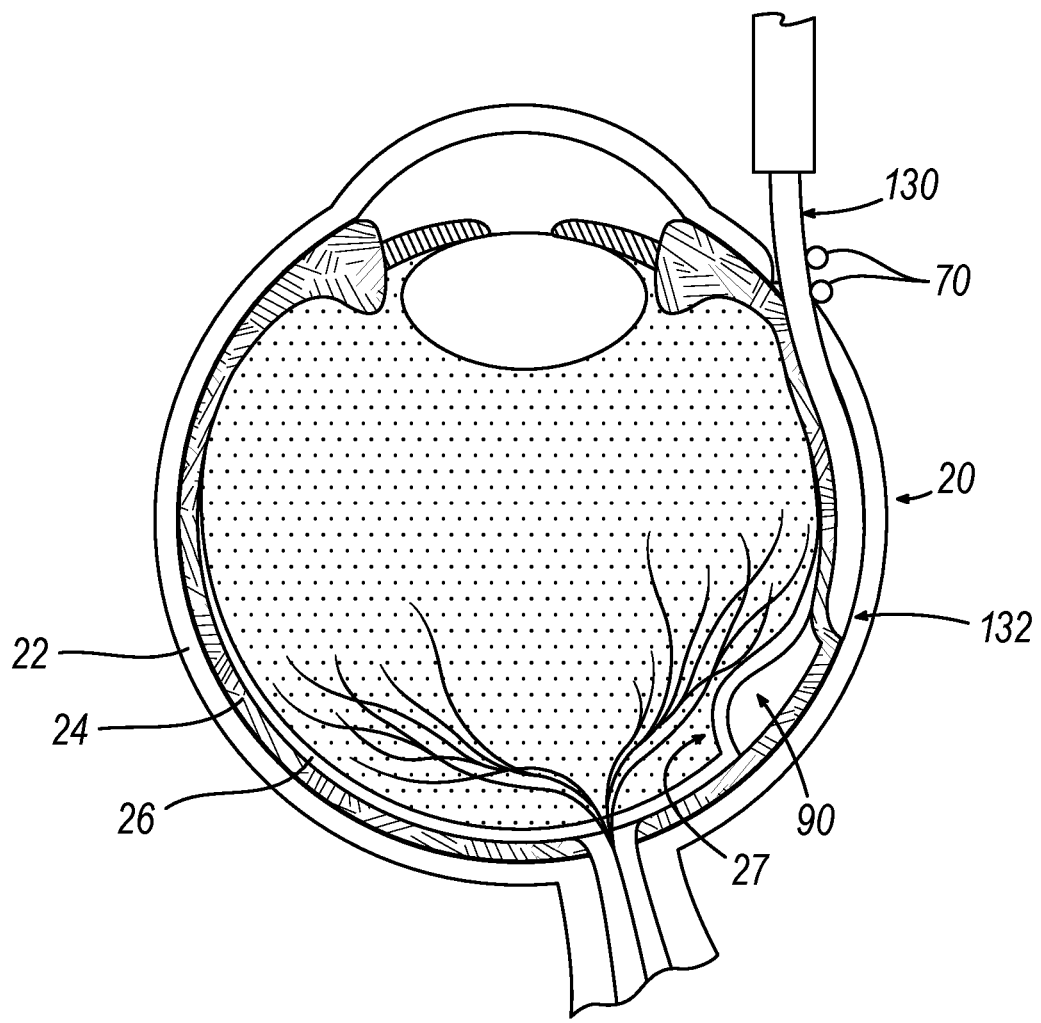
FIG. 7G depicts a cross-sectional side view of the eye of FIG. 7A, with the distal end of the cannula at a second position between the sclera and choroid of the eye.
Figure 7H:
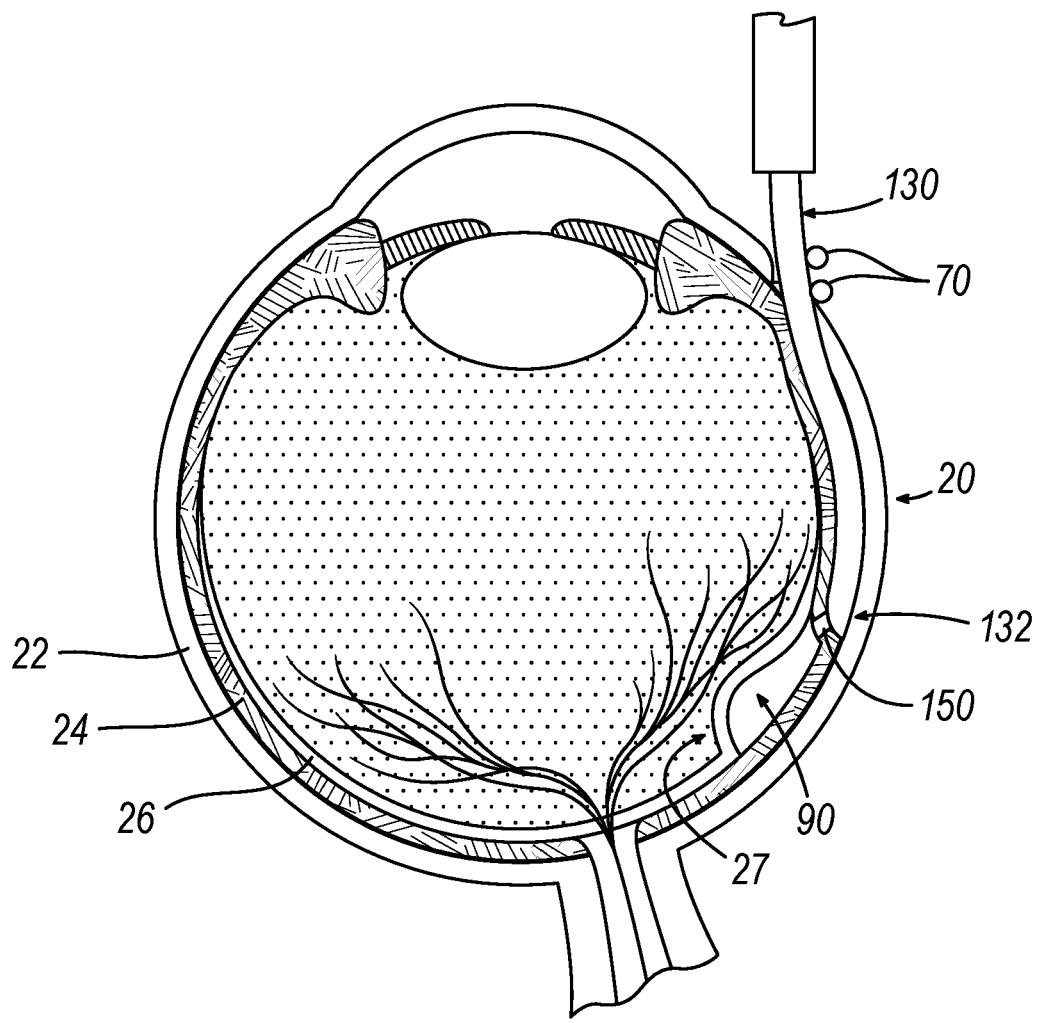
FIG. 7H depicts a cross-sectional side view of the eye of FIG. 7A, with the distal end of the cannula at the second position, and with the needle of FIG. 5 being advanced through the choroid to access the subretinal space from the second position.
Figure 7I:
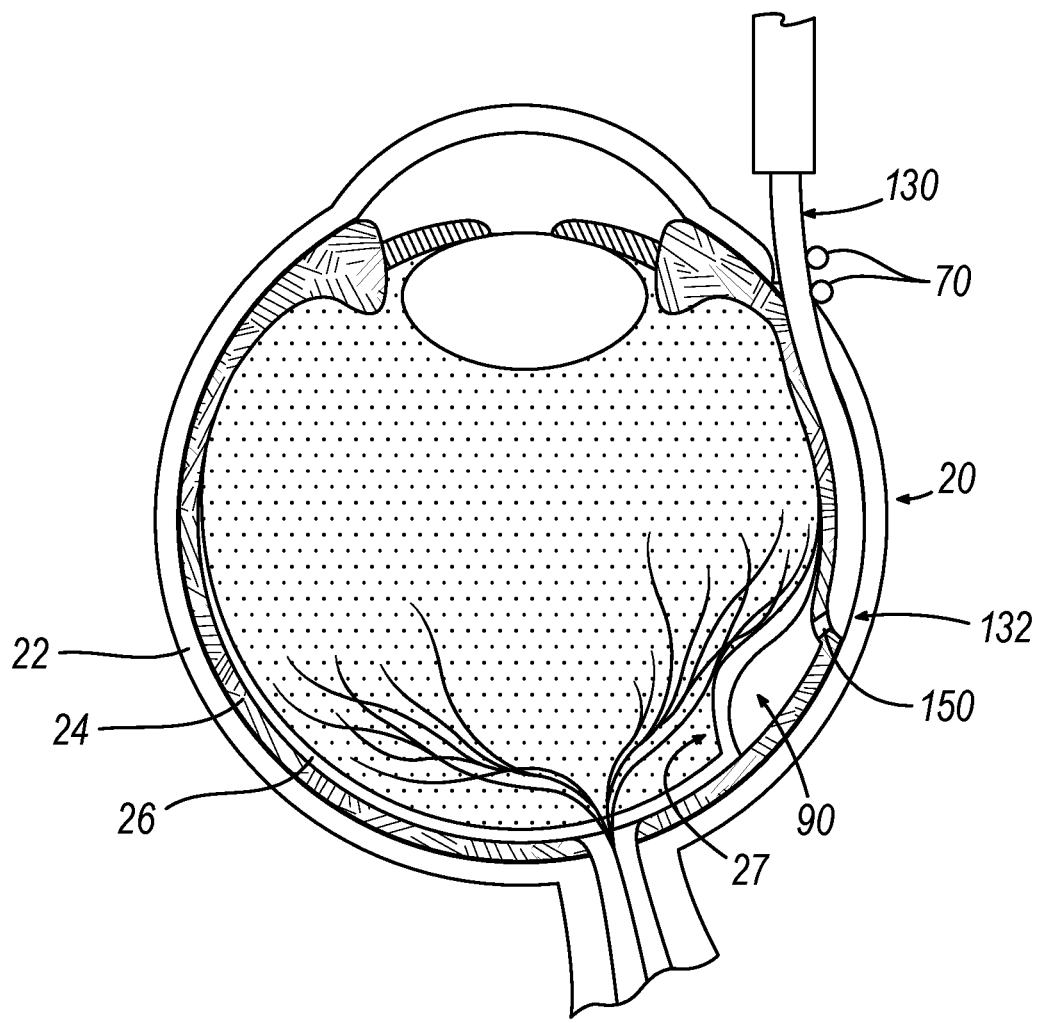
FIG. 7I depicts a cross-sectional side view of the eye of FIG. 7A, with the needle of FIG. 5 dispensing a second volume of leading bleb fluid from the second position to provide separation between a second region of the retina and the choroid.
Figure 7J:
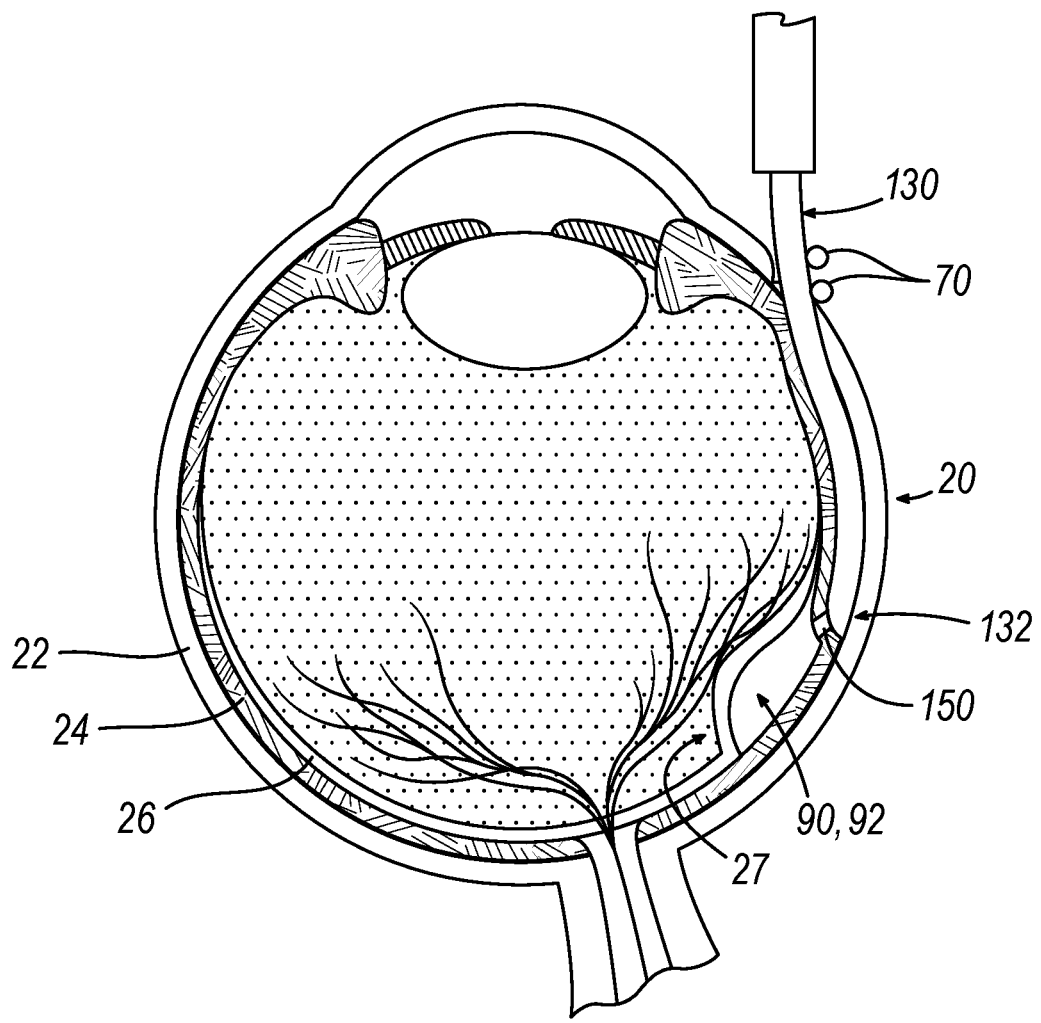
FIG. 7J depicts a cross-sectional side view of the eye of FIG. 7A, with the needle of FIG. 5 dispensing a volume of therapeutic agent from the second position to treatment to the subretinal space between the retina and the choroid.

After delivering the first volume of bleb fluid (90), the operator may actuate knob (120) to retract needle (150) back into cannula (132), as shown in FIG. 7F. The operator may then pull cannula (132) to locate distal end (132) at a second position at the posterior region of the retina (26), as shown in FIG. 7G. Once cannula (130) has been located at the position shown in FIG. 7G, the operator may again advance needle (150) of instrument (100) distally as described above by actuating knob (120). As can be seen in FIG. 7H, needle (150) is advanced relative to cannula (130) such that needle (150) pierces through the choroid (24) without penetrating the retina (26). The operator then actuates fluid delivery system (80) to drive bleb fluid from bleb fluid source (82), thereby delivering a second volume of bleb fluid (90) to the subretinal space from the second position, as shown in FIG. 7I. This forms a second region of a detached portion (27) of the retina (26). In this example, the first and second delivery positions are substantially close to each other such that the two volumes of delivered bleb fluid (90) effectively merge with each other to form a collectively detached portion (27) of the retina (26). In some other versions, the first and second delivery positions are far enough from each other such that the two volumes of delivered bleb fluid (90) remain isolated from each other to form corresponding discrete detached portions (27) of the retina (26). While the second delivery site is anterior to the first delivery site in this example, the second delivery site may instead have any other suitable relationship with the first delivery site.

After reaching the stage shown in FIG. 7I, the delivered bleb fluid (90) may be aspirated away. This is merely optional and is not necessarily required. Either way, needle (150) may be used to deliver the therapeutic agent (92) to the region under detached portion (27) as described above with reference to FIG. 7J. The total surface area of ocular tissue that can be contacted by the delivered therapeutic agent (92) may exceed the total surface area of ocular tissue that could otherwise be subsequently contacted by the delivered therapeutic agent (92) after having the same total volume of bleb fluid (90) being delivered from just one single delivery position. Moreover, the procedure shown in FIGS. 7A-7J may impart less tensile stress on the retina (26) than the tensile stress imparted on the retina (26) by a procedure where the same amount of fluid would be delivered from just one suprachoroidal position, such that the procedure shown in FIGS. 7A-7J may reduce the risk of stretching the retina (26).

Figure 8A:
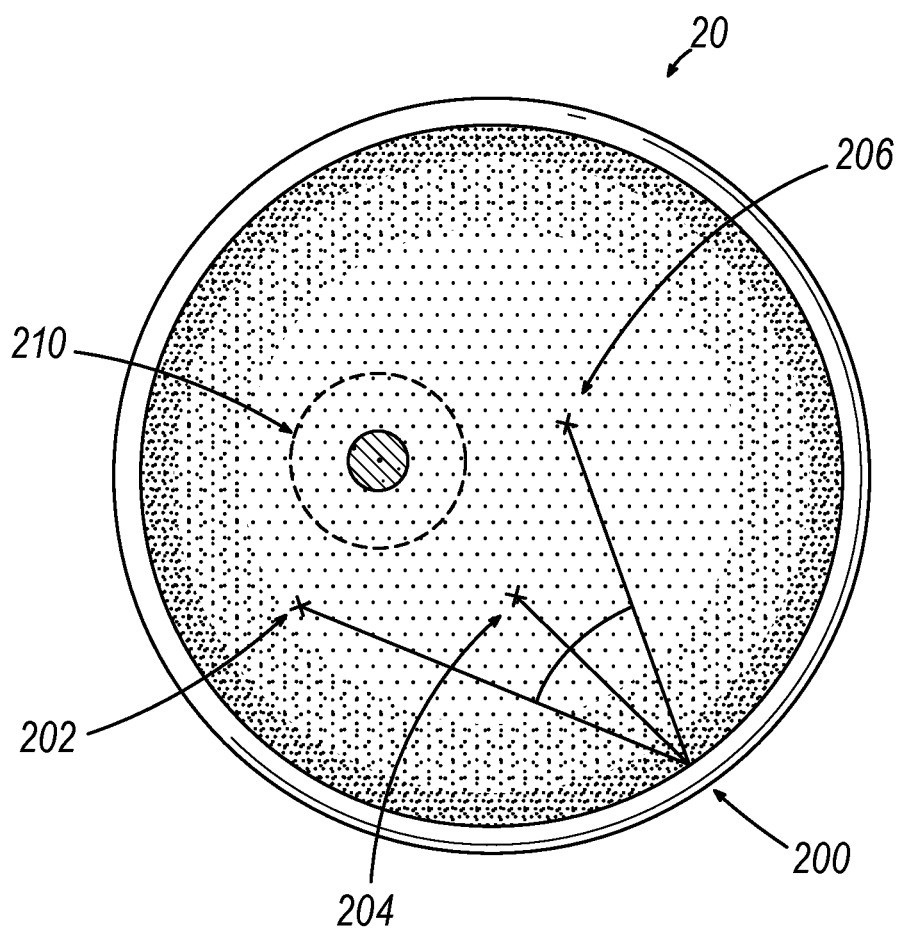
FIG. 8A depicts a cross-sectional top view of the eye of FIG. 7A, schematically depicting an example of a set of leading bleb delivery sites between corresponding regions of the retina and the choroid.
Figure 8B:
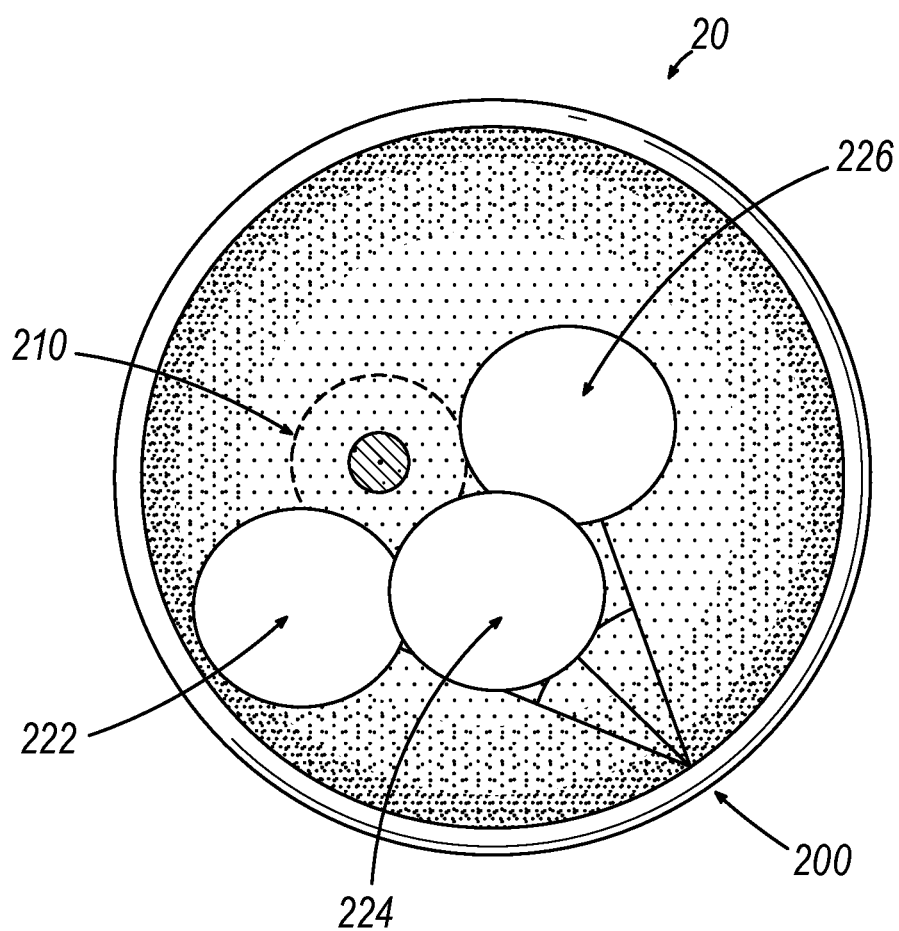
FIG. 8B depicts a cross-sectional top view of the eye of FIG. 7A, schematically depicting leading bleb fluid delivered at the delivery sites of FIG. 8A.

While the above-described procedure of FIGS. 7A-7J provides leading bleb (90) delivery sites that are spaced apart from each other in an anterior-posterior relationship, it should be understood that the leading bleb (90) delivery sites may be spaced apart from each other in any other suitable fashion. By way of example only, FIG. 8A shows three delivery sites (202, 204, 206) that may be accessed from a single sclerotomy insertion point (200). In this example, the three delivery sites (202, 204, 206) are generally positioned around the macula (210) of the eye (20). These delivery sites (202, 204, 206) are not necessarily anterior or posterior to each other. In order to reach these delivery sites (202, 204, 206), cannula (130) may first be inserted to position distal end (132) at the first delivery site (202); then be slightly retracted and pivoted at the sclerotomy to position distal end (132) at the second delivery site (204); then be pivoted at the sclerotomy again and then be advanced to position distal end (132) at the third delivery site (206). As shown in FIG. 8B, when bleb fluid (90) is delivered to each of these delivery sites (202, 204, 206), the resulting bleb regions (222, 224, 226) are adjacent to each other around the macula (210). As noted above, these bleb regions (222, 224, 226) may merge with each other to create one continuous detached portion (27) of the retina (26). Alternatively, these bleb regions (222, 224, 226) may remain isolated from each other to three corresponding discrete detached portions (27) of the retina (26).

In versions of the procedures shown in FIGS. 8A-8B where the separately delivered volumes of bleb fluid (90) result in discrete detached portions (27) of the retina (26), the therapeutic agent (92) may be delivered under each discrete detached portion (27) of the retina (26). In some instances, the therapeutic agent (92) may be delivered immediately after each volume of bleb fluid (90) is delivered, such that a first volume of therapeutic agent (92) is delivered to a first site immediately after the first volume of bleb fluid (90) is delivered to the first site, before the second volume of bleb fluid (90) is delivered to the second site. Alternatively, all separate volumes of bleb fluid (90) may be delivered first; and then therapeutic agent (92) may be delivered. This procedure may be used to determine the extent to which the delivered volumes of bleb fluid (90) merge with each other, such that only a single volume of therapeutic agent (92) needs to be delivered to any region associated with merged volumes of bleb fluid (90).

III. EXAMPLES OF OCULAR CANNULA GUIDES

As noted above, a suture loop assembly (70) may be installed in the eye (20) of a patient in order to stabilize and guide cannula (130) during insertion of cannula (130) into the eye (20). In some cases, the formation of suture loop assembly (70) may be somewhat time consuming. In addition, it may be difficult to provide consistent spacing between the suture loops of a suture loop assembly (70); and between the suture loops and the eye (20). Such variations in spacing may yield variations in the entry angle and/or variations in the force required to insert cannula (130) through suture loop assembly (70). It may therefore be desirable to provide a guide device that provides the stabilizing and guiding functionality of suture loop assembly (70); yet that is faster and easier to install in the eye (20) than suture loop assembly (70), yielding more consistent results.

Furthermore, it may be desirable to provide such a guide device that accommodates re-angulation of cannula (130) in order to deliver fluids at various locations within the eye (20), without having to remove cannula (130) from the eye (20) (e.g., by accommodating lateral pivotal movement of cannula (130) at the incision (23) where cannula (130) enters the sclera (22)), in procedures similar to those described above with reference to FIGS. 8A-8B. In addition, it may be desirable to provide guide devices that minimize trauma to the conjunctiva layer of the eye.

Various illustrative examples of such guide devices are described in greater detail below. The guide devices described below may provide faster installation times, minimize variability due to surgeon technique, and require a lower level of expertise such that less surgeon training will be necessary. Additionally, the guide devices may reduce the amount of exposed sclera (22) required, allowing for a smaller access incision that may provide closure and healing times that are faster than might otherwise be achieved. At the end of the procedure, the guide device may be removed from the eye such that no foreign body will be left in the eye. Such guide devices may also accommodate lateral pivotal movement of cannula (130) at the site where cannula (130) enters the sclera (22); and minimize trauma to the conjunctiva layer of the eye (20).

A. Overview of Multi-Angle Cannula Guide

FIGS. 9-10B show an example of a cannula guide (300) that may be used to guide cannula (130) during insertion of cannula (130) into the eye (20), such as during a procedure as described above and shown in FIGS. 7A-8B. Cannula guide (300) may be installed directly on the eye (20) while a speculum (16) holds the eye (20) open. Cannula guide (300) of this example includes an annular body (302) with a guide portion (310). Guide portion (310) includes a pair of rails (314) that define a recess (312). Recess (312) is tapered to provide a funneled pathway toward an incision (23) that is formed in the sclera (22) (e.g., using a conventional sclerotomy technique). The distal ends of rails (314) are thus positioned adjacent to terminal ends of the incision (23). In the present example, the position and orientation of rails (314) are configured such that the distance between the distal ends of rails (314) closely corresponds with the length of the incision (23).

As shown in FIGS. 10A-10B, a central axis (CA) is defined perpendicularly relative to the incision (23). While this central axis (CA) appears to be straight in FIGS. 10A-10B, the central axis (CA) may be understood to extend circumferentially around the eye (20), while still being oriented perpendicularly relative to the incision (23). As also shown in FIGS. 10A-10B, the funnel shape of recess (312), as provided by the converging orientation of rails (314), facilitates entry of cannula (130) into the incision (23) at various angles that are oblique to the central axis (CA). FIG. 10A shows cannula (130) disposed in the incision (23) along an insertion axis (IA) that defines one extreme angle ($\theta_1$) with the central axis (CA); while FIG. 10B shows cannula (130) disposed in the incision (23) along an insertion axis (IA) that defines an opposing extreme angle ($\theta_2$) relative to the central axis (CA). Of course, cannula (130) may also be disposed within incision (23) along an insertion axis (IA) that defines any other suitable angle relative to the central axis (CA), between the extreme angles ($\theta_1$, $\theta_2$) that are depicted. It should be understood that cannula (130) may be laterally pivoted at the incision (23) to achieve the various insertion axes (IA) at angles within the range including the extreme angles ($\theta_1$, $\theta_2$) that are depicted. By way of example only, cannula guide (300) may be configured such that each extreme angle ($\theta_1$, $\theta_2$) may be between approximately 10 degrees and approximately 40 degrees, thereby allowing cannula (130) to be pivoted along a full range of angular motion ($\theta_1+\theta_2$) up to approximately 20 degrees or up to approximately 80 degrees. As another example, cannula guide (300) may be configured such that each extreme angle ($\theta_1$, $\theta_2$) may be approximately 30 degrees, thereby allowing cannula (130) to be pivoted along a full range of angular motion ($\theta_1+\theta_2$) up to approximately 60 degrees. Even if cannula guide (300) allows such extremes within the full range of angular motion ($\theta_1+\theta_2$), an operator may choose to pivot cannula (130) along smaller angular ranges within extreme angles ($\theta_1$, $\theta_2$), despite cannula guide (300) permitting pivotal movement at the larger angles.

While the insertion axis (IA) appears to be straight in FIGS. 10A-10B, the insertion axis (IA) may be understood to extend circumferentially around the eye (20). Thus, the portion of cannula (130) that is disposed in the suprachoroidal space of the eye (20) may still follow the curvature of the eye (20) despite being positioned along different insertion axes (IA). Moreover, cannula (130) may be adjusted to deliver fluid from various insertion axes (IA) without cannula (130) needing to be withdrawn from the eye (20) and reinserted in the eye (20). Thus, the variability of the insertion axis (IA), as provided by cannula guide (300), may facilitate multi-bleb procedures such as those described above with reference to FIGS. 8A-AB, with different insertion axes (IA) being used to target different delivery sites (202, 204, 206).

As also shown in FIGS. 10A-10B, some versions of guide portion (310) may include web (316) spanning across recess (312) from one rail (314) to the other rail (314). Such a web (316) may be formed of a rigid plastic, an elastic membrane, an inelastic membrane, or any other suitable kind of material. Such a web (316) may also be transparent to facilitate visualization of distal end (132) of cannula (130) entering the incision (23). Web (316) may also have small perforations that allow visualization when utilizing a non-transparent material. Web (316) may further cooperate with rails (314) to help physically guide distal end (132) of cannula (130) into the incision (23). Web (316) is optional and may be omitted in some versions.

While cannula guide (300) of the present example includes an annular body (302), other versions may lack such an annular body (302). For instance, some variations of cannula guide (300) may include only guide portion (310) and a minimal adjacent structure to secure cannula guide (300) to the eye (20) or to otherwise ground cannula guide (300) relative to the eye (20). Examples of alternative securing or grounding structures are described in greater detail below. The variations of cannula guides described below may also facilitate disposition of cannula (130) in an incision (23) along various insertion axes (IA) at various angles ($\theta$) relative to a central axis (CA) of the incision (23). It should therefore be understood that the above discussion of different insertion axes (IA) and angles ($\theta$), in conjunction with the multi-bleb procedure depicted in FIGS. 8A-8B, may also readily apply to the various other examples of cannula guides described below.

B. Cannula Guide with Conjunctiva Engagement Features

Figure 11:
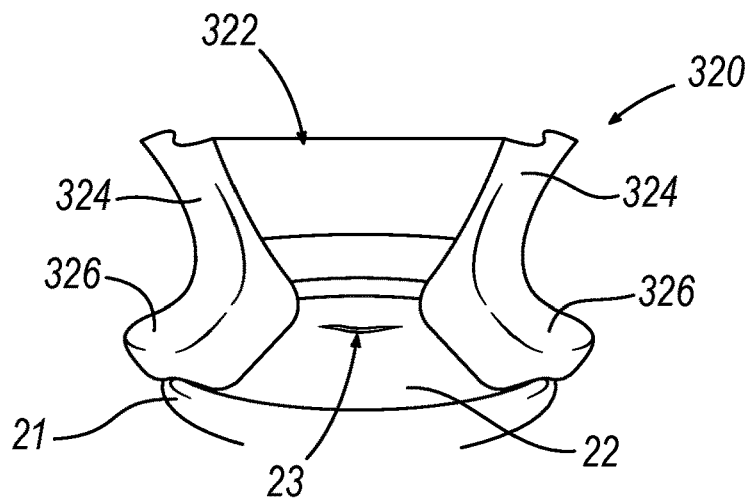
FIG. 11 depicts a perspective view of a portion of a cannula guide engaged with conjunctiva of an eye of a patient.
Figure 12A:
FIG. 12A depicts a plan view of a portion of an eye of a patient, with an incision formed through a conjunctiva layer.
Figure 12B:
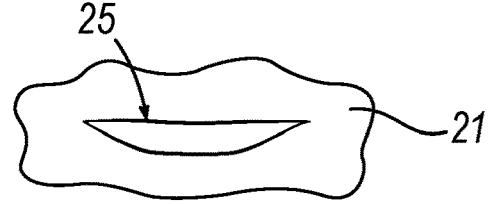
FIG. 12B depicts a plan view of the portion of the eye of FIG. 12A, with the conjunctiva layer being separated at the incision.
Figure 12C:
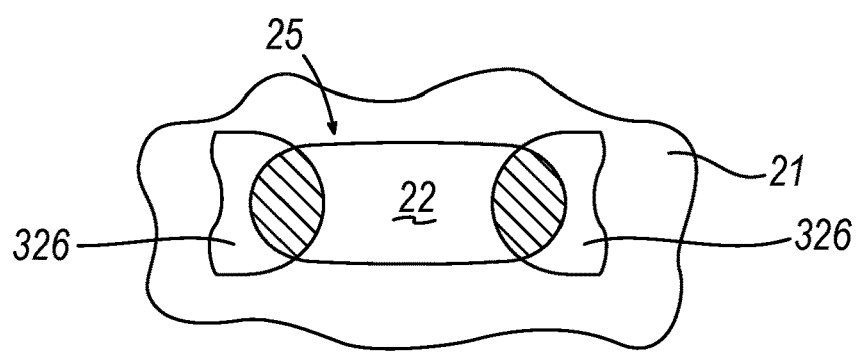
FIG. 12C depicts a plan view of the cannula guide of FIG. 11 engaged with the eye of FIG. 12B, with the cannula guide holding the conjunctiva layer in an open state to maintain exposure of a region of a sclera layer.

As noted above in the discussion of FIGS. 7A-7B, some procedures may provide for dissecting the conjunctiva by incising a flap in the conjunctiva and pulling the flap posteriorly, followed by installation of a suture loop assembly (70) in the sclera (22). In some instances, it may be desirable to avoid creation of such a flap in the conjunctiva; while still allowing sufficient access to the sclera (22) for formation of an incision (23) and insertion of cannula (130) into the incision (23). Minimizing trauma on the conjunctiva may reduce procedure times and may reduce the risk of adverse results that might otherwise be caused by mistakes in surgeon technique. FIG. 11 shows an example of a cannula guide (320) that may be used with minimal trauma to the conjunctiva; while FIGS. 12A-12C show an example of such a procedure in which cannula guide (320) may be used. The portion of cannula guide (320) depicted in FIG. 11 is substantially similar to guide portion (310) of cannula guide (300) described above. In particular, cannula guide (320) includes a pair of rails (324) that converge toward each other and cooperate to define a tapered recess (322), funneling toward an incision (23) in the sclera (22). Unlike guide portion (310), cannula guide (320) of this example further includes feet (326) positioned at respective distal ends of rails (324). Feet (326) diverge outwardly and are configured to engage conjunctiva (21), thereby maintaining exposure of the portion of sclera (22) having incision (23).

Before cannula guide (320) is installed on the eye (20), an operator may make an incision (25) in the conjunctiva (21) as shown in FIG. 12A. The operator may then spread the conjunctiva (21) at the incision (25) as shown in FIG. 12B to expose a region of the sclera (22). The operator may then position feet (326) of cannula guide (320) in the incision (25), such that feet (326) keep the conjunctiva (21) spread open at the incision (25) as shown in FIG. 12C. This arrangement may maintain exposure of a region of the sclera (22) where an incision (23) may be made for insertion of cannula (130). In some versions, the engagement between feet (326) and the conjunctiva (21) may assist in maintaining the position of cannula guide (320) on the eye (20). In addition, or in the alternative, other features may be used to maintain the position of cannula guide (320) on the eye (20). Examples of such features are described in greater detail below.

In some scenarios, after cannula (130) has been used to dispense bleb fluid (90), dispense therapeutic agent (92), aspirate fluid, or perform other operations within the eye (20), cannula (130) and cannula guide (320) may be removed from the eye (20). At this stage, the incision (25) in the conjunctiva (21) may be closed using any suitable conventional techniques. In some scenarios, this procedure may be less traumatic to the conjunctiva (21) than the flap-creating procedure described above.

C. Cannula Guide with Sliding Body

Figure 13:
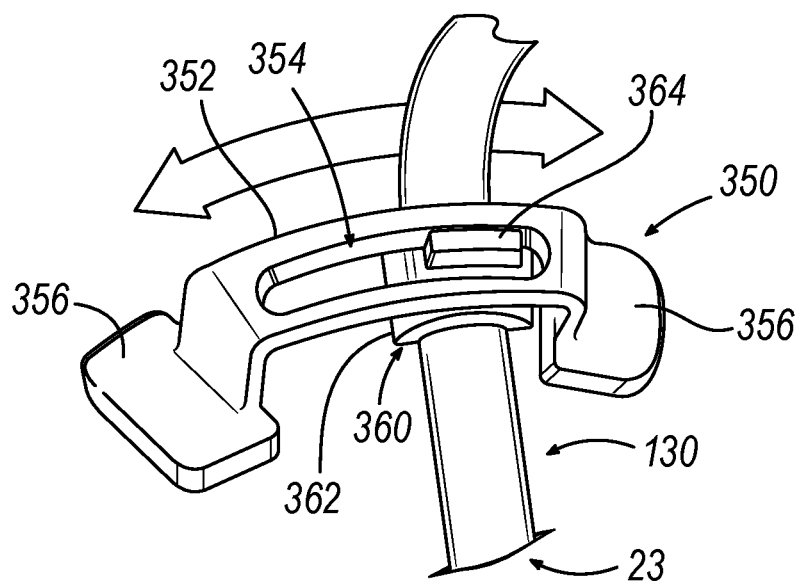
FIG. 13 depicts a perspective view of another example of a cannula guide, with the cannula guide guiding insertion of a cannula into an eye of a patient.

FIG. 13 shows another example of a cannula guide (350) guiding a cannula (130) into a scleral incision (23). Cannula guide (350) of this example includes a frame body (352) and a sliding body (360). In some versions, frame body (352) is substantially rigid. Frame body (352) is positioned to extend transversely relative to cannula (130) and includes a pair of feet (356) at the ends of frame body (352). Feet (356) may be secured to the eye (20) using any of the features or techniques described herein; or using any other features or techniques as may be apparent to those skilled in the art in view of the teachings herein. Frame body (352) is configured such that an intermediate region of frame body (352) between feet (356) will stand off from the surface of the sclera (22), thereby accommodating cannula (130) in a space between frame body (352) and the sclera (22). Sliding body (360) is positioned in this space between frame body (352) and the sclera (22); and is configured to slidably receive cannula (130).

Sliding body (360) includes a cannula engagement feature (362) and a protrusion (364). By way of example only, cannula engagement feature (362) may define an opening, a C-shaped recess, a U-shaped recess, or any other feature that is configured to slidably receive cannula (130). Protrusion (364) is slidably received in a slot (354) that is defined by frame body (352). By way of example only, protrusion (364) may include a T-shaped configuration, a dovetail configuration, or any other suitable kind of configuration that maintains protrusion (364) in slot (354) while allowing protrusion (364) to slide along slot (354). When cannula (130) is disposed in cannula engagement feature (362), sliding body (360) allows cannula (130) to slide along an insertion axis (IA); while sliding engagement between sliding body (360) and frame body (352) allows the operator to adjust the orientation of cannula (130) to various insertion axes (IA) at various angles (θ) relative to a central axis (CA) of the incision (23).

D. Cannula Guide with Wire Retainers

Figure 14:
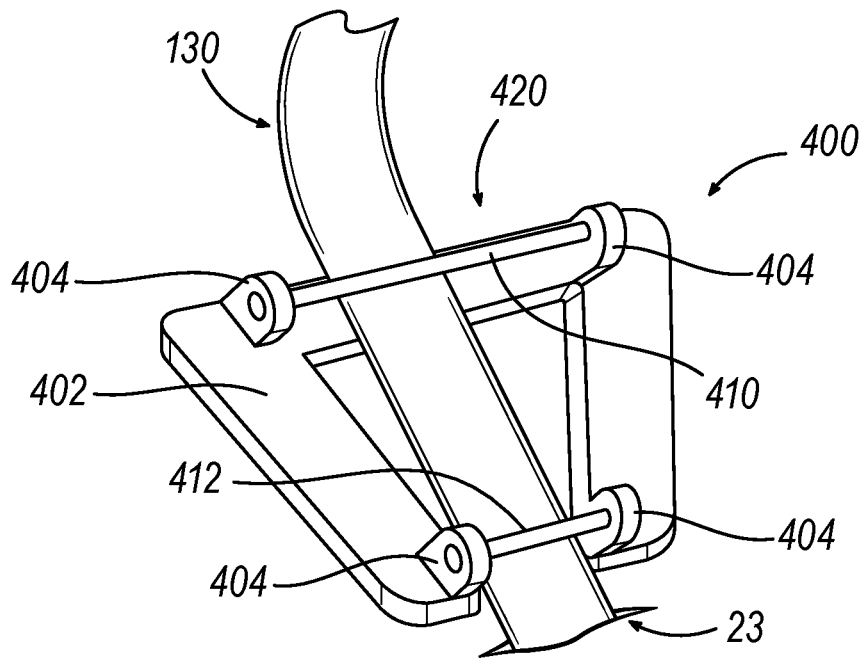
FIG. 14 depicts a perspective view of another example of a cannula guide, with the cannula guide guiding insertion of a cannula into an eye of a patient.

FIG. 14 shows another example of a cannula guide (400) guiding a cannula (130) into a scleral incision (23). Cannula guide (400) of this example includes a frame body (402) and a pair of wires (410, 412). In some versions, frame body (402) is substantially rigid. Frame body (402) may be secured to the eye (20) using any of the features or techniques described herein; or using any other features or techniques as may be apparent to those skilled in the art in view of the teachings herein. Frame body (402) has a shape resembling an isosceles trapezoid in this example, such that frame body (402) generally tapers inwardly toward incision (23).

Two pairs of bosses (404) extend transversely from frame body (402). A first wire (410) is secured to one pair of bosses (414); while a second wire (412) is secured to the other pair of bosses (404). With the tapered shape of frame body (402), first wire (410) is longer than second wire (412). In the present example, wires (410, 412) are substantially parallel with each other and are substantially parallel with the outer surface of the eye (20). Frame body (402) and wires (410, 412) cooperate to define a cannula insertion region (420), which is also substantially parallel with the outer surface of the eye (20) in the present example. As with other cannula guides described herein, cannula guide (400) of this example is configured to receive cannula (130) within this cannula insertion region (420) and thereby guide cannula (130) into the scleral incision (23), with frame body (402) and wires (410, 412) cooperating to provide such guidance. When cannula (130) is disposed in cannula insertion region (420), cannula guide (400) is further configured to allow cannula (130) to slide along an insertion axis (IA); while also allowing the operator to adjust the orientation of cannula (130) to various insertion axes (IA) at various angles (θ) relative to a central axis (CA) of the incision (23).

E. Cannula Guide with Rails and Cross-Beam

Figure 15:
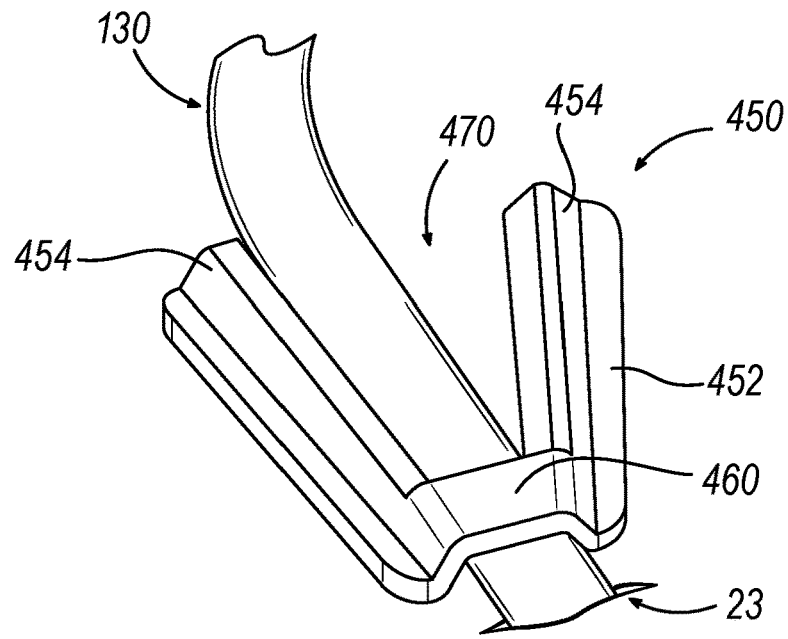
FIG. 15 depicts a perspective view of another example of a cannula guide, with the cannula guide guiding insertion of a cannula into an eye of a patient.

FIG. 15 shows another example of a cannula guide (450) guiding a cannula (130) into a scleral incision (23). Cannula guide (450) of this example includes a frame body (452) with a pair of rails (454) and a cross-beam (460). In some versions, frame body (452) is substantially rigid. Frame body (452) may be secured to the eye (20) using any of the features or techniques described herein; or using any other features or techniques as may be apparent to those skilled in the art in view of the teachings herein. Frame body (452) has a V shape in this example, such that frame body (452) generally tapers inwardly toward the incision (23).

Rails (454) extend generally perpendicularly away from the surface of the sclera (22) and follow the V-shaped profile of frame body (452), such that rails (454) convergingly taper toward the incision (23). Cross-beam (460) extends transversely between rails (454) at the distal ends of rails (454). In the present example, cross-beam (460) is substantially parallel with the outer surface of the eye (20). Rails (454) and cross-beam (460) cooperate to define a cannula insertion region (470), which is also substantially parallel with the outer surface of the eye in this example. As with other cannula guides described herein, cannula guide (450) of this example is configured to receive cannula (130) within this cannula insertion region (470) and thereby guide cannula (130) into the scleral incision (23), with rails (454) and cross-beam (460) cooperating to provide such guidance. When cannula (130) is disposed in cannula insertion region (470), cannula guide (450) is further configured to allow cannula (130) to slide along an insertion axis (IA); while also allowing the operator to adjust the orientation of cannula (130) to various insertion axes (IA) at various angles (θ) relative to a central axis (CA) of the incision (23). In some variations, cannula guide (450) may include an additional structure (e.g., a transparent structure) that helps maintain a substantially tangential orientation of cannula (130) along the eye (20) without compromising visualization of incision (23). Examples of such additional structures include web (316), described above; window member (610), described below; and film (1760), described below.

F. Cannula Guide with Rotating Ring

Figure 16:
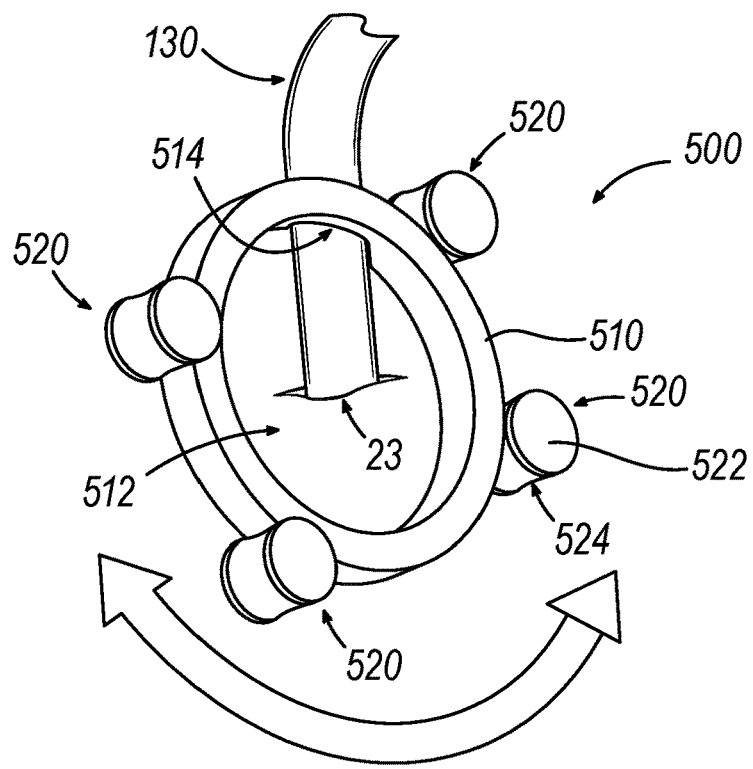
FIG. 16 depicts a perspective view of another example of a cannula guide, with the cannula guide guiding insertion of a cannula into an eye of a patient.

FIG. 16 shows another example of a cannula guide (500) guiding a cannula (130) into a scleral incision (23). Cannula guide (450) of this example includes an annular body (510) and a plurality of tacks (520). In some versions, annular body (510) is substantially rigid. Annular body (510) is secured to the eye (20) via tacks (520). Each tack (520) includes a head (522) defining a recess (524). Each tack (520) may further include a leg (not shown) with a sharp tip that is configured to penetrate the sclera (22) and thereby secure tack (520) to the sclera (22). Alternatively, tacks (520) may be secured to the eye (20) in any other suitable fashion. While four tacks (520) are shown in the present example, any other suitable number of tacks (520) may be used to secure annular body (510) to the eye (20). Heads (522) of tacks (520) are configured to substantially secure annular body (510) to the eye (20), while recesses (540) are configured to allow annular body (510) to rotate about the circular center of annular body (510), relative to the eye (20) and relative to tacks (520).

Annular body (510) of the present example defines an opening (514) that is configured to slidably receive cannula (130). Cannula guide (500) is configured and positioned to enable cannula (130) to enter the scleral incision (23) within a central region defined by annular body (510). As with other cannula guides described herein, cannula guide (500) of this example is configured to receive through opening (514) and thereby guide cannula (130) into the scleral incision (23), with annular body (510) providing such guidance. When cannula (130) is disposed in opening (514), cannula guide (500) is further configured to allow cannula (130) to slide along an insertion axis (IA); while also allowing the operator to adjust the orientation of cannula (130) to various insertion axes (IA) at various angles (θ) relative to a central axis (CA) of the incision (23). In this example, the insertion axis (IA) orientation is adjusted by rotating annular body (510) relative to the eye (20) and relative to tacks (520). Annular body (510) may be rotated about an axis that is substantially perpendicular to the outer surface of the eye (20) (e.g., along a radius of the eye). Similarly, annular body (510) may be rotated about a plane that is substantially parallel with the outer surface of the eye (20).

In some other versions, annular body (510) is not rotatable relative to the eye (20) and relative to tacks (520); and instead of having opening (514) annular body (510) defines an elongate slot that allows cannula (130) to achieve various insertion axes (IA) at various angles (θ) relative to a central axis (CA) of the incision (23).

G. Cannula Guide with Tongue

Figure 17:
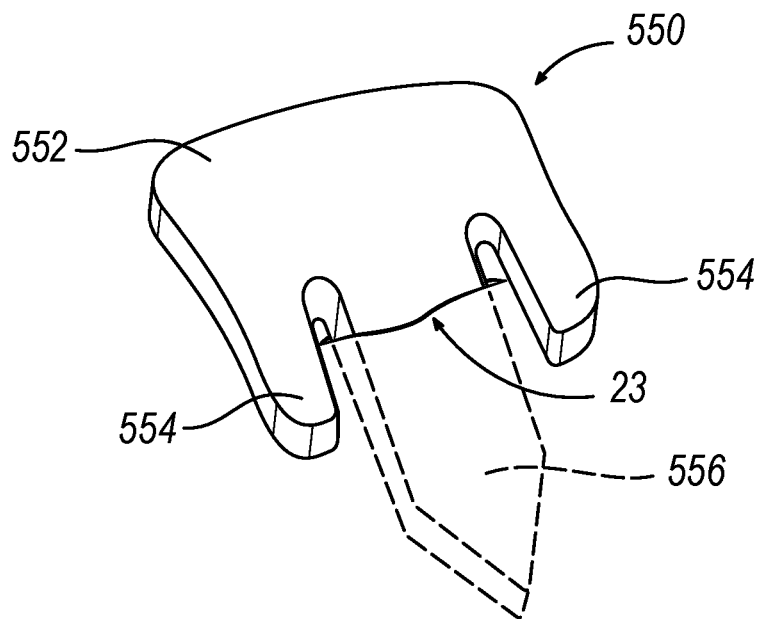
FIG. 17 depicts a perspective view of another example of a cannula guide, with the cannula guide inserted in an eye of a patient.

FIG. 17 shows another example of a cannula guide (550) that is configured to guide a cannula (130) into a scleral incision (23). Cannula guide (550) of this example includes a frame body (552) with a pair of feet (554) and a tongue (556). In some versions, frame body (552) is substantially rigid. Tongue (556) is configured to fit within scleral incision (23), such that tongue (556) may be disposed in the suprachoroidal space between the sclera (22) and the choroid (24). Feet (554) are configured to remain exterior to the sclera (554), flanking the incision (23). Tongue (556) and feet (554) may thus cooperate to secure cannula guide (550) to the eye (20) and stabilize cannula guide (550) relative to the eye (20) by providing mechanical grounding against opposite surfaces of the sclera (22) simultaneously. Further examples of cannula guides that provide similar interaction with opposing surfaces of the sclera (22) will be described in greater detail below. In some versions, tongue (556) extends along a first plane while feet (554) extend along a second plane that is offset from, yet parallel with, the first plane. The separation between these two planes may correspond with a thickness of the sclera (554), such that the dual engagement between tongue (556) and feet (554) with opposing sides of the sclera (22) does not impart undue trauma on the sclera (22).

Cannula guide (550) is configured to allow cannula (130) to freely enter incision (23), without imposing restrictions on the angle (θ) of the insertion axis (IA) relative to the central axis (CA) of the incision (23). In some versions, cannula (130) may be inserted into the incision (23) along the top surface of tongue (556), such that cannula (130) is interposed between tongue (556) and the sclera (22). In such scenarios, tongue (556) may prevent distal end (132) of cannula (130) from being driven directly into the choroid (24) by serving as a shield to the choroid (24) near the site of the incision (23). In some other versions, cannula (130) may be inserted into the incision (23) underneath the underside of tongue (556), such that tongue (556) is interposed between cannula (130) and the sclera (22). In such scenarios, tongue (556) may prevent distal end (132) of cannula (130) from skiving along the inner surface of the sclera (22) near the site of the incision (23). In either scenario, tongue (556) may assist in further guiding the inserted portion of cannula (130) along a path that is generally tangential to the choroid (24).

H. Cannula Guide with Rails and Window

Figure 18:
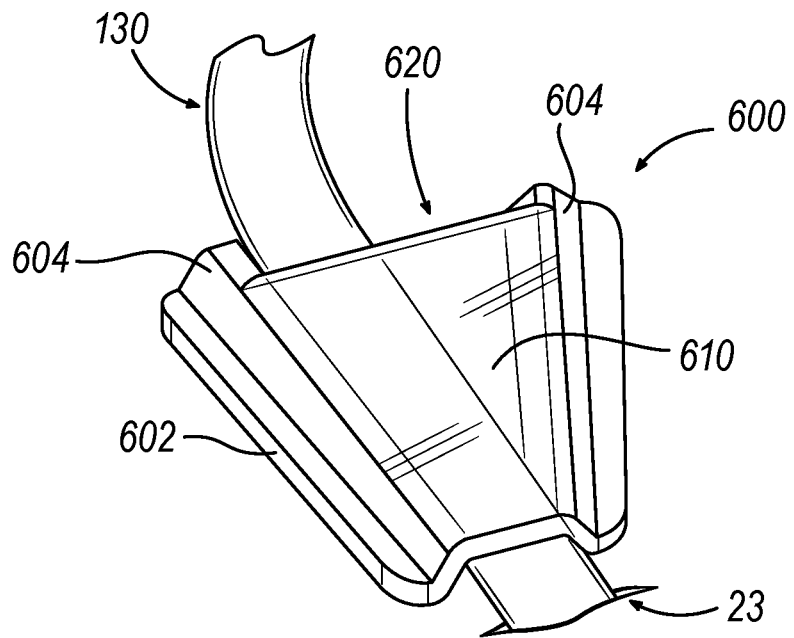
FIG. 18 depicts a perspective view of another example of a cannula guide, with the cannula guide guiding insertion of a cannula into an eye of a patient.

FIG. 18 shows another example of a cannula guide (600) guiding a cannula (130) into a scleral incision (23). Cannula guide (600) of this example includes a pair of frame bodies (602) and a window member (610) connecting frame bodies (602) together. Each frame body (602) includes a rail (604). In the present example, window member (610) connects frame bodies (602) via rails (604). In some versions, frame bodies (602) and window (610) are substantially rigid. Each frame body (602) may be secured to the eye (20) using any of the features or techniques described herein; or using any other features or techniques as may be apparent to those skilled in the art in view of the teachings herein. Frame bodies (602) together define a V shape in this example, such that frame bodies (602) together generally taper inwardly toward the incision (23).

Rails (604) extend generally perpendicularly away from the surface of the sclera (22) and follow the V-shaped profile of frame bodies (602), such that rails (604) convergingly taper toward the incision (23). Window member (610) extends transversely between rails (604) along the lengths of rails (604). Rails (604) and window member (610) cooperate to define a cannula insertion region (620). As with other cannula guides described herein, cannula guide (600) of this example is configured to receive cannula (130) within this cannula insertion region (620) and thereby guide cannula (130) into the scleral incision (23), with rails (604) and window member (610) cooperating to provide such guidance. When cannula (130) is disposed in cannula insertion region (620), cannula guide (600) is further configured to allow cannula (130) to slide along an insertion axis (IA); while also allowing the operator to adjust the orientation of cannula (130) to various insertion axes (IA) at various angles (θ) relative to a central axis (CA) of the incision (23). Window member (610) is transparent in this example, thereby facilitating visualization of distal end (132) of cannula (130) being oriented relative to the incision (23) and then entering the incision (23).

I. Cannula Guide with Arcuate Body and Wire

Figure 19:
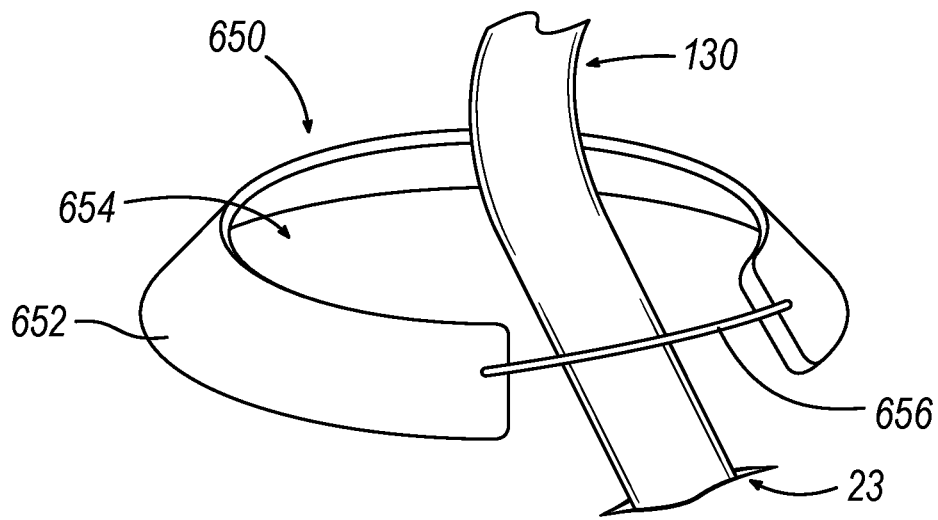
FIG. 19 depicts a perspective view of another example of a cannula guide, with the cannula guide guiding insertion of a cannula into an eye of a patient.

FIG. 19 shows another example of a cannula guide (650) guiding a cannula (130) into a scleral incision (23). Cannula guide (650) of this example includes an arcuate body (652) and a wire (656) secured between free ends of arcuate body (652). Arcuate body (652) is configured to encircle the limbus of the eye (20) in the present example and defines an inner taper or contour that is configured to complement the curvature of the limbus of the eye (20). In some versions, arcuate body (652) is substantially rigid. Arcuate body (652) may be secured to the eye (20) using any of the features or techniques described herein; or using any other features or techniques as may be apparent to those skilled in the art in view of the teachings herein.

In use, cannula guide (650) may be positioned in an offset manner relative to the scleral incision (23), with wire (656) being positioned near incision (23) as shown. Cannula (130) may then be advanced underneath wire (656) and into incision (23) to thereby enter the suprachoroidal space at a substantially tangential orientation. When cannula (130) is disposed in incision (23) in the manner shown in FIG. 19, cannula guide (650) is further configured to allow cannula (130) to slide along an insertion axis (IA); while also allowing the operator to adjust the orientation of cannula (130) to various insertion axes (IA) at various angles (θ) relative to a central axis (CA) of the incision (23).

J. Cannula Guides with Suction Fixation

Figure 20:
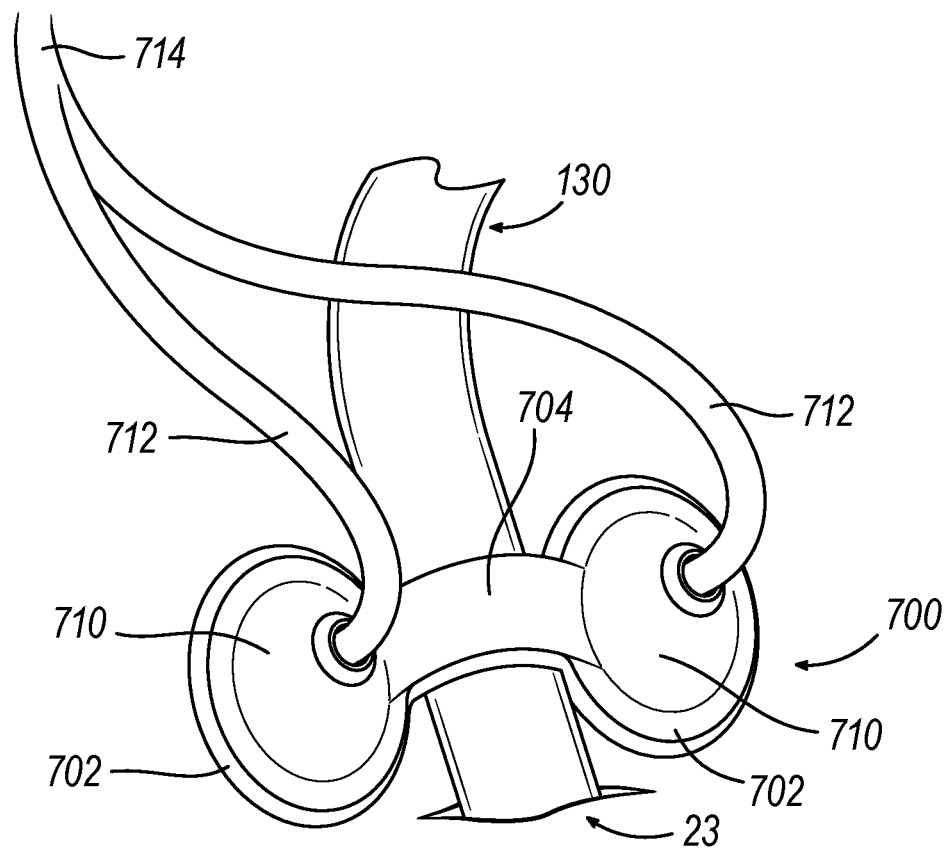
FIG. 20 depicts a perspective view of another example of a cannula guide, with the cannula guide guiding insertion of a cannula into an eye of a patient.
Figure 21:
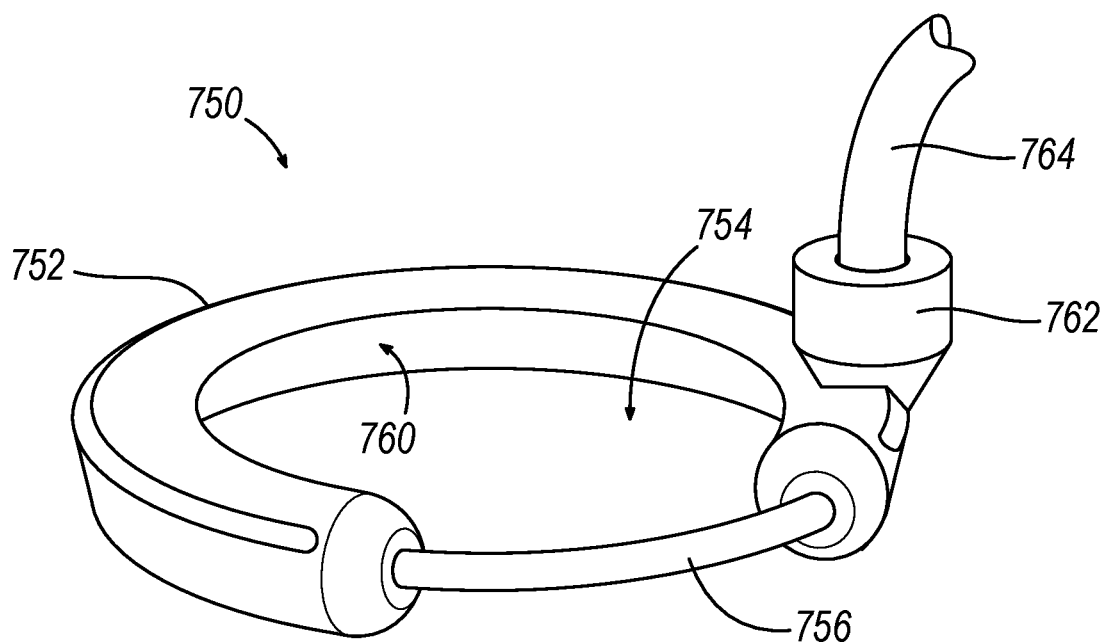
FIG. 21 depicts a perspective view of another example of a cannula guide.
Figure 22:
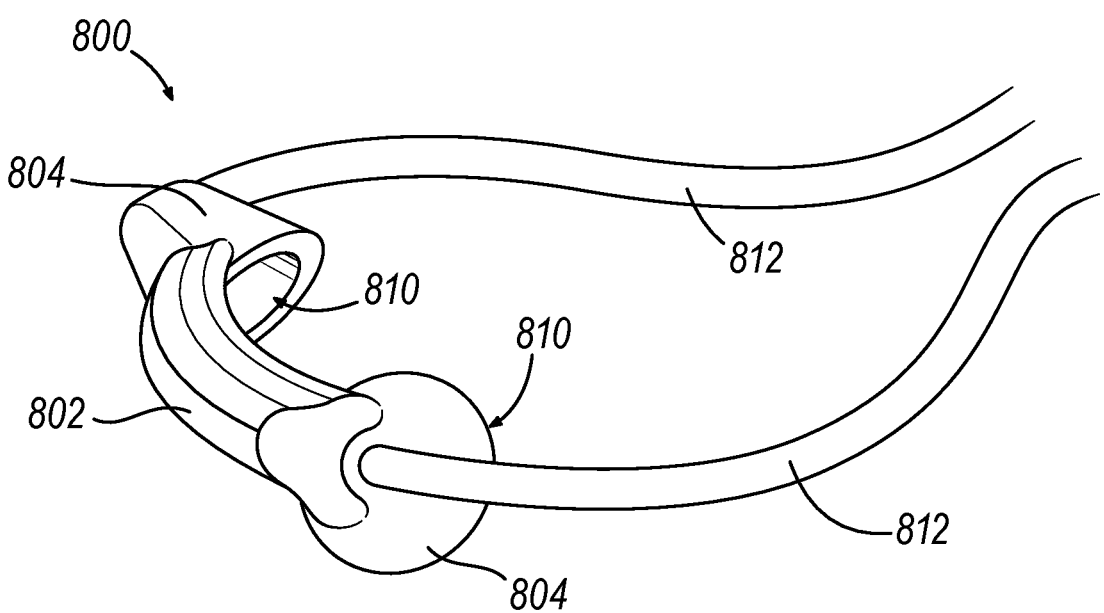
FIG. 22 depicts a perspective view of another example of a cannula guide.

FIGS. 20-22 show examples of cannula guides (700, 750, 800) that employ suction to secure cannula guides (700, 750, 800) to the eye (20). While suction is described as a securing technique in the context of cannula guides (700, 750, 800), suction may be used to secure any of the other cannula guides described herein to an eye (20). Those skilled in the art may recognize that the use of suction to secure a cannula guide to an eye (20) may result in minimal trauma to the eye (20). FIG. 20 shows a cannula guide (700) that includes a band (704) with suction cups (710) positioned at the terminal ends of band (704). Each suction cup (710) includes an eye engagement region (702) and defines a hollow interior region (not shown) that is configured to face the eye (20) when cannula guide (700) is mounted to the eye (20). A fluid conduit (712) extends from each suction cup (710). Each fluid conduit (712) is joined with a shared conduit (714), which is configured to further couple with a source of suction (not shown). Such a source of suction may include a syringe or any other suitable source of suction. When suction is applied to suction cups (710) via conduits (712, 714), this suction may further secure band (704) to the eye (20).

In use, cannula guide (700) may be positioned adjacent to the scleral incision (23), with band (704) being positioned near incision (23) as shown in FIG. 20, and with suction being applied to secure the position of cannula guide (700) on the eye (20). Cannula (130) may then be advanced underneath band (704) and into incision (23) to thereby enter the suprachoroidal space at a substantially tangential orientation. When cannula (130) is disposed in incision (23), cannula guide (700) is further configured to allow cannula (130) to slide along an insertion axis (IA); while also allowing the operator to adjust the orientation of cannula (130) to various insertion axes (IA) at various angles (θ) relative to a central axis (CA) of the incision (23).

Cannula guide (750) of FIG. 21 includes an arcuate body (752) and a band (756) secured between free ends of arcuate body (752). Cannula guide (700) of this example thus bears some structural resemblance to cannula guide (650) described above. Like arcuate body (652), arcuate body (752) of this example is configured to encircle the limbus of the eye (20). However, arcuate body (752) of this example differs from arcuate body (652) in that arcuate body (752) includes a recessed interior region (760) that is in fluid communication with a port (762). A conduit (764) is coupled with port (762) and is configured to further couple with a source of suction (not shown). When suction is applied to interior region (760) via conduit (764) and port (762), this suction may further secure arcuate body (752) to the eye (20).

In use, cannula guide (750) may be positioned in an offset manner relative to the scleral incision (23), with band (756) being positioned near incision (23), and with suction being applied to secure the position of cannula guide (750) on the eye (20). Cannula (130) may then be advanced underneath band (756) and into incision (23) to thereby enter the suprachoroidal space at a substantially tangential orientation. When cannula (130) is disposed in incision (23), cannula guide (750) is further configured to allow cannula (130) to slide along an insertion axis (IA); while also allowing the operator to adjust the orientation of cannula (130) to various insertion axes (IA) at various angles (θ) relative to a central axis (CA) of the incision (23).

FIG. 22 shows a cannula guide (800) that includes a band (802) with suction cups (804) positioned at the terminal ends of band (802). Each suction cup (804) defines a hollow interior region (810) that is configured to face the eye (20) when cannula guide (800) is mounted to the eye (20). A fluid conduit (812) extends from each suction cup (804). Each fluid conduit (812) is configured to further couple with a source of suction (not shown). When suction is applied to interior regions (810) via conduits (812), this suction may further secure band (802) to the eye (20).

In use, cannula guide (800) may be positioned adjacent to the scleral incision (23), with band (802) being positioned near incision (23), and with suction being applied to secure the position of cannula guide (800) on the eye (20). Cannula (130) may then be advanced underneath band (802) and into incision (23) to thereby enter the suprachoroidal space at a substantially tangential orientation. When cannula (130) is disposed in incision (23), cannula guide (800) is further configured to allow cannula (130) to slide along an insertion axis (IA); while also allowing the operator to adjust the orientation of cannula (130) to various insertion axes (IA) at various angles (θ) relative to a central axis (CA) of the incision (23).

K. Cannula Guides with Integral Securing Features

While some cannula guides are described herein as using separate tacks, a source of suction, or other features to secure the cannula guide to the eye (20), it may be desirable in some instances for the cannula guide to integrate its own feature or features that secure the cannula guide directly to the eye (20), such that additional features are not needed in order to secure the cannula guide to the eye. It may also be desirable for such securing features to only penetrate the sclera (22), such that the integral securing features of the cannula guide do not enter the choroid (24) or the vitreous region of the eye (20). Similarly, it may be desirable for such securing features to avoid a risk of damaging the lens of the eye (20). Examples of cannula guides (850, 900, 950, 1000, 1050, 1100) with integral securing features are described in greater detail below with reference to FIGS. 23-29.

Figure 23:
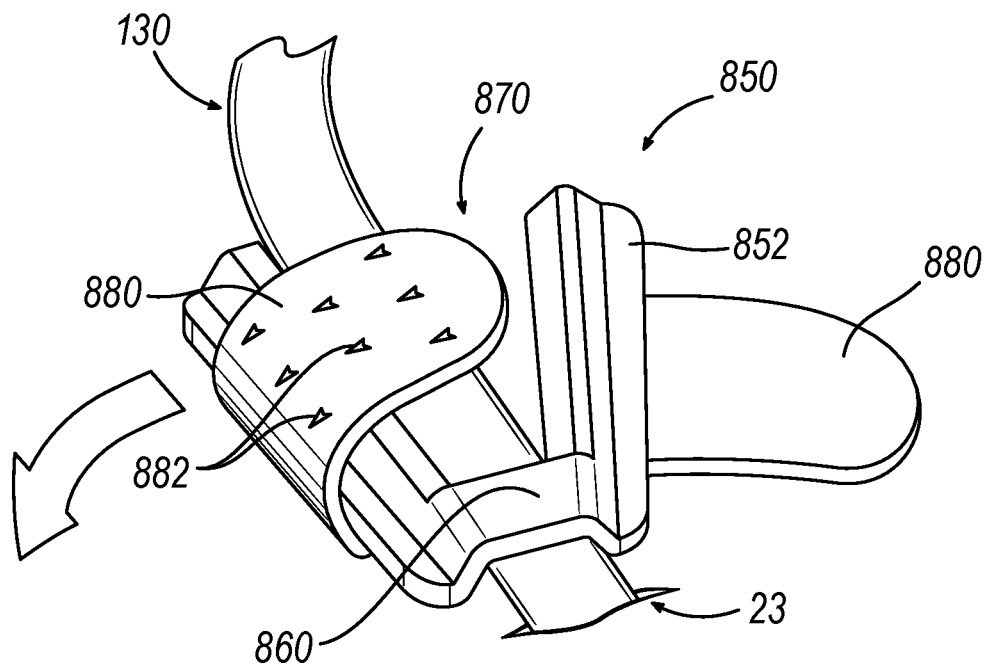
FIG. 23 depicts a perspective view of another example of a cannula guide, with the cannula guide guiding insertion of a cannula into an eye of a patient.

FIG. 23 shows a cannula guide (850) that includes a frame body (852) with a cross-beam (860) and a pair of securing straps (880). In some versions, frame body (852) is substantially rigid. Some versions of cannula guide (850) also include rails similar to rails (454) of cannula guide (450) descried above. Frame body (852) has a V shape in this example, such that frame body (852) generally tapers inwardly toward the scleral incision (23). Cross-beam (860)

extends across the narrow region defined by the taper of frame body (852). Frame body (852) and cross-beam (860) cooperate to define a cannula insertion region (870). As with other cannula guides described herein, cannula guide (850) of this example is configured to receive cannula (130) within this cannula insertion region (870) and thereby guide cannula (130) into the scleral incision (23), with frame body (852) and cross-beam (860) cooperating to provide such guidance. When cannula (130) is disposed in cannula insertion region (870), cannula guide (850) is further configured to allow cannula (130) to slide along an insertion axis (IA); while also allowing the operator to adjust the orientation of cannula (130) to various insertion axes (IA) at various angles (θ) relative to a central axis (CA) of the incision (23).

Securing straps (880) of the present example extend outwardly from opposite sides of frame body (852) and are in the form of flexible tabs. The underside of each securing strap (880) includes a plurality of traction features (882). By way of example only, traction features (882) may take the form of microteeth, spikes, barbs, hooks, or other configurations. Traction features (882) are configured to penetrate, or otherwise embed in, the sclera (22) of the eye (20). This may be accomplished by the operator pressing traction features (882) into the sclera (22). Once traction features (882) sufficiently penetrate the sclera (22) or are otherwise sufficiently embedded in the sclera (22), securing straps (880) effectively secure cannula guide (800) to the eye (20). In some versions, traction features (882) do not pass entirely through the full thickness of the sclera (22), such that traction features (882) do not penetrate the choroid (24) or otherwise reach the vitreous region of the eye (20). Once the procedure is complete, the operator may remove cannula guide (800) from the eye (20) by engaging securing straps (880) and peeling securing straps (880) away from the eye (20), thereby disengaging traction features (882) from the sclera (22).

Figure 24:
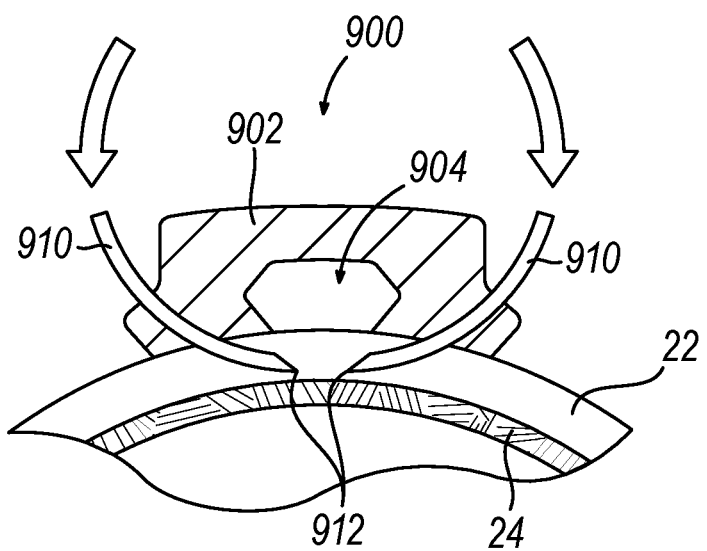
FIG. 24 depicts a cross-sectional view of another example of a cannula guide, with sliding fasteners of the cannula guide disposed in a sclera layer of an eye of a patient.

FIG. 24 shows a cannula guide (900) that includes a frame body (902) with a pair of securing legs (910). In some versions, frame body (902) is substantially rigid. Frame body (902) defines a cannula insertion region (904). As with other cannula guides described herein, cannula guide (900) of this example is configured to receive cannula (130) within this cannula insertion region (904) and thereby guide cannula (130) into scleral incision (23), with frame body (902) providing such guidance. When cannula (130) is disposed in cannula insertion region (904), cannula guide (900) is further configured to allow cannula (130) to slide along an insertion axis (IA); while also allowing the operator to adjust the orientation of cannula (130) to various insertion axes (IA) at various angles (θ) relative to a central axis (CA) of the incision (23).

Securing legs (910) of the present example are slidably disposed in frame body (902) and include sharp distal tips (912). Securing legs (910) are arcuately configured, with sharp distal tips (912) pointing generally toward each other. Securing legs (910) may be rigid, may be resilient, or may have other properties. Securing legs (910) are configured to transition between a first position and a second position. In the first position, securing legs (910) are positioned relative to frame body (902) such that sharp distal tips (912) do not protrude past the lower surface of frame body (902). In the second position, securing legs (910) are positioned relative to frame body (902) such that sharp distal tips (912) protrude below the lower surface of frame body (902), as shown in FIG. 24. In this position, securing legs (910) are embedded within the sclera (22), such that securing legs (910) secure cannula guide (900) to the eye (20).

In some scenarios, securing legs (910) are transitioned to this position by an operator pressing downwardly on the exposed free ends of securing legs (910), opposite to sharp distal tips (912). In some variations of cannula guide (900), cannula guide (900) includes integral actuator features that assist in driving securing legs (910) toward the position shown in FIG. 24. In addition, or in the alternative, an applier instrument may be used to drive securing legs (910) toward the position shown in FIG. 24. Regardless of how securing legs (910) are driven toward the position shown in FIG. 24, sharp distal tips (912) may penetrate the sclera (22) to thereby embed securing legs (910) within the sclera (22). As shown in FIG. 24, due to the arcuate configuration of securing legs (910), and arcuate path of travel of securing legs (910), securing legs (910) of the present example do not pass entirely through the full thickness of the sclera (22), such that securing legs (910) do not penetrate the choroid (24) or otherwise reach the vitreous region of the eye (20). In the present example, sharp distal tips (912) remain disposed in the sclera (22) while cannula guide (900) is secured to the eye (20); and while cannula guide (900) is used to guide cannula (130) into the scleral incision (23). In some other versions, sharp distal tips (912) may travel to a point where sharp distal tips (912) exit the sclera (22) and are positioned outside the eye (20) while an intermediate portion of each securing leg (910) remains disposed in the sclera (22) to secure cannula guide (900) to the eye (20).

Once the procedure is complete, the operator may remove cannula guide (900) from the eye (20) by engaging securing legs (910) and pulling securing legs (910) away from the eye (20), thereby disengaging securing legs (910) from the sclera (22). This may be accomplished by directly engaging the exposed free ends of securing legs (910), by manipulating an actuator on cannula guide (900), by using a separate instrument, or in any other suitable fashion.

Figure 25:
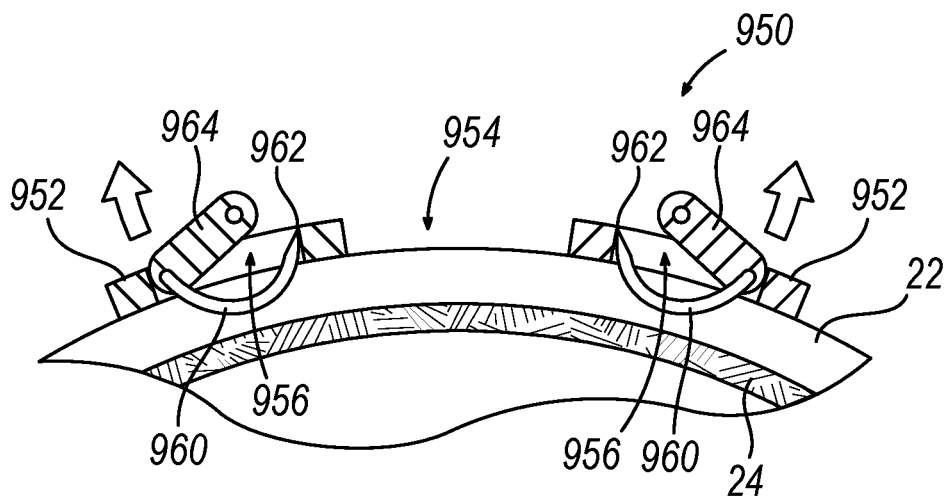
FIG. 25 depicts a cross-sectional view of another example of a cannula guide, with pivoting fasteners of the cannula guide disposed in a sclera layer of an eye of a patient.

FIG. 25 shows a cannula guide (950) that includes a frame body (952) with a pair of securing legs (960). In some versions, frame body (962) is substantially rigid. Frame body (962) defines a cannula insertion region (954). As with other cannula guides described herein, cannula guide (950) of this example is configured to receive cannula (130) within this cannula insertion region (954) and thereby guide cannula (130) into scleral incision (23), with frame body (952) providing such guidance. When cannula (130) is disposed in cannula insertion region (954), cannula guide (950) is further configured to allow cannula (130) to slide along an insertion axis (IA); while also allowing the operator to adjust the orientation of cannula (130) to various insertion axes (IA) at various angles (θ) relative to a central axis (CA) of the incision (23).

Securing legs (960) of the present example are pivotably coupled with frame body (952) via actuators (964). Each securing leg (960) includes a sharp distal tip (962). Securing legs (960) are arcuately configured, with sharp distal tips (962) pointing generally inwardly. Securing legs (960) may be rigid, may be resilient, or may have other properties. Securing legs (960) are configured to transition between a first position and a second position. In the first position, securing legs (960) are positioned relative to frame body (952) such that sharp distal tips (962) do not protrude past the lower surface of frame body (952). In the second position, securing legs (960) are positioned relative to frame body (952) such that sharp distal tips (962) protrude above the outer surface of the sclera (22), with intermediate regions of securing legs (960) being disposed within the sclera (22), as shown in FIG. 25. Frame body (952) defines openings (956) to receive sharp distal tips (9962) in this stage of operation. At this stage, securing legs (960) secure cannula guide (950) to the eye (20).

In some scenarios, securing legs (960) are transitioned to this position by an operator pressing downwardly on actuators (964). In some of these scenarios, an applier instrument may be used to engage actuators (964) to thereby drive securing legs (960) toward the position shown in FIG. 25. Regardless of how securing legs (960) are driven toward the position shown in FIG. 25, sharp distal tips (962) may penetrate the sclera (22) to thereby embed securing legs (960) within the sclera (22). As shown in FIG. 25, due to the arcuate configuration of securing legs (960), and arcuate path of travel of securing legs (960), securing legs (960) of the present example do not pass entirely through the full thickness of the sclera (22), such that securing legs (960) do not penetrate the choroid (24) or otherwise reach the vitreous region of the eye (20).

Once the procedure is complete, the operator may remove cannula guide (950) from the eye (20) by engaging actuators (964) and thereby pulling securing legs (960) away from the eye (20), thereby disengaging securing legs (960) from the sclera (22). This may be accomplished by directly engaging actuators (964), by using a separate instrument, or in any other suitable fashion.

Figure 26:
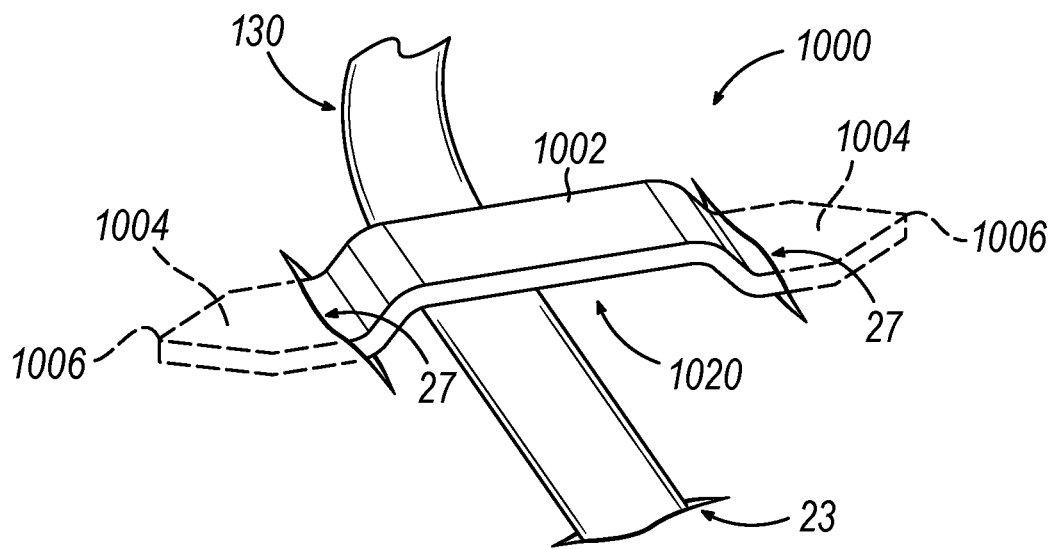
FIG. 26 depicts a perspective view of another example of a cannula guide, with the cannula guide guiding insertion of a cannula into an eye of a patient.

FIG. 26 shows another example of a cannula guide (1000) guiding a cannula (130) into a scleral incision (23). Cannula guide (1000) of this example includes an elongate body (1002) with a pair of free ends (1004). In some versions, body (1002) is resilient or otherwise flexible. Body (1002) is positioned to extend transversely relative to cannula (130) and is configured to span across a portion of the eye (20).

Each free end (1004) includes a penetrating tip (1006) that is configured to penetrate the sclera (22) at entry incisions (27), such that free ends (1004) are configured as blades. In some versions, penetrating tips (1006) have sufficient sharpness to form entry incisions (27). In some other versions, entry incisions (27) are formed separately (e.g., using a scalpel, etc.); and then free ends (1004) are inserted into the already formed entry incisions (27). In either case, free ends (1004) may be positioned within the sclera (22). Alternatively, free ends (1004) may pass through the sclera (22) and be positioned in the suprachoroidal space between the sclera (22) and the choroid (24). In either case, flexibility in frame body (1002) may enable frame body (1002) to deform to thereby enable free ends (1004) to enter incisions (27); and resilience in frame body (1002) may then urge frame body (1002) to return to the configuration shown in FIG. 26 to thereby maintain the position of free ends (1004) in incisions (27).

Elongate body (1002) and free ends (1004) are configured such that an intermediate region of elongate body (1002) between free ends (1004) will stand off from the surface of the sclera (22), thereby defining a cannula insertion region (1020) in a space between elongate body (1002) and the sclera (22). In some versions, elongate body (1002) extends along a first plane while free ends (1004) extend along a second plane that is parallel with, yet offset from, the first plane. When cannula (130) is disposed in cannula insertion region (1020), cannula guide (1000) is further configured to allow cannula (130) to slide along an insertion axis (IA); while also allowing the operator to adjust the orientation of cannula (130) to various insertion axes (IA) at various angles (θ) relative to a central axis (CA) of the incision (23).

Figure 27:
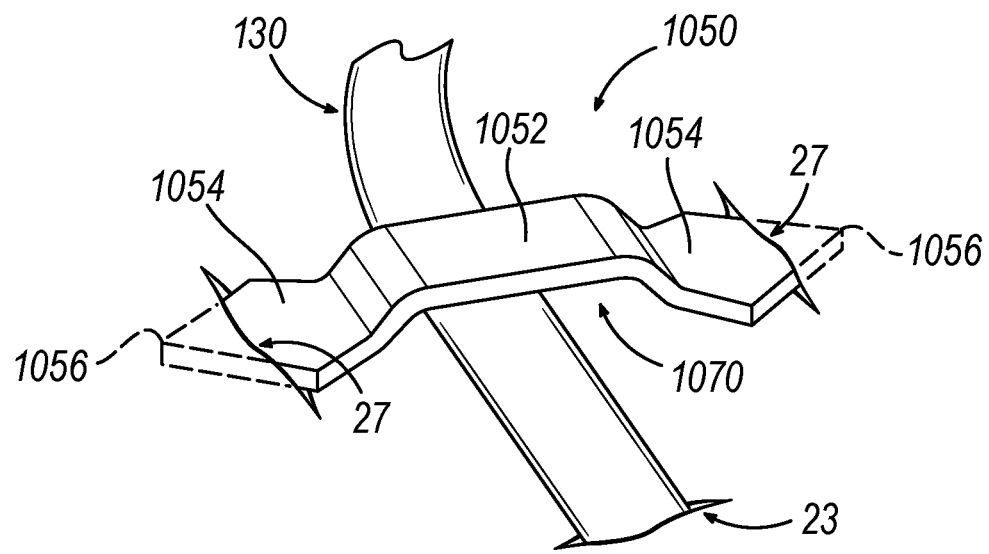
FIG. 27 depicts a perspective view of another example of a cannula guide, with the cannula guide guiding insertion of a cannula into an eye of a patient.

In the example of cannula guide (1000) shown in FIG. 26, the lateral width of elongate body (1002) is substantially the same along the length of elongate body (1002), such that cannula guide (1000) only arrows at free ends (1004) to form penetrating tips (1006). Some variations of cannula guide (1000) may include a version of elongate body (1002) whose width narrows between free ends (1004). FIG. 27 shows an example of such a variation. Cannula guide (1050) of this example includes an elongate body (1052) with a pair of free ends (1054). In some versions, Body (1050) is resilient or otherwise flexible. Body (1052) is positioned to extend transversely relative to cannula (130) and is configured to span across a portion of the eye (20).

Each free end (1054) includes a penetrating tip (1056) that is configured to penetrate the sclera (22) at entry incisions (27), such that free ends (1054) are configured as blades. In some versions, penetrating tips (1056) have sufficient sharpness to form entry incisions (27). In some other versions, entry incisions (27) are formed separately (e.g., using a scalpel, etc.); and then free ends (1054) are inserted into the already formed entry incisions (27). In either case, free ends (1054) may be positioned within the sclera (22). Alternatively, free ends (1054) may pass through the sclera (22) and be positioned in the suprachoroidal space between the sclera (22) and the choroid (24). In either case, flexibility in frame body (1052) may enable frame body (1052) to deform to thereby enable free ends (1054) to enter incisions (27); and resilience in frame body (1052) may then urge frame body (1052) to return to the configuration shown in FIG. 27 to thereby maintain the position of free ends (1054) in incisions (27).

Elongate body (1052) and free ends (1054) are configured such that an intermediate region of elongate body (1052) between free ends (1054) will stand off from the surface of the sclera (22), thereby defining a cannula insertion region (1070) in a space between elongate body (1052) and the sclera (22). In some versions, elongate body (1052) extends along a first plane while free ends (1054) extend along a second plane that is parallel with, yet offset from, the first plane. When cannula (130) is disposed in cannula insertion region (1070), cannula guide (1050) is further configured to allow cannula (130) to slide along an insertion axis (IA); while also allowing the operator to adjust the orientation of cannula (130) to various insertion axes (IA) at various angles (θ) relative to a central axis (CA) of the incision (23). In the present example, the lateral width of elongate body (1052) narrows between free ends (1054). This narrowed lateral width may provide a relatively larger range of angles (θ) for insertion axes (IA) relative to a central axis (CA) of the incision (23), as compared with the range of angles (θ) permitted by a cannula guide (1000) whose elongate body (1050) lateral width does not narrow between free ends (1004).

Figure 28:
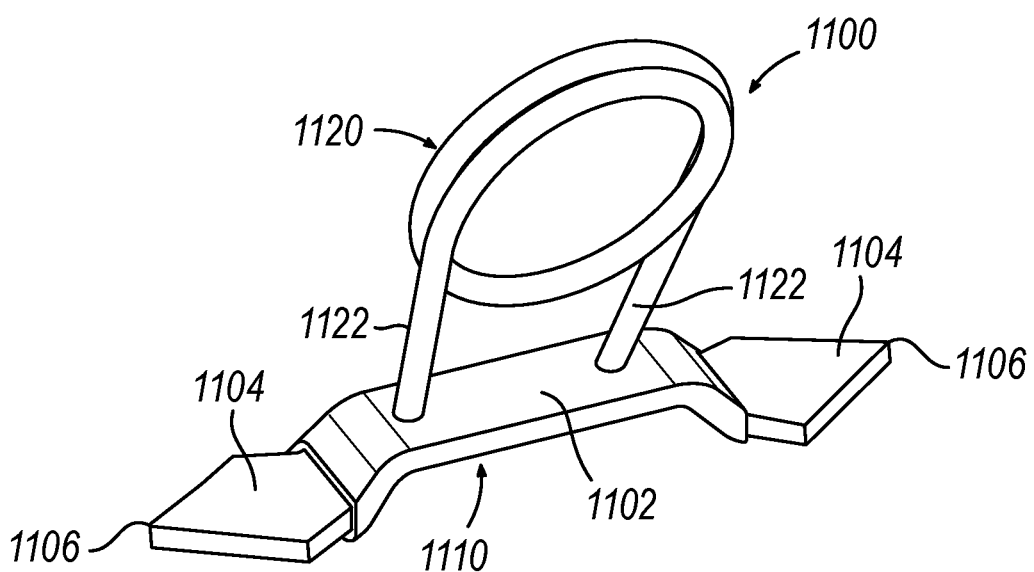
FIG. 28 depicts a perspective view of another example of a cannula guide.
Figure 29:
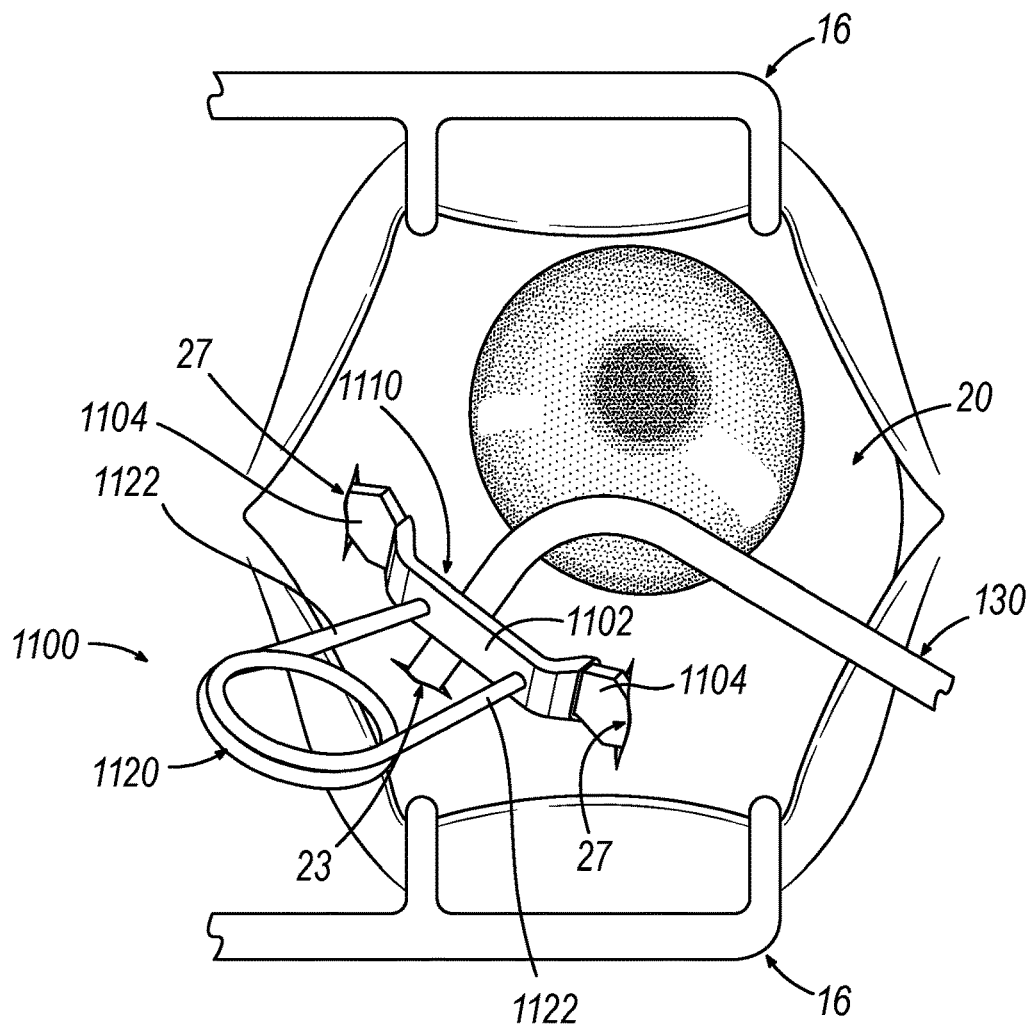
FIG. 29 depicts a perspective view of the cannula guide of FIG. 28, with the cannula guide guiding insertion of a cannula into an eye of a patient.

FIGS. 28-29 show another example of a cannula guide (1100) with integral securing features, with the addition of a resilient feature that further promotes engagement between those integral securing features and the eye (20). Cannula guide (1100) of this example includes a strap (1110), a pair of free ends (1104) having sharp tips (1106) such that free ends (1104) are configured as blades, a pair of arms (1122), and a torsion spring (1120). In the present example, arms (1122) and torsion spring (1120) are unitarily formed of the same piece of material. In some versions, free ends (1104) are also unitarily formed with arms (1112), such that free ends (1104) are joined with arms (1112) under strap (1110). In such versions, portions of arms (1112) pass through corresponding openings formed in strap (1110). In some other versions, free ends (1104) are secured to respective ends of strap (1110), and arms (1122) are also secured to strap (1110).

Strap (1110) may be formed of a flexible material. In some versions, strap (1110) is non-extensible. In the present example, torsion spring (1120) is configured to resiliently bias free ends (1104) outwardly away from each other; while strap (1110) is configured to restrict the distance to which free ends (1104) may be separated apart from each other. To install cannula guide (1100) on an eye (20) of the patient as shown in FIG. 29, the operator may grasp cannula guide (1100) by arms (1112) and pinch arms (1112) toward each other to thereby reduce the distance between free ends (1104), then position free ends (1104) at corresponding entry incisions (27), then release arms (1112). When arms (1112) are released, torsion spring (1120) may resiliently urge free ends (1104) outwardly, thereby urging free ends (1104) into entry incisions (27). In some versions, penetrating tips (1106) have sufficient sharpness to form entry incisions (27). In some other versions, entry incisions (27) are formed separately (e.g., using a scalpel, etc.); and then free ends (1104) are inserted into the already formed entry incisions (27). In either case, free ends (1104) may be positioned within the sclera (22). Alternatively, free ends (1104) may pass through the sclera (22) and be positioned in the suprachoroidal space between the sclera (22) and the choroid (24). In either case, flexibility in torsion spring (1120) and strap (1110) may enable torsion spring (1120) and strap (1110) to deform to thereby enable free ends (1104) to enter incisions (27); and resilience in torsion spring (1120) may then urge cannula guide (1100) to return to the configuration shown in FIG. 29 to thereby maintain the position of free ends (1104) in incisions (27).

Strap (1110) of the present example also defines a cannula insertion region (1110). As with other cannula guides described herein, cannula guide (1100) of this example is configured to receive cannula (130) within this cannula insertion region (1110) and thereby guide cannula (130) into the scleral incision (23), with strap (1110) providing such guidance. When cannula (130) is disposed in cannula insertion region (1110), cannula guide (1100) is further configured to allow cannula (130) to slide along an insertion axis (IA); while also allowing the operator to adjust the orientation of cannula (130) to various insertion axes (IA) at various angles (θ) relative to a central axis (CA) of the incision (23).

L. Cannula Guide with Suture Receiving Features

Figure 30:
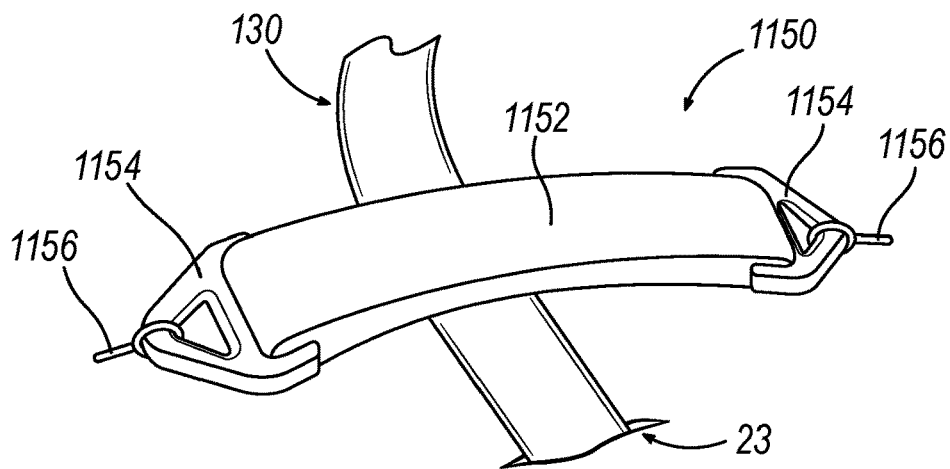
FIG. 30 depicts a perspective view of another example of a cannula guide, with the cannula guide guiding insertion of a cannula into an eye of a patient.

As noted above, it may be desirable to avoid requiring the operator to form a suture loop assembly (70) that, by itself, is configured to appropriately guide cannula (130) into a scleral incision (23). Despite this, it may be acceptable to have a cannula guide that is secured to the eye (20) by sutures. Such suturing may be relatively simple compared to the suturing required to form a suture loop assembly (70) as described above. FIG. 30 shows an example of a cannula guide (1150) that may be secured to an eye (20) via sutures (1156). Cannula guide (1150) of this example includes a strap (1152) that is configured to span across a portion of the eye (20), with suture receiving features (1154) at each end of strap (1152). In some versions, suture receiving features (1154) are formed of a rigid material while strap (1152) is formed of a flexible material. With strap (1152) positioned appropriately in relation to a scleral incision (23), sutures (1156) may be fed through suture receiving features (1154) and secured to the eye (20). Suture receiving features (1154) are thus configured to serve as anchoring features for cannula guide (1150). In some versions, sutures (1156) are stitched directly to the sclera (22) using conventional stitching techniques. In some such versions, sutures (1156) do not pass fully through the sclera (22). In some other versions, sutures (1156) do pass fully through the sclera (22) and reach the suprachoroidal space.

In some versions, strap (1152) is formed of an elastic material or is otherwise longitudinally extensible. In some such versions, an operator may install cannula guide (1150) on the eye (20) by first positioning cannula guide (1150) on the eye and applying a suture (1156) to the eye (20) through one suture receiving feature (1154). The operator may then pull the other end of cannula guide (1150) to thereby stretch strap (1152) to an appropriate degree; and while holding strap (1152) in tension, apply a suture (1156) to the eye (20) through the other suture receiving feature (1154). Sutures (1156) may thus hold strap (1152) in tension against the eye (20). In some other versions, strap (1152) is not elastic or otherwise longitudinally extensible. In such versions, strap (1152) may still have a degree of flexibility.

As with other cannula guides described herein, cannula guide (1150) of this example is configured to receive cannula (130) in the region between strap (1152) and the sclera (22); and thereby guide cannula (130) into scleral incision (23), with strap (1152) providing such guidance. When cannula (130) is disposed in this region between strap (1152) and the sclera (22), cannula guide (1100) is further configured to allow cannula (130) to slide along an insertion axis (IA); while also allowing the operator to adjust the orientation of cannula (130) to various insertion axes (IA) at various angles (θ) relative to a central axis (CA) of the incision (23).

M. Cannula Guide with Deployment Instrument Integrating Tacks

Figure 31:
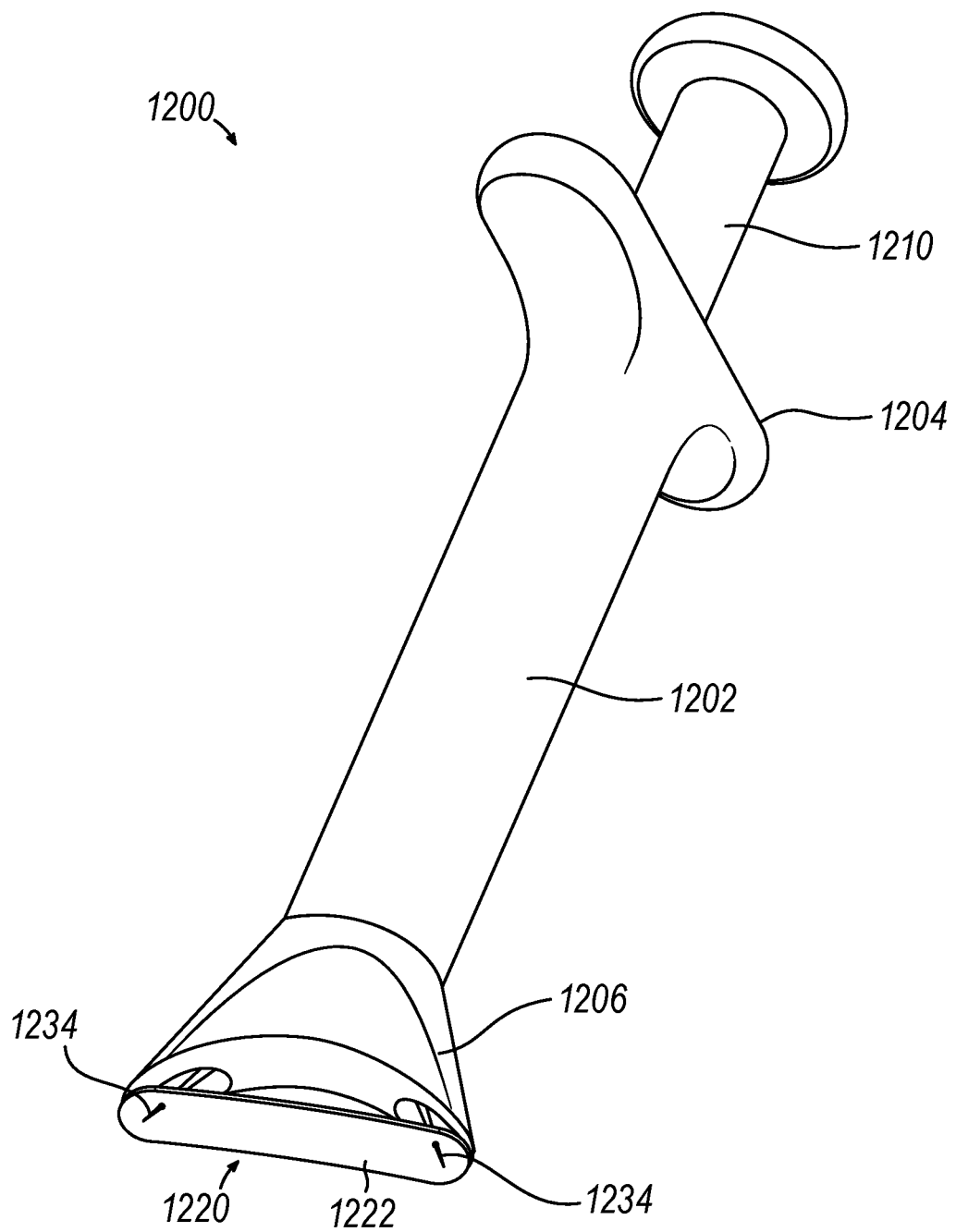
FIG. 31 depicts a perspective view of an example of a cannula guide assembly including a cannula guide and a guide deployer instrument.
Figure 32:
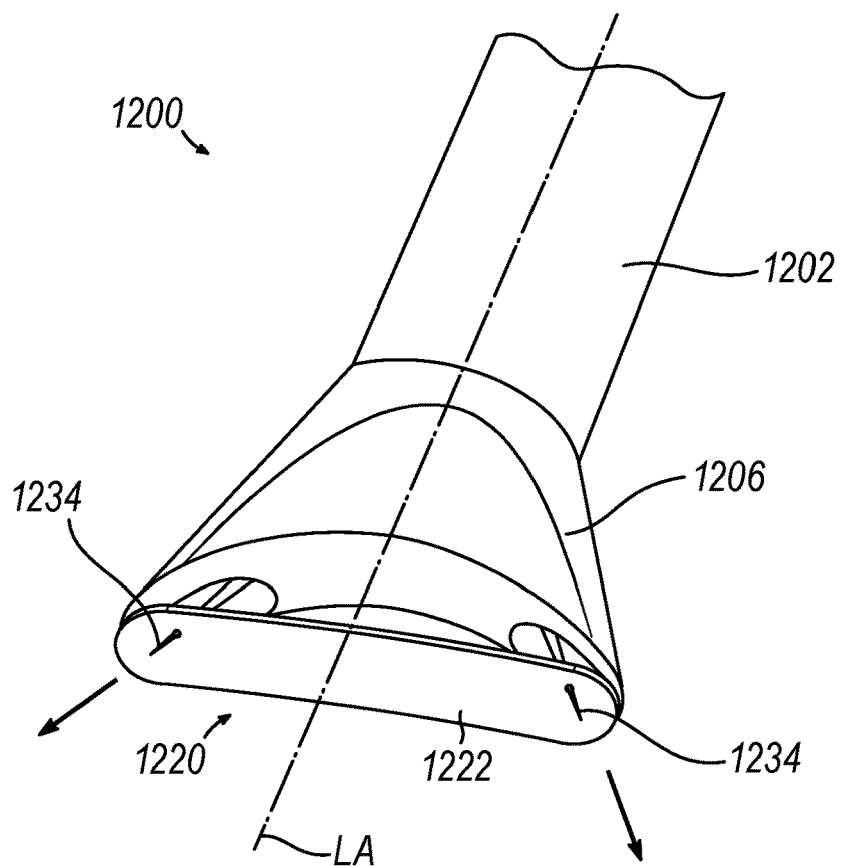
FIG. 32 depicts an enlarged perspective view of a distal portion of the guide deployer instrument and cannula guide of FIG. 31.
Figure 33:
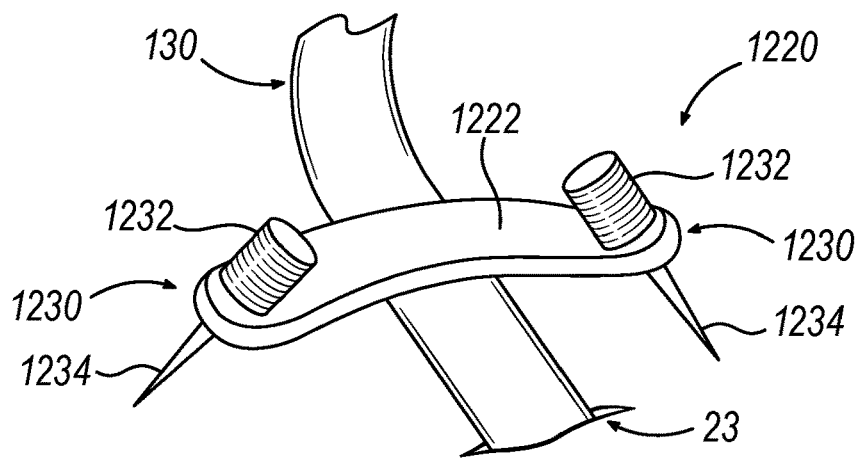
FIG. 33 depicts a perspective view of the cannula guide of FIG. 31, with the cannula guide guiding insertion of a cannula into an eye of a patient.

As noted herein, a cannula guide may be installed on an eye (20) of a patient using a cannula guide deployment instrument. In some scenarios, such a deployment instrument may further integrate fasteners that are used to secure the cannula guide to the eye (20). FIGS. 31-33 show an example of such an arrangement. In this example, a cannula guide deployment instrument (1200) includes a shaft (1202) having a proximal end (1204) defining a hilt and a distal end (1206) that is configured to receive tacks (1230) and a cannula guide (1220). An actuator (1210) is slidably coupled with shaft (1202) and is operable to translate longitudinally relative to shaft (1202) to thereby deploy tacks (1230) and cannula guide (1220). As best seen in FIG. 32, tacks (1230) are loaded in distal end (1206) in a manner such that tacks (1230) are oriented outwardly relative to a central longitudinal axis (LA) of shaft (1202). As also best seen in FIG. 32, cannula guide (1220) is preloaded on tacks (1230) such that pins (1234) of tacks (1230) partially extend through cannula guide (1220). Cannula guide (1220) of the present example is in the form of a strap (1222) that is configured to span across a portion of the eye (20). Strap (1222) may be flexible; and may further be extensible or non-extensible.

To deploy cannula guide (1220) and tacks (1230), the operator may position distal end (1206) at the appropriate position on the eye (20) and then urge actuator (1210) distally relative to shaft (1202). This will drive tacks (1230) distally along paths that are obliquely oriented relative to the central longitudinal axis (LA) of shaft (1202), ultimately driving pins (1234) into the sclera (22) as shown in FIG. 23. Pins (1234) have sharp tips in this example, such that pins (1234) penetrate the sclera (22). With pins (1234) advanced into the sclera (22), strap (1222) is captured between heads (1232) of tacks (1230) and the sclera (22), such that tacks (1230) secure strap (1222) to the eye (20). In some versions, pins (1234) do not pass completely through the sclera (22), such that pins (1234) do not reach the suprachoroidal space or the vitreous region of the eye (20). In other versions, pins (1234) reach the suprachoroidal space or the vitreous region of the eye (20). In either scenario, it should be understood that deployment instrument (1200) may be utilized to carry cannula guide (1220) to position; and to install cannula guide (1220) on the eye (20) with a pair of tacks (1230) with just a single press of a single actuator (1210), thereby simplifying the installation process for cannula guide (1220).

As with other cannula guides described herein, cannula guide (1220) of this example is configured to receive cannula (130) in the region between strap (1222) and the sclera (22); and thereby guide cannula (130) into scleral incision (23), with strap (1222) providing such guidance. When cannula (130) is disposed in this region between strap (1222) and the sclera (22), cannula guide (1220) is further configured to allow cannula (130) to slide along an insertion axis (IA); while also allowing the operator to adjust the orientation of cannula (130) to various insertion axes (IA) at various angles (θ) relative to a central axis (CA) of the incision (23).

Figure 34:
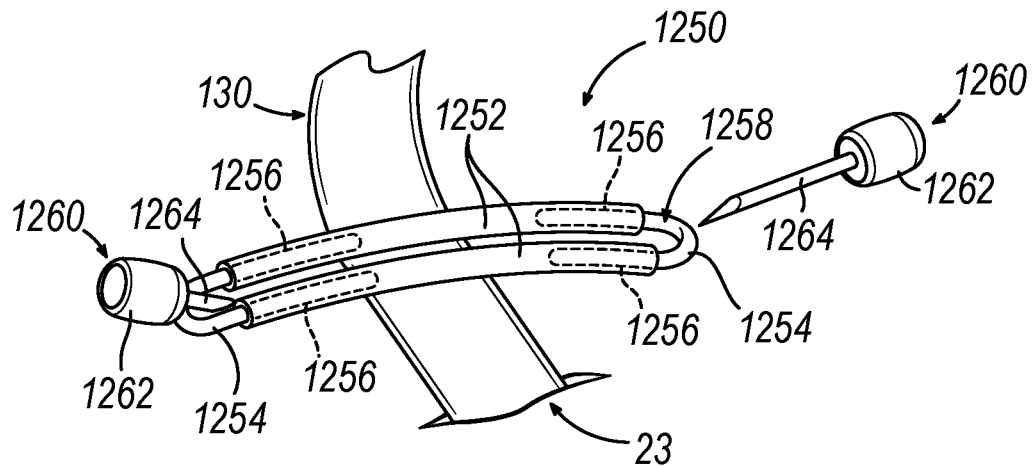
FIG. 34 depicts a perspective view of another example of a cannula guide, with the cannula guide guiding insertion of a cannula into an eye of a patient.

FIG. 34 shows another example of a cannula guide (1250) that utilizes tacks (1260) to secure cannula guide (1250) to the eye (20). In some versions, deployment instrument (1200) is modified to integrate and deploy cannula guide (1250) and tacks (1260). Alternatively, cannula guide (1250) and tacks (1260) may be deployed using any other suitable kind of instrumentation or techniques. Cannula guide (1250) of this example includes a pair of elongate members (1252) that are laterally offset from each other and parallel to each other. Elongate members (1252) are configured to span across a portion of the eye (20). A U-shaped wire (1254) is positioned at the end of each elongate member (1252). Each U-shaped wire (1254) includes one portion (1256) that is fixedly disposed within one elongate member (1252) and another portion (1256) that is fixedly disposed within the other elongate member (1252). The portions of U-shaped wires (1254) that are exposed relative to elongate members (1252) define pin-receiving regions (1258). These pin-receiving regions (1258) are configured to receive pins (1264) of tacks (1260). U-shaped wires (1234) are thus configured to serve as anchoring features for cannula guide (1250).

Tacks (1260) may be used to secure cannula guide (1250) to the eye (20) by driving tacks (1260) distally into the eye (20) when cannula guide (1250) is appropriately positioned in relation to a scleral incision (23). While tacks (1260) are oriented inwardly, toward each other, in the example shown in FIG. 34, tacks (1260) may alternatively be oriented outwardly, away from each other, when deployed in the eye (20) (e.g., similar to the arrangement shown in FIG. 33). Pins (1264) have sharp tips in this example, such that pins (1264) penetrate the sclera (22). With pins (1264) advanced into the sclera (22), U-shaped wires (1254) are captured between heads (1262) of tacks (1260) and the sclera (22), such that tacks (1260) secure cannula guide (1250) to the eye (20). In some versions, pins (1264) do not pass completely through the sclera (22), such that pins (1264) do not reach the suprachoroidal space or the vitreous region of the eye (20). In other versions, pins (1264) reach the suprachoroidal space or the vitreous region of the eye (20).

In some versions, elongate members (1252) are formed of an elastic material or are otherwise longitudinally extensible. In some such versions, an operator may install cannula guide (1250) on the eye (20) by first positioning cannula guide (1250) on the eye and driving one tack (1260) into the eye (20) through one pin-receiving region (1258). The operator may then pull the other end of cannula guide (1250) to thereby stretch elongate members (1252) to an appropriate degree; and while holding elongate members (1252) in tension, drive the other tack (1260) into the eye (20) through the other pin-receiving region (1258). Tacks (1260) may thus hold elongate members (1252) in tension against the eye (20). In some other versions, elongate members (1252) are not elastic or otherwise longitudinally extensible. In such versions, elongate members (1252) may still have a degree of flexibility.

As with other cannula guides described herein, cannula guide (1250) of this example is configured to receive cannula (130) in the region between elongate members (1252) and the sclera (22); and thereby guide cannula (130) into scleral incision (23), with elongate members (1252) providing such guidance. When cannula (130) is disposed in this region between elongate members (1252) and the sclera (22), cannula guide (1250) is further configured to allow cannula (130) to slide along an insertion axis (IA); while also allowing the operator to adjust the orientation of cannula (130) to various insertion axes (IA) at various angles (θ) relative to a central axis (CA) of the incision (23).

Figure 35:
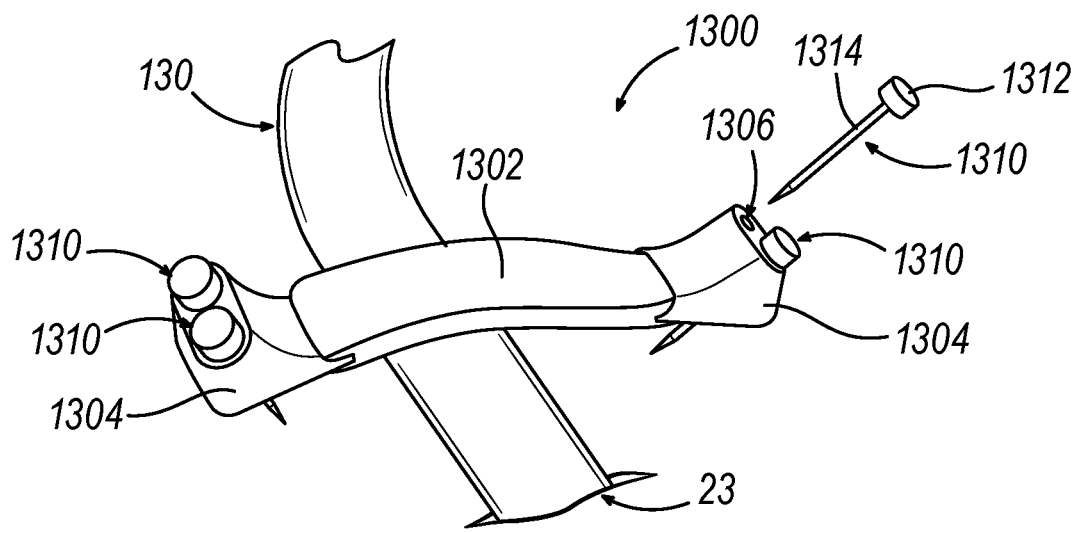
FIG. 35 depicts a perspective view of another example of a cannula guide, with the cannula guide guiding insertion of a cannula into an eye of a patient.

FIG. 35 shows another example of a cannula guide (1300) that utilizes tacks (1310) to secure cannula guide (1300) to the eye (20). In some versions, deployment instrument (1200) is modified to integrate and deploy cannula guide (1300) and tacks (1310). Alternatively, cannula guide (1300) and tacks (1310) may be deployed using any other suitable kind of instrumentation or techniques. Cannula guide (1300) of this example includes a strap (1302) that is configured to span across a portion of the eye (20), with a pair of anchoring features (1304) fixedly secured to each end of strap (1302). In some versions, strap (1302) is flexible; and may be extensible or non-extensible. Anchoring features (1304) may be rigid. Each anchoring feature (1304) defines a pair of openings (1306), with each opening (1306) being sized to slidably receive a pin (1314) of a corresponding tack (1310). Cannula guide (1300) is configured to include four tacks (1310) in the present example, though other versions may include more or fewer than four tacks (1310).

Tacks (1310) may be used to secure cannula guide (1300) to the eye (20) by driving tacks (1310) distally into the eye (20) when cannula guide (1300) is appropriately positioned in relation to a scleral incision (23). While tacks (1310) are oriented inwardly, toward each other, in the example shown in FIG. 35, tacks (1310) may alternatively be oriented outwardly, away from each other, when deployed in the eye (20) (e.g., similar to the arrangement shown in FIG. 33). Pins (1314) have sharp tips in this example, such that pins (1314) penetrate the sclera (22). With pins (1314) advanced into the sclera (22) via openings (1306), anchoring features (1304) are captured between heads (1312) of tacks (1310) and the sclera (22), such that tacks (1310) secure cannula guide (1300) to the eye (20). In some versions, pins (1314) do not pass completely through the sclera (22), such that pins (1314) do not reach the suprachoroidal space or the vitreous region of the eye (20). In other versions, pins (1314) reach the suprachoroidal space or the vitreous region of the eye (20).

In some versions, strap (1302) is formed of an elastic material or is otherwise longitudinally extensible. In some such versions, an operator may install cannula guide (1300) on the eye (20) by first positioning cannula guide (1300) on the eye and driving tacks (1310) into the eye (20) through one anchoring feature (1304). The operator may then pull the other end of cannula guide (1300) to thereby stretch strap (1302) to an appropriate degree; and while holding strap (1302) in tension, drive tacks (1310) into the eye (20)

through the other anchoring feature (1304). Tacks (1310) may thus hold strap (1302) in tension against the eye (20). In some other versions, strap (1302) is not elastic or otherwise longitudinally extensible. In such versions, strap (1302) may still have a degree of flexibility.

As with other cannula guides described herein, cannula guide (1300) of this example is configured to receive cannula (130) in the region between strap (1302) and the sclera (22); and thereby guide cannula (130) into scleral incision (23), with strap (1302) providing such guidance. When cannula (130) is disposed in this region between strap (1302) and the sclera (22), cannula guide (1300) is further configured to allow cannula (130) to slide along an insertion axis (IA); while also allowing the operator to adjust the orientation of cannula (130) to various insertion axes (IA) at various angles (θ) relative to a central axis (CA) of the incision (23).

N. Cannula Guide with Integral Inwardly-Oriented Securing Features

Figure 36:
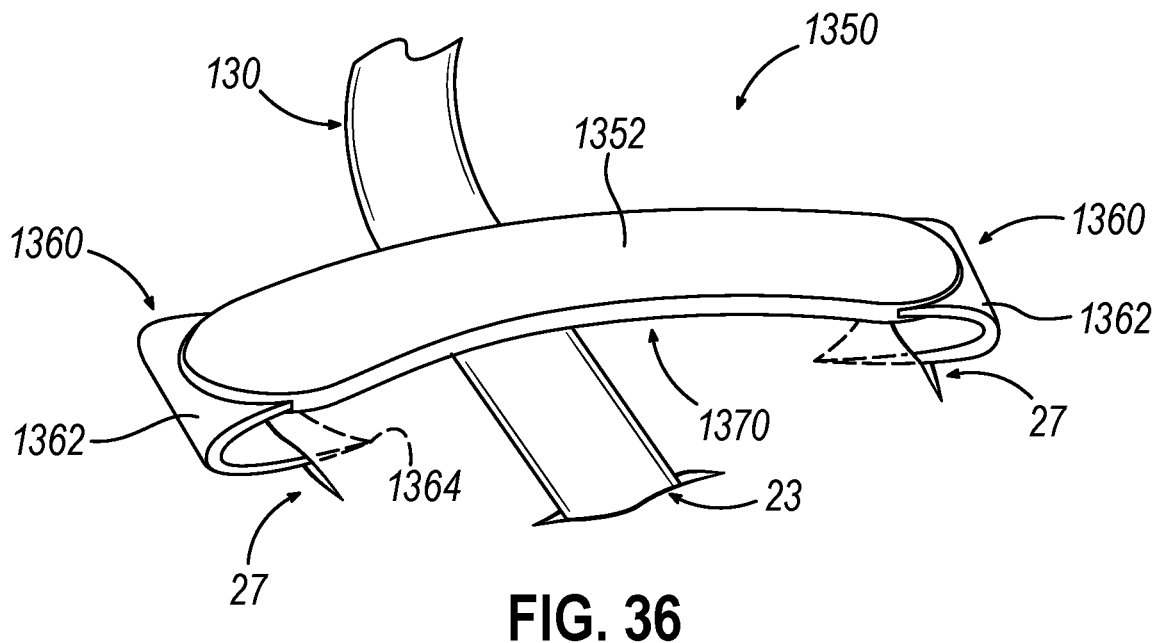
FIG. 36 depicts a perspective view of another example of a cannula guide, with the cannula guide guiding insertion of a cannula into an eye of a patient.
Figure 37:
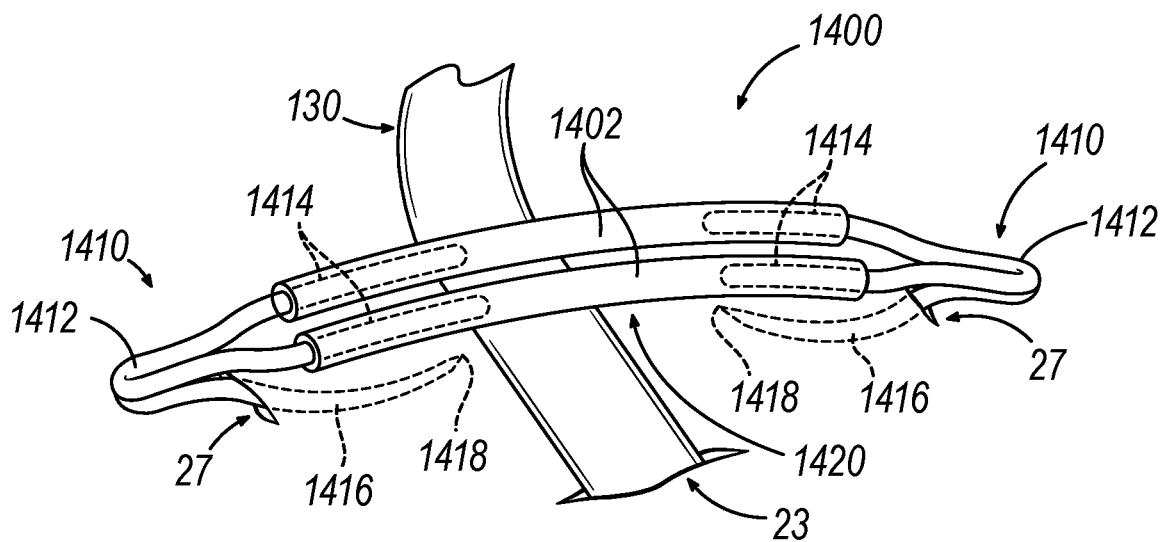
FIG. 37 depicts a perspective view of another example of a cannula guide, with the cannula guide guiding insertion of a cannula into an eye of a patient.

As noted above, it may be desirable to provide a cannula guide that integrates its own feature or features that secure the cannula guide directly to the eye (20), such that additional features are not needed in order to secure the cannula guide to the eye. While several examples of such cannula guides have already been discussed herein, it may be further desirable for the integral securing features to be oriented inwardly, toward each other; rather than such integral securing features being oriented outwardly, away from each other. By way of example only, such an inward orientation may make it easier to accommodate the curvature of the eye (20), reducing the risk of such integral securing features accidentally exiting outwardly through the sclera (22). FIGS. 36-37 show examples of cannula guides (1350, 1400) with integral, inwardly oriented securing features.

Cannula guide (1350) shown in FIG. 36 includes a strap (1352) that is configured to span across a portion of the eye (20), with a pair of anchoring members (1360) secured to the ends of strap (1352). Each anchoring member (1360) includes a body (1362) with a sharp tip (1364). Each body (1362) has a bent configuration, such that each body (1362) initially extends outwardly from strap (1352), then bends inwardly such that sharp tips (1364) are oriented inwardly toward each other. Each sharp tip (1364) is configured to penetrate the sclera (22) at entry incisions (27). In some versions, sharp tips (1364) have sufficient sharpness to form entry incisions (27). In some other versions, entry incisions (27) are formed separately (e.g., using a scalpel, etc.); and then sharp tips (1364) are inserted into the already formed entry incisions (27). In either case, sharp tips (1364) may be positioned within the sclera (22). Alternatively, sharp tips (1364) may pass through the sclera (22) and be positioned in the suprachoroidal space between the sclera (22) and the choroid (24).

In some versions, strap (1352) is formed of an elastic material or is otherwise longitudinally extensible. In some such versions, an operator may install cannula guide (1350) on the eye (20) by first positioning cannula guide (1350) on the eye and driving one anchoring feature (1360) into the eye (20). The operator may then pull the other end of cannula guide (1350) to thereby stretch strap (1352) to an appropriate degree; and while holding strap (1352) in tension, drive the other anchoring feature (1360) into the eye (20). Anchoring features (1360) may thus hold strap (1352) in tension against the eye (20). In some other versions, strap (1352) is not elastic or otherwise longitudinally extensible. In such versions, strap (1352) may still have a degree of flexibility. In either case, flexibility in strap (1352) may enable strap (1352) to deform to thereby enable sharp tips (1364) to enter incisions (27). In versions where strap (1352) is elastic or resilient, such elasticity or resilience in strap (1352) may urge strap (1352) toward the configuration shown in FIG. 36 to thereby maintain the position of sharp tips (1364) in incisions (27).

In some versions, strap (1352) and anchoring members (1360) are configured such that strap (1352) will stand off from the surface of the sclera (22), thereby defining a cannula insertion region (1370) in a space between strap (1352) and the sclera (22). Alternatively, strap (1352) may be stretched away from the sclera (22) to define cannula insertion region (1370). In some versions, strap (1352) extends along a first plane while sharp tips (1364) extend along a second plane that is parallel with, yet offset from, the first plane. When cannula (130) is disposed in cannula insertion region (1370), cannula guide (1350) is further configured to allow cannula (130) to slide along an insertion axis (IA); while also allowing the operator to adjust the orientation of cannula (130) to various insertion axes (IA) at various angles (θ) relative to a central axis (CA) of the incision (23).

Cannula guide (1400) shown in FIG. 37 includes a pair of elongate members (1402) that are configured to span across a portion of the eye (20), with a pair of anchoring members (1410) secured to the ends of elongate members (1402). Each anchoring member (1410) includes a junction portion (1412), a pair of mounting portions (1414), and a pin portion (1416). Each anchoring member (1410) includes one mounting portion (1414) that is fixedly secured within one elongate member (1402) and another mounting portion (1414) that is fixedly secured within the other elongate member (1402). Mounting portions (1414) of each anchoring member (1410) are joined together at the junction portion (1412) of the corresponding anchoring member (1410). Each pin portion (1416) is also joined with the junction portion (1412) of the corresponding anchoring member (1410). Each pin portion (1412) includes a sharp tip (1418). Anchoring members (1410) of the present example are configured such that each pin portion (1412) extends along a corresponding arc; and such that sharp tips (1418) are generally oriented inwardly toward each other. With the arced curvature of pin portions (1412) in the present example, sharp tips (1418) are also generally oriented toward elongate members (1402).

Each sharp tip (1418) is configured to penetrate the sclera (22). In some versions, sharp tips (1418) have sufficient sharpness to pierce the sclera (22) without requiring an initial incision to be separately formed. In some other versions, entry incisions (27) are formed separately (e.g., using a scalpel, etc.); and then sharp tips (1418) are inserted into the already formed entry incisions (27). In either case, pin portions (1412) may be positioned within the sclera (22). Alternatively, pin portions (1412) may pass through the sclera (22) and be positioned in the suprachoroidal space between the sclera (22) and the choroid (24). In either case, flexibility in elongate members (1402) may enable elongate members (1402) to deform to thereby enable pin portions (1412) to enter the sclera (22); and resilience in elongate members (1402) may then urge elongate members (1402) to return to the configuration shown in FIG. 37 to thereby maintain the position of pin portions (1412) in the sclera (22).

In some versions, elongate members (1402) are formed of an elastic material or are otherwise longitudinally extensible. In some such versions, an operator may install cannula guide (1400) on the eye (20) by first positioning cannula guide (1400) on the eye and driving one anchoring member (1410) into the eye (20). The operator may then pull the other end of cannula guide (1400) to thereby stretch elongate members (1402) to an appropriate degree; and while holding elongate members (1402) in tension, drive the other anchoring member (1410) into the eye (20). Anchoring members (1410) may thus hold elongate members (1402) in tension against the eye (20). In some other versions, elongate members (1402) are not elastic or otherwise longitudinally extensible. In such versions, elongate members (1402) may still have a degree of flexibility. In either case, flexibility in elongate members (1402) may enable elongate members (1402) to deform to thereby enable anchoring members (1410) to enter the eye (20). In versions where elongate members (1402) are elastic or resilient, such elasticity or resilience in elongate members (1402) may urge elongate members (1402) toward the configuration shown in FIG. 37 to thereby maintain the position of anchoring members (1410) in the eye (20).

In some versions, elongate members (1402) and anchoring members (1410) are configured such elongate members (1402) will stand off from the surface of the sclera (22), thereby defining a cannula insertion region (1420) in a space between elongate members (1402) and the sclera (22). Alternatively, elongate members (1402) may be stretched away from the sclera (22) to define cannula insertion region (1420). In either case, when cannula (130) is disposed in cannula insertion region (1420), cannula guide (1400) is further configured to allow cannula (130) to slide along an insertion axis (IA); while also allowing the operator to adjust the orientation of cannula (130) to various insertion axes (IA) at various angles (θ) relative to a central axis (CA) of the incision (23).

O. Cannula Guide with Integral Positioning and Grasping Feature

Figure 38:
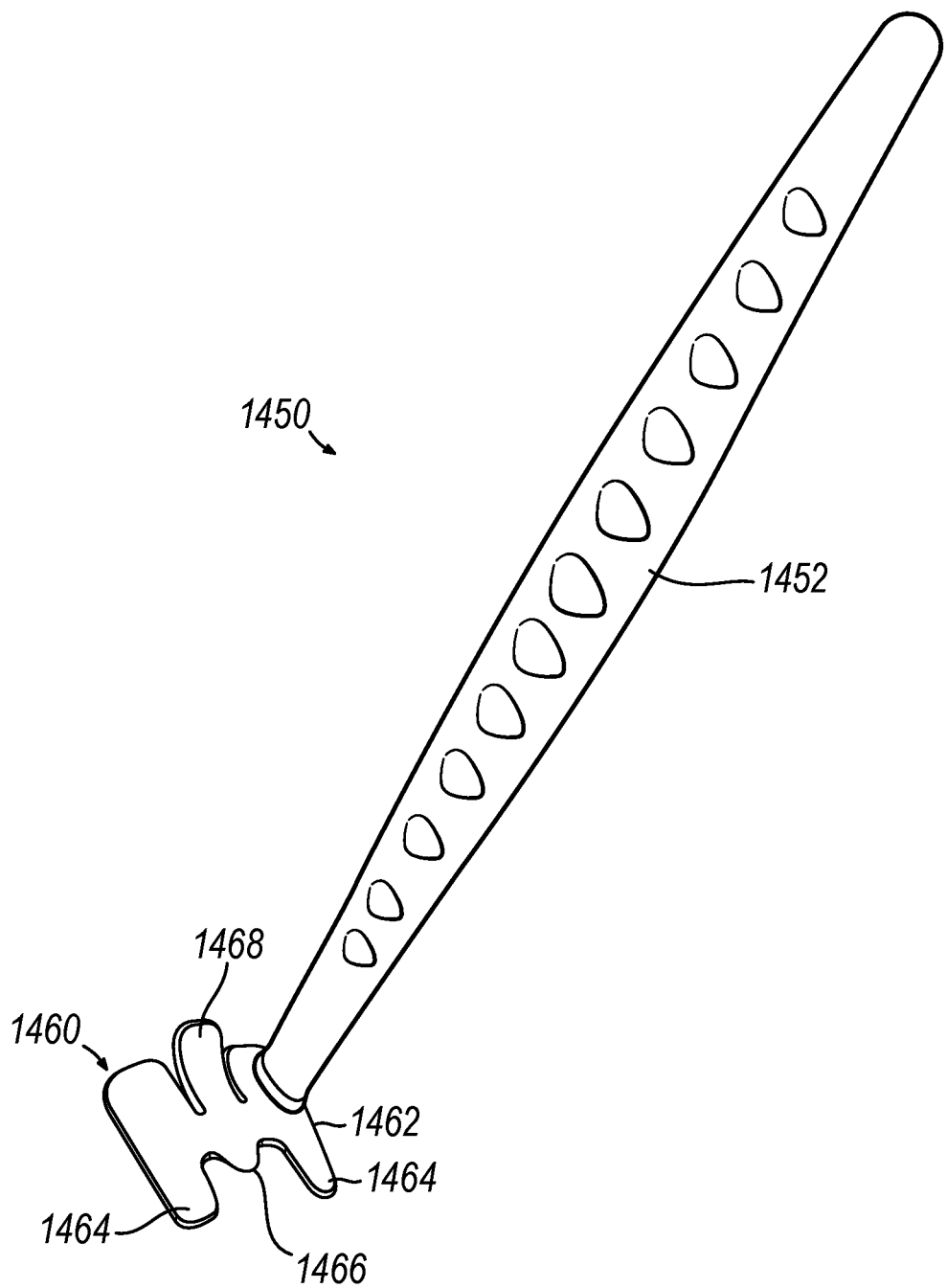
FIG. 38 depicts a perspective view of another example of a cannula guide.
Figure 39:
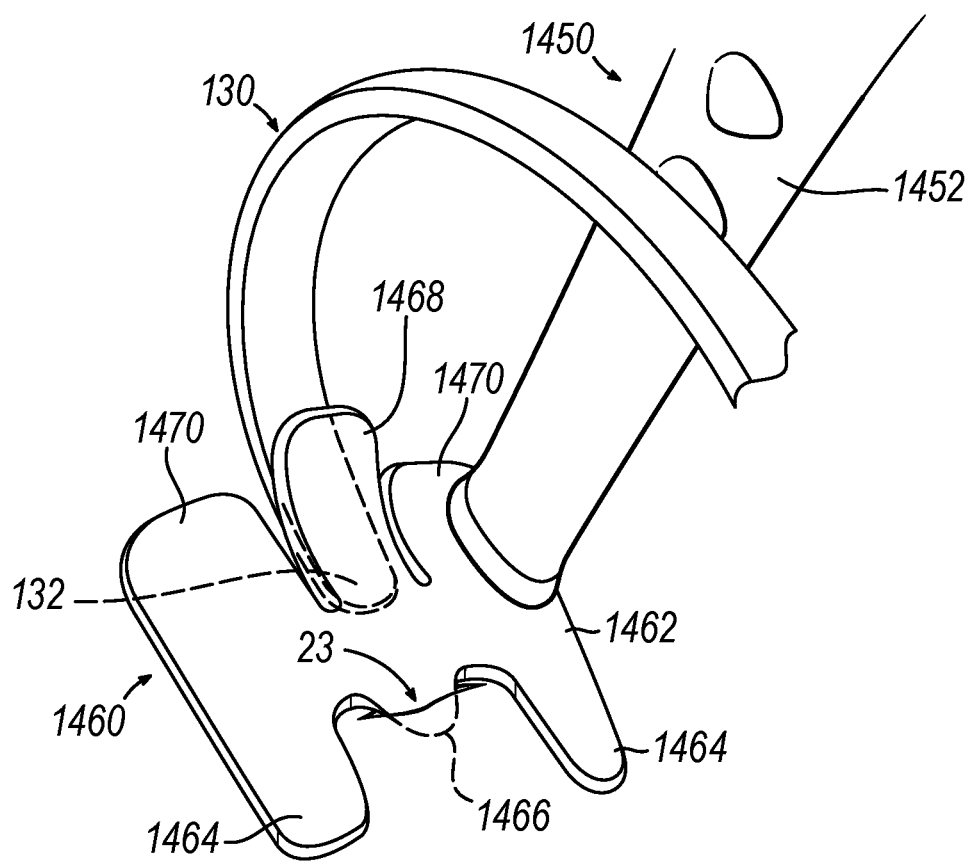
FIG. 39 depicts a perspective view of a distal portion of the cannula guide of FIG. 38, with the cannula guide guiding insertion of a cannula into an eye of a patient.

In some scenarios, it may be desirable for the operator to effectively maintain a grasp on a cannula guide after initially positioning the cannula guide on the eye (20), such that the operator may continue effectively grasping the cannula guide as cannula (130) is being advanced into the eye (20) via the cannula guide. To that end, it may be desirable to include a cannula guide that includes an integral grasping feature. FIGS. 38-39 show an example of such a cannula guide (1450). In this example, cannula guide (1450) includes a guiding portion (1460) and a grasping portion (1452). Grasping portion (1452) is in the form of an elongate shaft or handle that may be grasped by the operator during positioning and use of cannula guide (1450) to guide cannula (130) into a scleral incision (23).

Guiding portion (1460) is positioned at the distal end of grasping portion (1452) and is fixedly secured to grasping portion (1452). Guiding portion (1460) of this example includes a body (1462) with a pair of feet (1464), a tongue (1466), a central guide tab (1468), and a pair of lateral guide tabs (1470). Tongue (1466) and feet (1464) are positioned along the same side of body (1462), with tongue (1466) being laterally positioned between feet (1464). In the present example, tongue (1466) has a shorter length than feet (1464), though this configuration may be varied. Tongue (1466) may be coplanar with feet (1464). Alternatively, tongue (1466) may be positioned along a first plane while feet (1464) are positioned along a second plane that is offset from the first plane. In some such versions, the first and second planes are parallel with each other.

Central guide tab (1468) and lateral guide tabs (1470) extend from the other side of body (1462), such that guide tabs (1468, 1470) are on the side of body (1462) that is opposite to tongue (1466) and feet (1464). Central guide tab (1468) is laterally interposed between lateral guide tabs (1470). Central guide tab (1468) extends along a curve that is oriented away from body (1462). Guide tab (1468) curves away from body (1462) in the same general direction in which grasping portion (1452) extends away from body (1462). The width of guide tab (1468) may vary substantially from the width shown in FIGS. 38-39, permitting any desired range of freedom for the operator to adjust the orientation of cannula (130) to various insertion axes (IA) at various angles (θ) relative to a central axis (CA) of the incision (23). In the present example, grasping portion (1452), guide tab (1468), tongue (1466), feet (1444), and the rest of body (1462) are substantially rigid. In other variations, some or all of these features may be resilient or otherwise flexible.

During use, the operator may grasp grasping portion (1452) and position guiding portion (1460) adjacent to a scleral incision (23). The operator may then manipulate grasping portion (1452) to insert tongue (1466) into the scleral incision (23) as shown in FIG. 39. In this state, tongue (1466) is positioned at the inner surface of the sclera (22) (i.e., adjacent to the choroid (24)) while feet (1464) are positioned at the outer surface of the sclera (22). By effectively capturing the sclera (22) between tongue (1466) and feet (1464), guiding portion (1460) may be effectively secured to, and mechanically grounded relative to, the eye (20). The operator may then advance cannula (130) underneath central guide tab (1468) as shown in FIG. 39, such that cannula (130) is fed underneath body (1462) and into the scleral incision (23). During this insertion, central guide tab (1468) may guide cannula (130) along a first dimension (e.g., a vertical dimension) while lateral guide tabs (1470) may guide cannula (130) along a second dimension (e.g., a horizontal dimension). As cannula (130) enters the suprachoroidal space between the sclera (22) and the choroid (23), cannula (130) passes underneath tongue (1466). When cannula (130) is disposed in the suprachoroidal space, guiding portion (1460) is further configured to allow cannula (130) to slide along an insertion axis (IA); while also allowing the operator to adjust the orientation of cannula (130) to various insertion axes (IA) at various angles (θ) relative to a central axis (CA) of the incision (23).

In some scenarios, the operator may hold cannula guide (1450) in position (e.g., as shown in FIG. 39) throughout use of cannula (130) to deliver fluids or other substances to the eye (20), including during repositioning of cannula (130) for delivery to two or more sites within the eye (20) as described above. In some other scenarios, the operator may hold cannula guide (1450) in position (e.g., as shown in FIG. 39) only during initial insertion of cannula (130) into the eye (20); and then remove cannula guide (1450) from the eye (20). With cannula guide (1450) removed, and with cannula (130) still suitably inserted into the eye (20), the operator may then use cannula (130) to deliver fluids or other substances to the eye (20), including repositioning of cannula (130) for delivery to two or more sites within the eye (20) as described above. In other words, after removal of cannula guide (1450) from the eye (20), the operator may adjust the orientation of cannula (130) to various insertion axes (IA) at various angles (θ) relative to a central axis (CA) of the incision (23).

P. Cannula Guide with Removable Deployment Instrument

Figure 40:
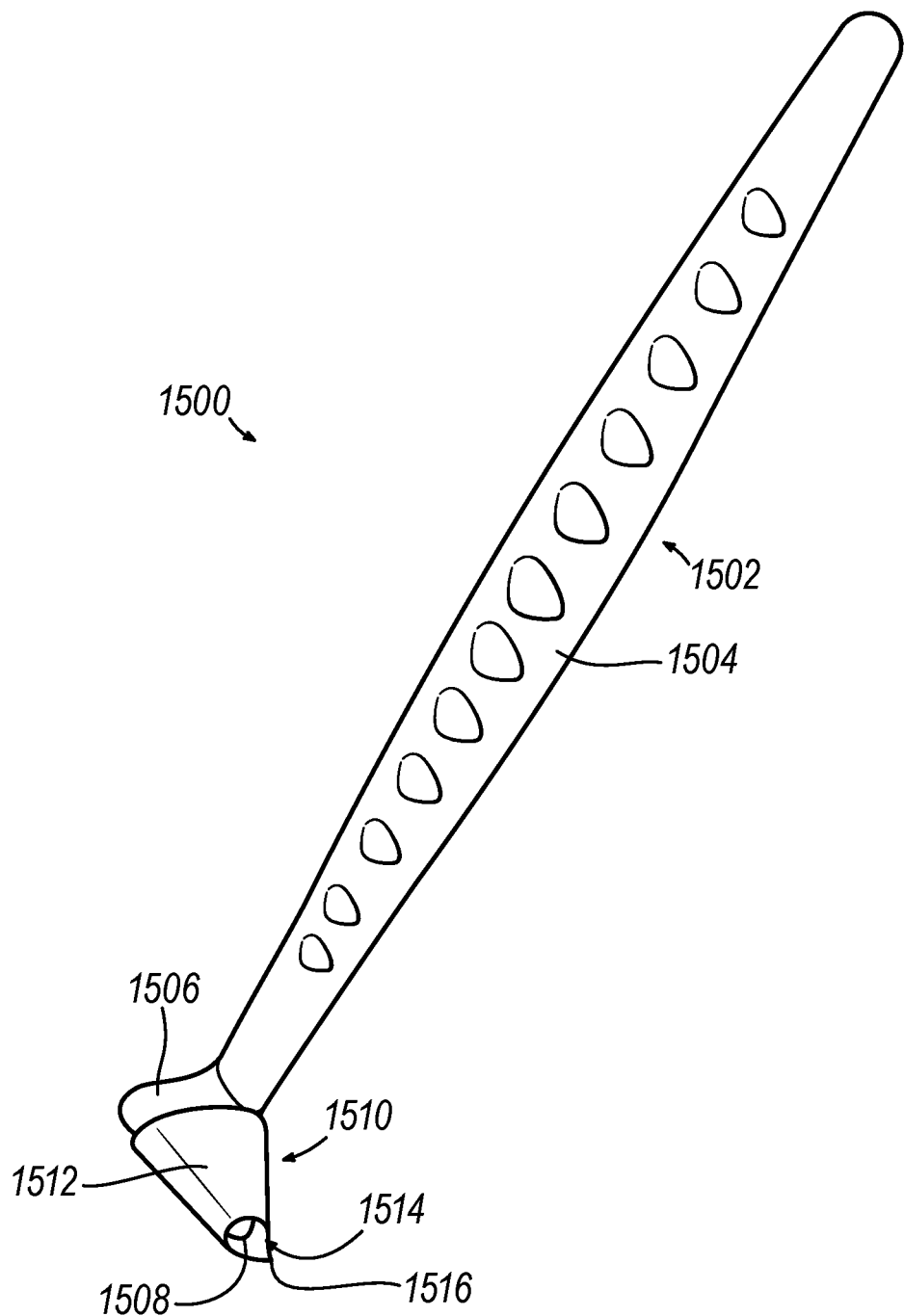
FIG. 40 depicts a perspective view of another example of a cannula guide assembly including a cannula guide and a guide deployer instrument.

As noted above, it may be desirable to provide a deployment instrument that facilitates an operator positioning a cannula guide in relation to a scleral incision (23). In some instances, it may also be desirable to allow for removal of the deployment instrument relative to the cannula guide after the cannula guide has been suitably positioned relative to the scleral incision (23), to thereby maximize access to, and visualization of, the cannula guide and the adjacent region of the eye (20). FIG. 40 shows an example of a cannula guide assembly (1500) that includes a deployment instrument (1502) and a cannula guide (1510), where deployment instrument (1502) may be used to facilitate positioning of cannula guide (1510), and where deployment instrument (1502) may be easily decoupled from cannula guide (1510) after cannula guide (1510) has been suitably positioned.

Deployment instrument (1502) of the present example includes an elongate shaft (1504) and a head (1506) at the distal end of shaft (1504). Shaft (1504) is configured for grasping by the operator. Head (1506) has a generally triangular or frustoconical shape that is configured to complement the interior region of cannula guide (1510). Cannula guide (1510) includes a body (1512) having a generally triangular or frustoconical shape. Cannula guide (1510) has a relatively narrow distal opening (1514) and a relatively wide proximal opening (1518), with a hollow interior region extending between openings (1514, 1516). Cannula guide (1510) of this example thus has a funnel-like configuration. A tongue (1516) projects distally from body (1512) at distal opening (1514).

Figure 41A:
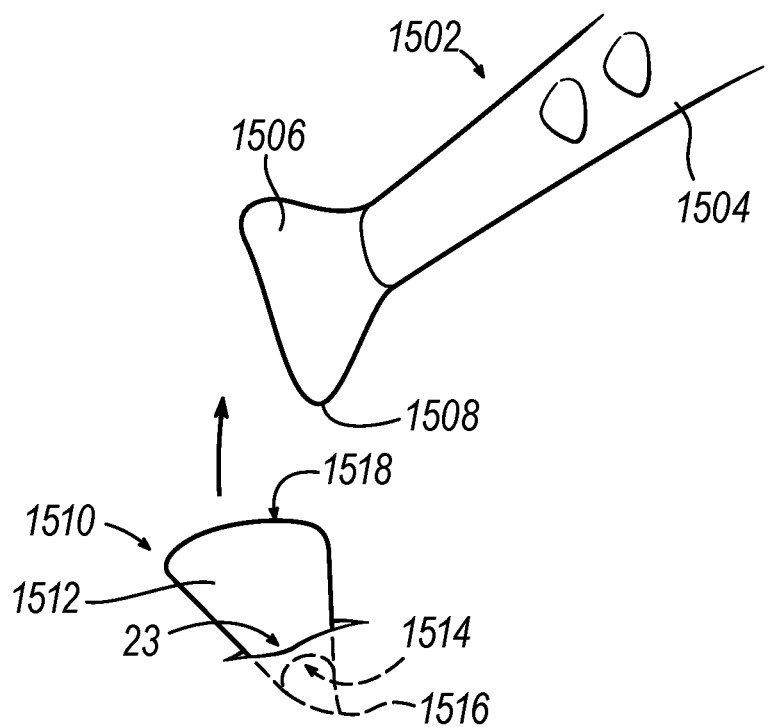
FIG. 41A depicts a perspective view of the cannula guide assembly of FIG. 40, with the guide deployer instrument having deployed the cannula guide in an eye of the patient.

In use, cannula guide (1510) may be fitted to deployment instrument (1502), with head (1506) positioned in the hollow interior region of body (1512) as shown in FIG. 40. In some versions, head (1506) and body (1512) are configured to provide a snug fit of cannula guide (1510) on head (1506). In addition, or in the alternative, head (1506) may include an elastomeric material or other material that provides a friction fit with body (1512), to thereby releasably retain cannula guide (1510) on head (1506). With cannula guide (1510) on head (1506) as shown in FIG. 40, the operator may grasp shaft (1504) of deployment instrument (1502) and position guiding portion cannula guide (1510) adjacent to a scleral incision (23). The operator may then manipulate deployment instrument (1502) to insert tongue (1516) and adjacent regions of the distal portion of cannula guide (1510) into the scleral incision (23). The insertion portion of cannula guide (1510) may be located within the suprachoroidal space, between the choroid (24) and the sclera (22). With cannula guide (1510) sufficiently inserted in the scleral incision (23), the operator may pull deployment instrument (1502) away from cannula guide (1510), leaving cannula guide (1510) disposed in the scleral incision (23) as shown in FIG. 41A. To the extent that a friction fit (or other kind of coupling) is used to removably secure cannula guide (1510) to head (1506) of deployment instrument (1502), friction between the eye (20) and cannula guide (1510) may overcome such retention to thereby maintain cannula guide (1510) in the eye (20) as deployment instrument (1502) is pulled away.

Figure 41B:
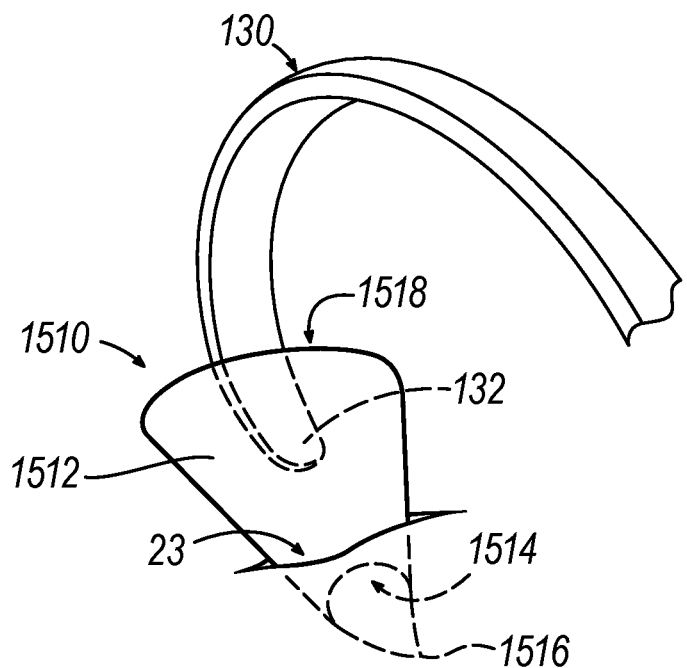
FIG. 41B depicts a perspective view of the cannula guide of FIG. 40, with the cannula guide guiding insertion of a cannula into an eye of a patient.

With cannula guide (1510) inserted in the scleral incision (23) as shown in FIG. 41A, the operator may then insert cannula (130) into proximal opening (1518) of cannula guide (1510), as shown in FIG. 41B. The funnel-like configuration of body (1512) guides cannula (130) toward distal opening (1514), such that cannula (130) eventually exits distal opening (1514) into the suprachoroidal space. Tongue (1516) may provide further guidance to cannula (130) as cannula (130) exits distal opening (1514), promoting a tangential trajectory of cannula (130) and further protecting the choroid (24) in the region where cannula (130) exits via distal opening (1514). When cannula (130) is disposed in the suprachoroidal space, the funnel-like configuration of cannula guide (1510) allows cannula (130) to slide along an insertion axis (IA); while also allowing the operator to adjust the orientation of cannula (130) to various insertion axes (IA) at various angles (θ) relative to a central axis (CA) of the incision (23).

Q. Cannula Guide with Opposing Anchoring and Grounding Features

As noted above, it may be desirable in some instances to provide a cannula guide that simultaneously engages an inner surface of the sclera (22) (i.e., in the suprachoroidal space) and an outer surface of the sclera (22). This may secure the position of the cannula guide relative to the eye (20) and further mechanically ground the cannula guide relative to the eye, enhancing stabilization of the cannula guide relative to the eye (20). This enhanced stabilization may reduce the likelihood of inadvertent movement of the cannula guide relative to the eye (20), which may be of particular concern during uses of the cannula guide where a cannula (130) is adjusted several times to various insertion axes (IA) at various angles (θ) relative to a central axis (CA) of a scleral incision (23). FIGS. 42-66 depict several additional examples of cannula guides (1550, 1600, 1650, 1700, 1750, 1800, 1850, 1900, 2000, 2100, 2200) that provide this enhanced anchoring and stabilization through simultaneous engagement of inner and outer surfaces of the sclera (22).

Figure 42:
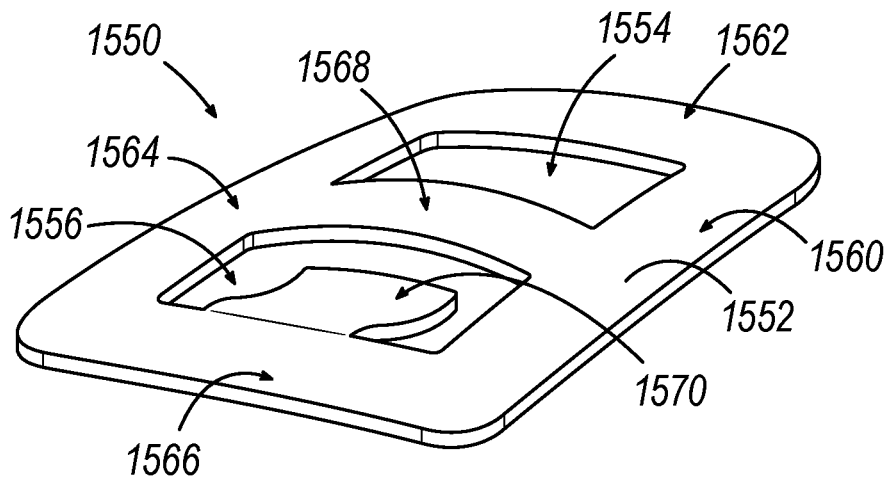
FIG. 42 depicts a perspective view of another example of a cannula guide.
Figure 43:
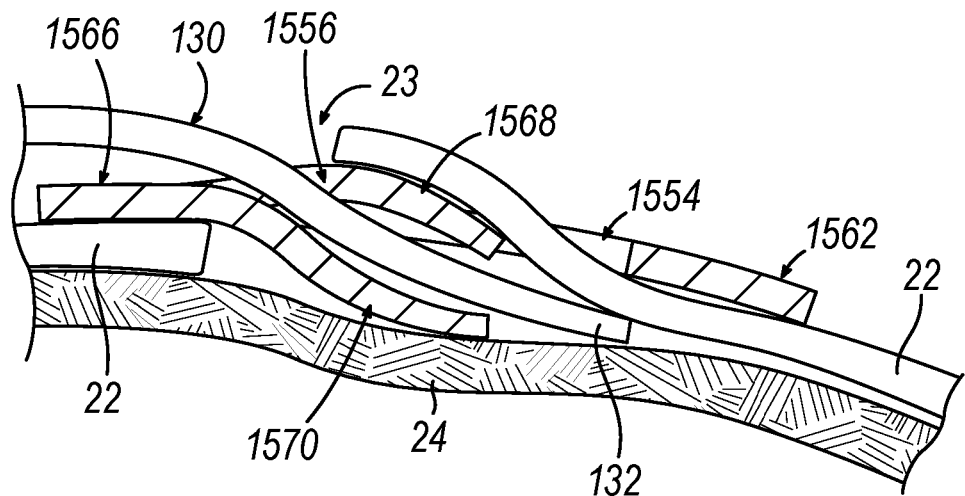
FIG. 43 depicts a cross-sectional view of the cannula guide of FIG. 42, with the cannula guide guiding insertion of a cannula into an eye of a patient.

FIGS. 42-43 show a cannula guide (1550) that includes a body (1552) with a first lateral portion (1560), a first end portion (1562), a second lateral portion (1564), and a second end portion (1566). In the present example, portions (1560, 1562, 1564, 1566) cooperate to define a rectangular shape, though portions (1560, 1562, 1564, 1566) may alternatively define any other suitable shape. Body (1552) also includes a cross-beam (1568) extending between lateral portions (1560, 1564). Cross-beam (1568) cooperates with portions (1560, 1562, 1564) to define a first opening (1554). Cross-beam (1568) cooperates with portions (1560, 1564, 1566) to define a second opening (1556). A tongue (1570) projects from second end portion (1566) into second opening (1556). In some versions, tongue (1570) projects downwardly and extends to a length such that a portion of tongue (1570) is positioned underneath cross-beam (1568). Body (1552) may be formed of a rigid material, a resilient material, or a combination of rigid and resilient materials. For instance, in some versions, portions (1560, 1562, 1564, 1566) and cross-beam (1568) are formed of a rigid material while tongue (1570) is formed of a resilient material.

FIG. 43 shows cannula guide (1550) installed on an eye (20). As shown, cannula guide (1550) is positioned such that tongue (1570) enters scleral incision (23); and cross-beam (1568) is positioned above scleral incision (23). Portions (1560, 1562, 1564, 1566) are indirectly engaged with the outer surface of the sclera (22) (via the conjunctiva). In some versions, tongue (1570) extends to a distance where tongue (1570) engages the inner surface of the sclera (22), such that portions (1560, 1562, 1564, 1566) and tongue (1570) cooperate to secure cannula guide (1550) to the eye (20) and stabilize cannula guide (1550) relative to the eye (20) by providing mechanical grounding against opposite surfaces of the sclera (22) simultaneously. As shown in FIG. 43, cannula (130) may be inserted into the scleral incision (23) by advancing along a space defined between tongue (1570) and cross-beam (1568). Tongue (1570) and cross-beam (1568) may cooperate to guide cannula (130) into the suprachoroidal space along a tangential path as shown in FIG. 43. Tongue (1570) may also protect the choroid (24) in the region near the scleral incision (23) as cannula (130) is initially inserted into the scleral incision (23). When cannula (130) is disposed in the suprachoroidal space, the configuration of second opening (1556) allows cannula (130) to slide along an insertion axis (IA); while also allowing the operator to adjust the orientation of cannula (130) to various insertion axes (IA) at various angles (θ) relative to a central axis (CA) of the incision (23).

Figure 44:
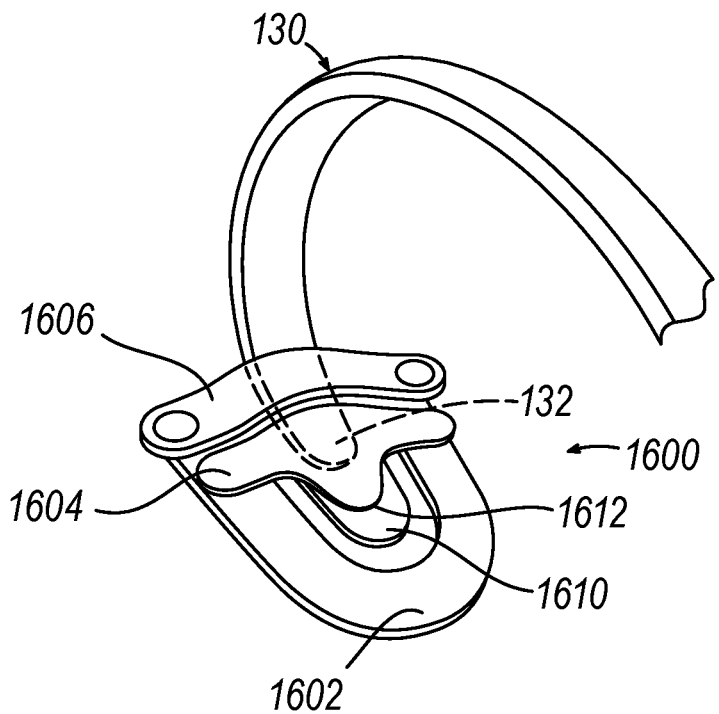
FIG. 44 depicts a perspective view of another example of a cannula guide, with a cannula positioned for insertion through the cannula guide.
Figure 45:
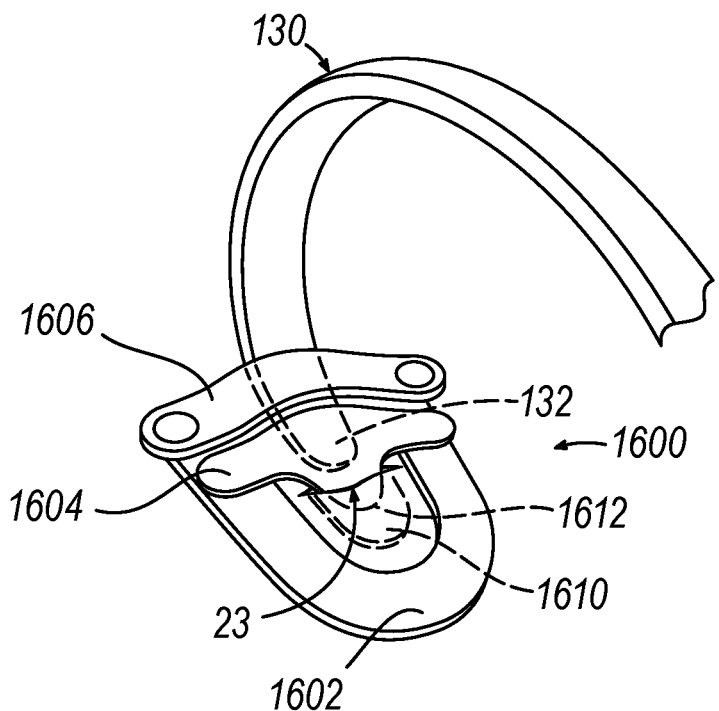
FIG. 45 depicts a perspective view of the cannula guide of FIG. 44, with the cannula guide guiding insertion of a cannula into an eye of a patient.

FIGS. 44-45 show another example of a cannula guide (1600). Cannula guide (1600) of this example includes a body (1602), a first strap (1604), and a second strap (1606). Body (1602) of this example has a U shape, with straps (1604, 1606) being secured to body (1602) near the free ends of this U shape. First strap (1604) defines an upper tongue (1612) and a lower tongue (1610), with tongues (1610, 1612) being positioned within the interior region defined by the U shape of body (1602). In the present example, lower tongue (1610) is longer than upper tongue (1612), though tongues (1610, 1612) may alternatively be of the same length or upper tongue (1612) may be longer than lower tongue (1610). In some versions, first strap (1604, 1606) is formed of a rigid or semi-rigid material while second strap (1606) is formed of an elastic material.

During use of cannula guide (1600), the operator may position cannula guide (1600) near a scleral incision (23) and insert both tongues (1601, 1612) into the incision (23) as shown in FIG. 45. At this stage, upper tongue (1612) may engage the inner surface of the sclera (22), lower tongue (1610) may engage the choroid (24), and body (1602) may indirectly engage the outer surface of the sclera (22) (via the conjunctiva). Upper tongue (1612) and body (1602) may thus cooperate to secure cannula guide (1600) to the eye (20) and stabilize cannula guide (1600) relative to the eye (20) by providing mechanical grounding against opposite surfaces of the sclera (22) simultaneously. The operator may then advance cannula (130) underneath straps (1604, 1606) into a space defined between tongues (1610, 1612). Second strap (1606) may assist in guiding cannula (130) into the space between tongues (1610, 1612). Tongues (1610, 1612) may cooperate to guide cannula (130) into the suprachoroidal space along a tangential path as shown in FIG. 43. Tongue (1612) may also protect the choroid (24) in the region near scleral incision (23) as cannula (130) is initially inserted into the scleral incision (23). When cannula (130) is disposed in the suprachoroidal space, the configuration of cannula guide (1600) allows cannula (130) to slide along an insertion axis (IA); while also allowing the operator to adjust the orientation of cannula (130) to various insertion axes (IA) at various angles (θ) relative to a central axis (CA) of the incision (23).

Figure 46:
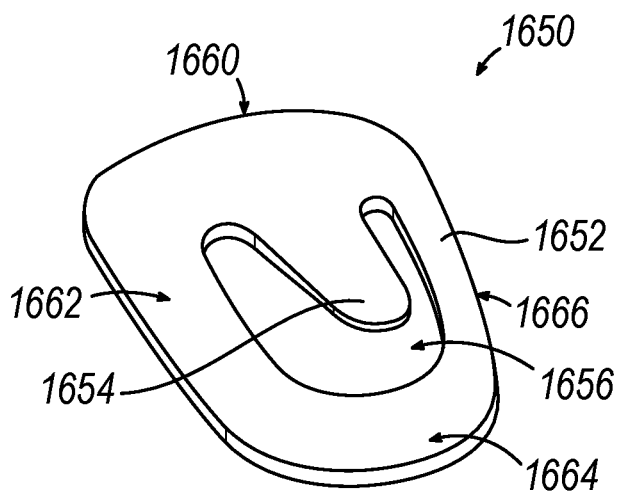
FIG. 46 depicts a perspective view of another example of a cannula guide.
Figure 47:
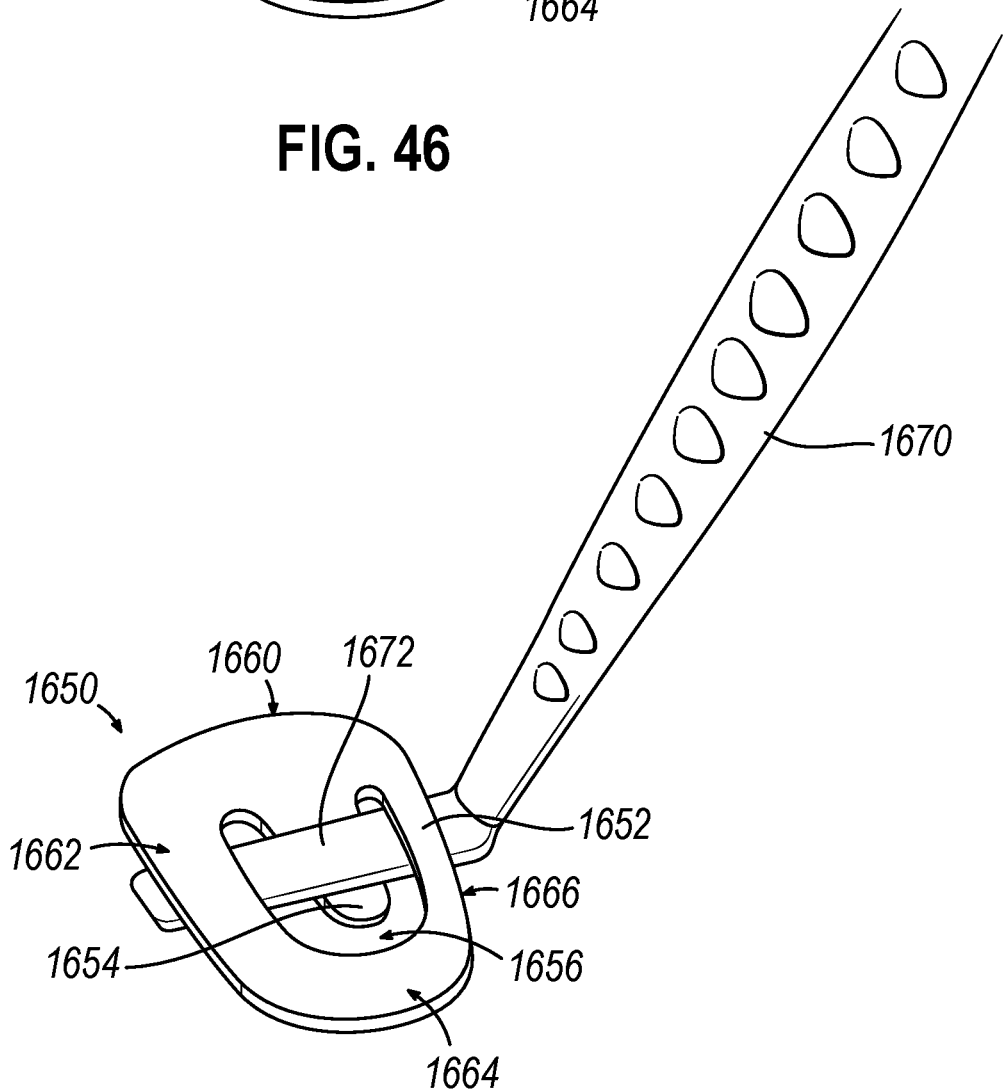
FIG. 47 depicts a perspective view of an example of a guide deployer instrument engaged with the cannula guide of FIG. 46.
Figure 48:
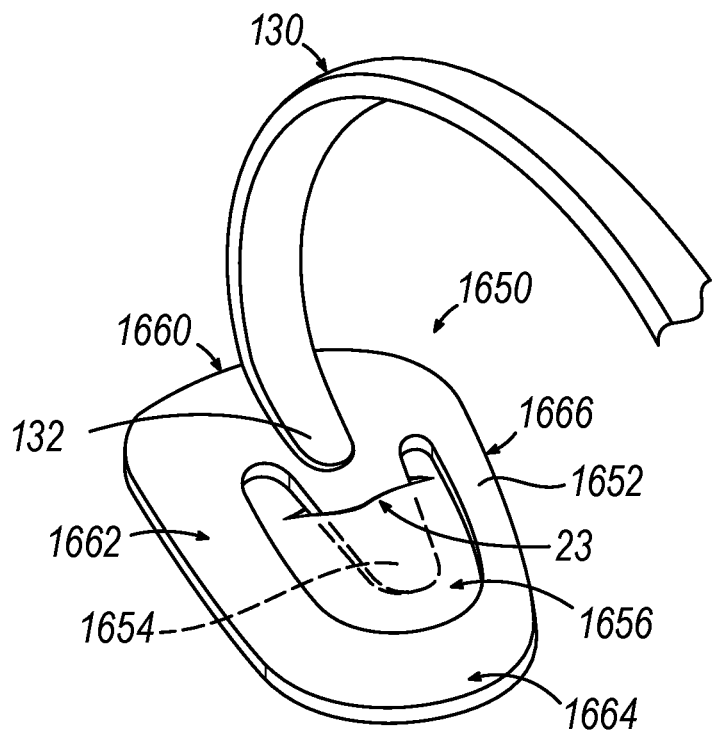
FIG. 48 depicts a perspective view of the cannula guide of FIG. 46, with the cannula guide guiding insertion of a cannula into an eye of a patient.

FIGS. 46-48 show another example of a cannula guide (1650). Cannula guide (1650) of this example includes a body (1652) with first end portion (1660), a first lateral portion (1662), a second end portion (1664), and a second lateral portion (1666). In the present example, portions (1660, 1662, 1664, 1666) cooperate to define a square shape, though portions (1660, 1662, 1664, 1666) may alternatively define any other suitable shape. Body (1652) also includes a tongue (1654) projecting from first end portion (1660) generally toward an interior space (1656) that is defined by portions (1660, 1662, 1664, 1666). In the present example, tongue (1654) is resiliently biased to extend obliquely upwardly away from a plane defined by portions (1660, 1662, 1664, 1666), as shown in FIG. 46. By way of example only, tongue (1654) may extend obliquely along a curve that arcs away from this plane of portions (1660, 1662, 1664, 1666); or tongue (1654) may extend along a straight path that is oriented obliquely from this plane of portions (1660, 1662, 1664, 1666). While tongue (1654) is resilient in the present example, the rest of body (1652) may be rigid.

As shown in FIG. 47, cannula guide (1650) may be engaged with a foot (1672) extending transversely from a shaft (1670) of a deployment instrument. In this configuration, foot (1672) may be simultaneously engaged with the upper surface of tongue (1654) and the lower surfaces of lateral portions (1662, 1666), such that foot (1672) maintains tongue (1654) in a stressed state. This may releasably secure cannula guide (1650) to foot (1672). With cannula guide (1650) so engaged, the operator may grasp shaft (1670) and thereby position cannula guide (1650) such that tongue (1654) enters a scleral incision (23). With at least a portion of the free end of tongue (1654) positioned in the scleral incision (23), the operator may then pull foot (1672) laterally away from cannula guide (1650). The inserted portion of tongue (1654) may maintain the position of cannula guide (1650) relative to the scleral incision (23) as foot (1672) is removed. Once cannula guide (1650) is free and clear of foot (1672), the operator may further urge cannula guide (1650) such that tongue (1654) fully enters the scleral incision (23) as shown in FIG. 48.

Once tongue (1654) is appropriately seated in the scleral incision (23), tongue (1654) engages the inner surface of the sclera (22) while body (1652) engages the outer surface of the sclera (22). Tongue (1654) and body (1652) thus cooperate to secure cannula guide (1650) to the eye (20) and stabilize cannula guide (1650) relative to the eye (20) by providing mechanical grounding against opposite surfaces of the sclera (22) simultaneously. This grip of cannula guide (1650) on the sclera (22) may be further enhanced by the resilient, upward bias of tongue (1654) on the lower surface of the sclera (22), which may further impart a counteracting downward force of body (1652) on the outer surface of the sclera (22). In some other variations, however, tongue (1654) does not have an oblique orientation or resilient upward bias, such that tongue (1654) is substantially coplanar with the rest of body (1652).

With cannula guide (1650) appropriately installed on the eye as shown in FIG. 48, the operator may advance cannula (130) into the scleral incision (23). In some instances, as shown in FIG. 48, cannula (130) may be advanced along the top surface of first end portion (1660) and tongue (1654) and into the scleral incision (23) to thereby reach the suprachoroidal space. In such instances, tongue (1654) may assist in guiding cannula (130) into the suprachoroidal space along a tangential path. Tongue (1654) may also protect the choroid (24) in the region near the scleral incision (23) as cannula (130) is initially inserted into the scleral incision (23). In some other instances, cannula (130) may be advanced along the bottom surface of first end portion (1660) and tongue (1654) and into the scleral incision (23) to thereby reach the suprachoroidal space. In such instances, tongue (1654) may still assist in guiding cannula (130) into the suprachoroidal space along a tangential path. Tongue (1654) may also protect the underside of the sclera (22) in the region near the scleral incision (23) as cannula (130) is initially inserted into the scleral incision (23). In either scenario, regardless of whether cannula (130) is advanced along the top surfaces or bottom surfaces of first end portion (1660) and tongue (1654), when cannula (130) is disposed in the suprachoroidal space, the configuration of cannula guide (1650) allows cannula (130) to slide along an insertion axis (IA); while also allowing the operator to adjust the orientation of cannula (130) to various insertion axes (IA) at various angles (θ) relative to a central axis (CA) of the incision (23).

Figure 49:
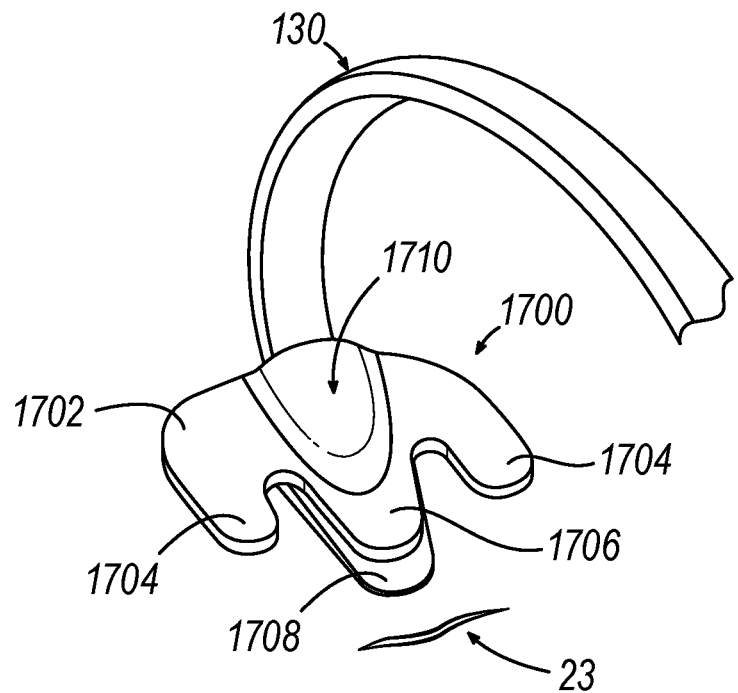
FIG. 49 depicts a perspective view of another example of a cannula guide, with a cannula positioned for insertion through the cannula guide, and with the cannula guide positioned for insertion into an incision formed in an eye of a patient.

FIG. 49 shows another example of a cannula guide (1700). Cannula guide (1700) of this example includes a body (1702), a pair of feet (1704), an upper tongue (1706), and a lower tongue (1708), with tongues (1610, 1612) being laterally interposed between feet (1704). In the present example, lower tongue (1708) is longer than upper tongue (1706), though tongues (1706, 1708) may alternatively be of the same length or upper tongue (1706) may be longer than lower tongue (1708). Body (1702) of the present example further defines a pocket (1710) that is configured to receive a distal portion of cannula (130) and thereby releasably retain cannula guide (1600) on cannula (130). Tongues (1706, 1708) may be resiliently biased to define a gap between tongues (1706, 1708) that is smaller than the thickness of cannula (130), such that tongues (1706, 1708) will provide at least slight resistance to advancement of cannula (130) through the space between tongues (1706, 1708). This may enable cannula guide (1600) to be carried on cannula (130) when cannula (130) is disposed in pocket (1710).

During use of cannula guide (1700), the operator may position cannula guide (1700) near a scleral incision (23) and insert both tongues (1706, 1708) into the incision (23). Cannula (130) may be already disposed in pocket (1710) during this positioning of cannula guide (1700). Once tongues (1706, 1708) have been inserted into the scleral incision (23), upper tongue (1706) may engage the inner surface of the sclera (22), lower tongue (1708) may engage the choroid (24), and feet (1704) may indirectly engage the outer surface of the sclera (22) (via the conjunctiva). Upper tongue (1706) and feet (1704) may thus cooperate to secure cannula guide (1700) to the eye (20) and stabilize cannula guide (1700) relative to the eye (20) by providing mechanical grounding against opposite surfaces of the sclera (22) simultaneously. The operator may then advance cannula (130) into the space defined between tongues (1706, 1708), and tongues (1706, 1708) may resiliently yield to cannula (130). Tongues (1706, 1708) may cooperate to guide cannula (130) into the suprachoroidal space along a tangential path. Tongue (1708) may also protect the choroid (24) in the region near scleral incision (23) as cannula (130) is initially inserted into the scleral incision (23); while tongue (1706) may protect the sclera (22) in the region near scleral incision (23) as cannula (130) is initially inserted into the scleral incision (23). When cannula (130) is disposed in the suprachoroidal space, the configuration of pocket (1710) and the rest of cannula guide (1700) allows cannula (130) to slide along an insertion axis (IA); while also allowing the operator to adjust the orientation of cannula (130) to various insertion axes (IA) at various angles (θ) relative to a central axis (CA) of the incision (23).

Figure 50:
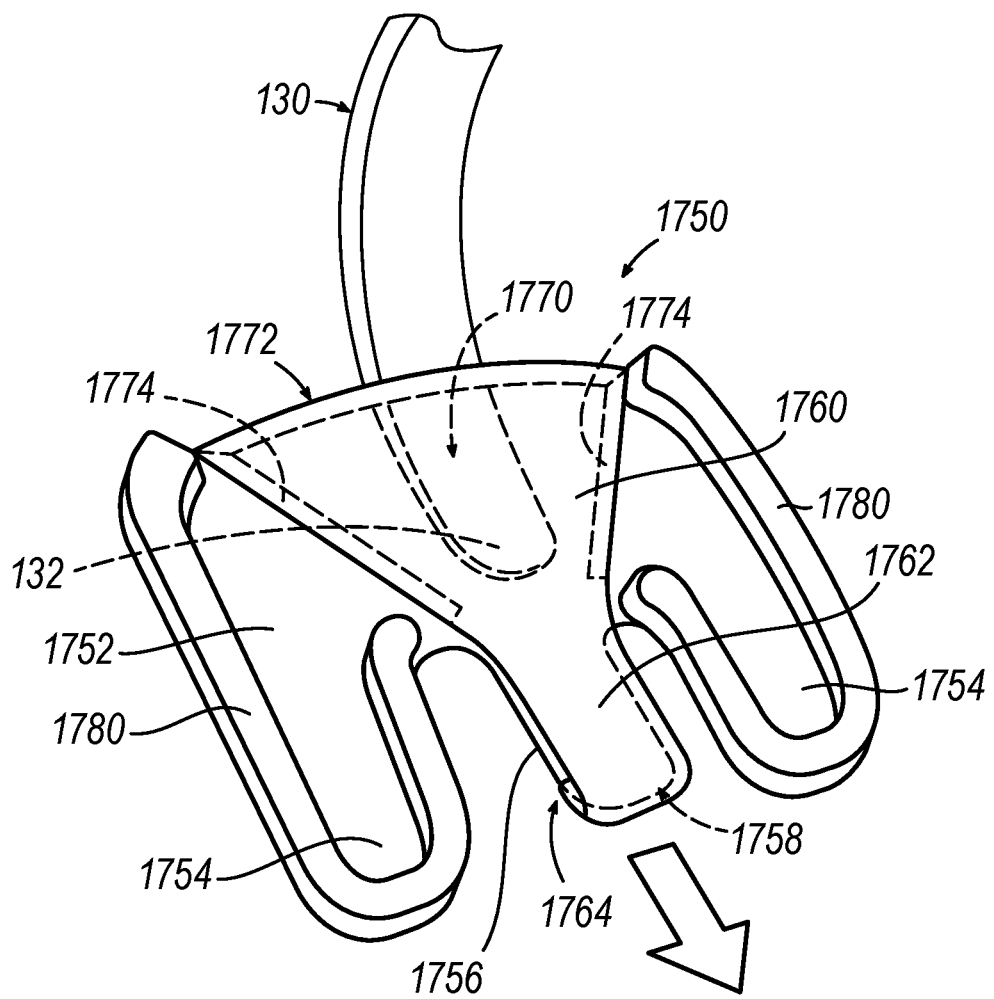
FIG. 50 depicts a perspective view of another example of a cannula guide.
Figure 51:
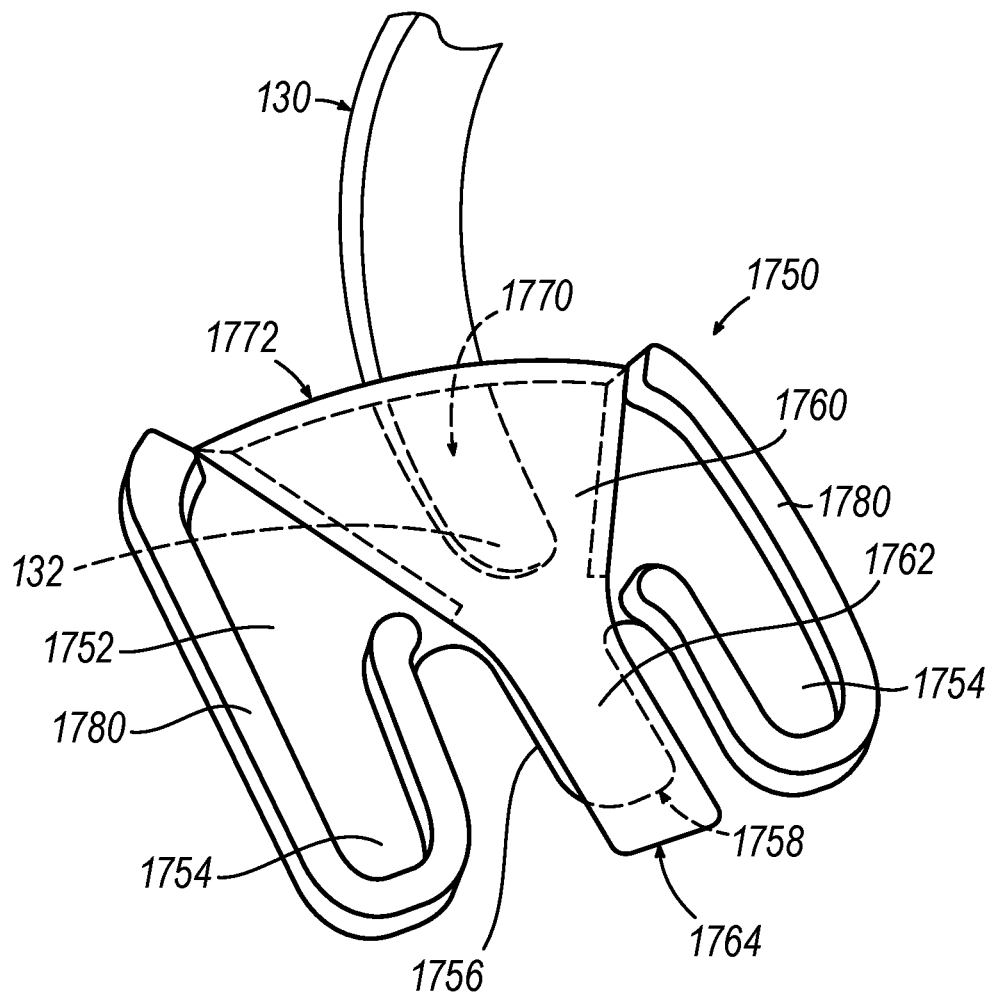
FIG. 51 depicts a perspective view of the cannula guide 50, with a cannula positioned for insertion through the cannula guide.

FIGS. 50-51 show another example of a cannula guide (1750). Cannula guide (1750) of this example includes a body (1752), a pair of feet (1754), and a tongue (1756), with tongue (1756) being laterally interposed between feet (1754). A film (1760) is secured over a V shaped recess (1770) that is formed in body (1752). In the present example, film (1760) is flexible yet inelastic. Some other versions of film (1760) may be elastic. Some versions of film (1760) are transparent to facilitate visualization of distal end (132) of cannula (130) being oriented relative to the incision (23) and then entering the incision (23), such that film (1760) may serve as a window member. Film (1760) of the present example includes a tongue portion (1762) that extends over tongue (1756), with a distal flap (1764) that is configured to wrap around distal end (1758) of tongue (1756) as shown in FIG. 50. Cannula guide (1750) of the present example further includes reinforcement ridges (1780) that are positioned along respective lateral edges of body (1752) and feet (1754). Reinforcement ridges (1780) are configured to provide additional rigidity to cannula guide (1750), though reinforcement ridges (1780) may be omitted in some variations.

As indicated above, recess (1770) has a V shape in this example. This V shape is defined in part by angled sidewalls (1774) that laterally bound recess (1770). Film (1760) and body (1762) cooperate to define a proximal opening (1772) at recess (1770), such that a cannula (130) may be inserted into recess (1770). As a cannula (130) is fed along recess (1770), angled sidewalls (1774) guide cannula (130) toward tongue (1756).

During use of cannula guide (1750), the operator may position cannula guide (1750) near a scleral incision (23) and insert tongue (1756) into the incision (23). During this insertion of tongue (1756) into the incision (23), distal flap (1764) may be wrapped around distal end (1758) of tongue (1756) as shown in FIG. 50. By way of example only, this arrangement may provide a single, rounded edge or surface to minimize snagging on the sclera (22) or choroid (24) during insertion of tongue (1756) into the incision (23). Once tongue (1756) has been inserted into the scleral incision (23), tongue (1756) may indirectly engage the inner surface of the sclera (22) via tongue portion (1762) of film (1760), tongue (1756) may directly engage the choroid (24), and feet (1754) may indirectly engage the outer surface of the sclera (22) (via the conjunctiva). Tongue (1756) and feet (1754) may thus cooperate to secure cannula guide (1750) to the eye (20) and stabilize cannula guide (1750) relative to the eye (20) by providing mechanical grounding against opposite surfaces of the sclera (22) simultaneously.

The operator may then advance cannula (130) into recess (1770) via proximal opening (1772) and ultimately into the space between tongue portion (1762) of film (1760) and tongue (1756). As the operator continues to advance cannula (130), cannula (130) may eventually drive flap (1764) to flip upwardly to the position shown in FIG. 51. Cannula (130) may then continue advancement into the suprachoroidal space. Tongue portion (1762) and tongue (1756) may cooperate to guide cannula (130) into the suprachoroidal space along a tangential path. Tongue (1756) may also protect the choroid (24) in the region near scleral incision (23) as cannula (130) is initially inserted into the scleral incision (23); while tongue portion (1762) may protect the sclera (22) in the region near scleral incision (23) as cannula (130) is initially inserted into the scleral incision (23). When cannula (130) is disposed in the suprachoroidal space, the configuration of recess (1770) allows cannula (130) to slide along an insertion axis (IA); while also allowing the operator to adjust the orientation of cannula (130) to various insertion axes (IA) at various angles (θ) relative to a central axis (CA) of the incision (23).

Figure 52:
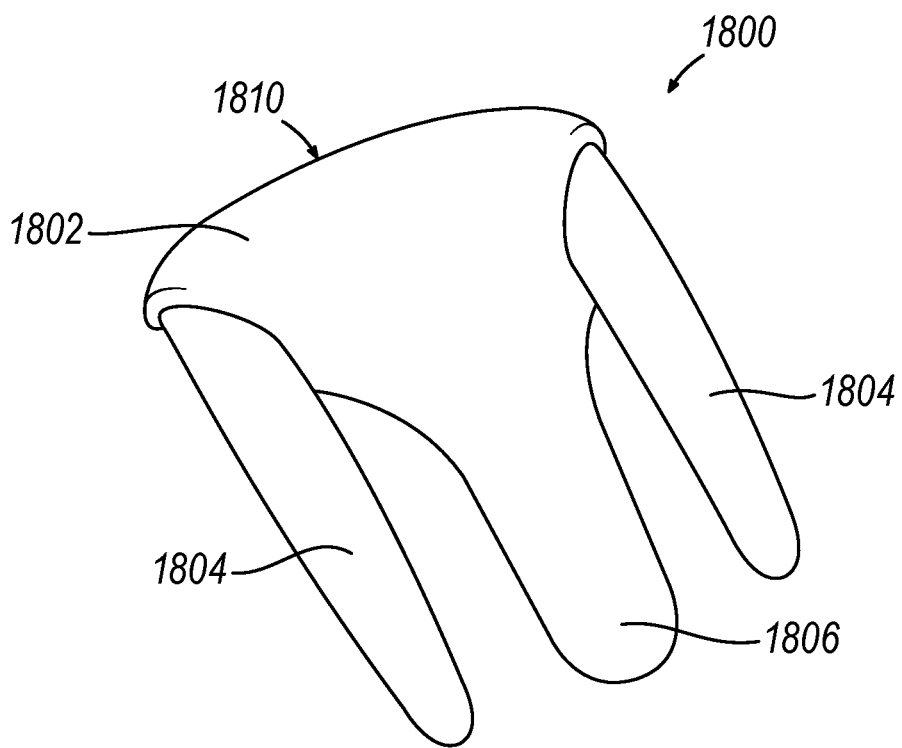
FIG. 52 depicts a perspective view of another example of a cannula guide.
Figure 53:
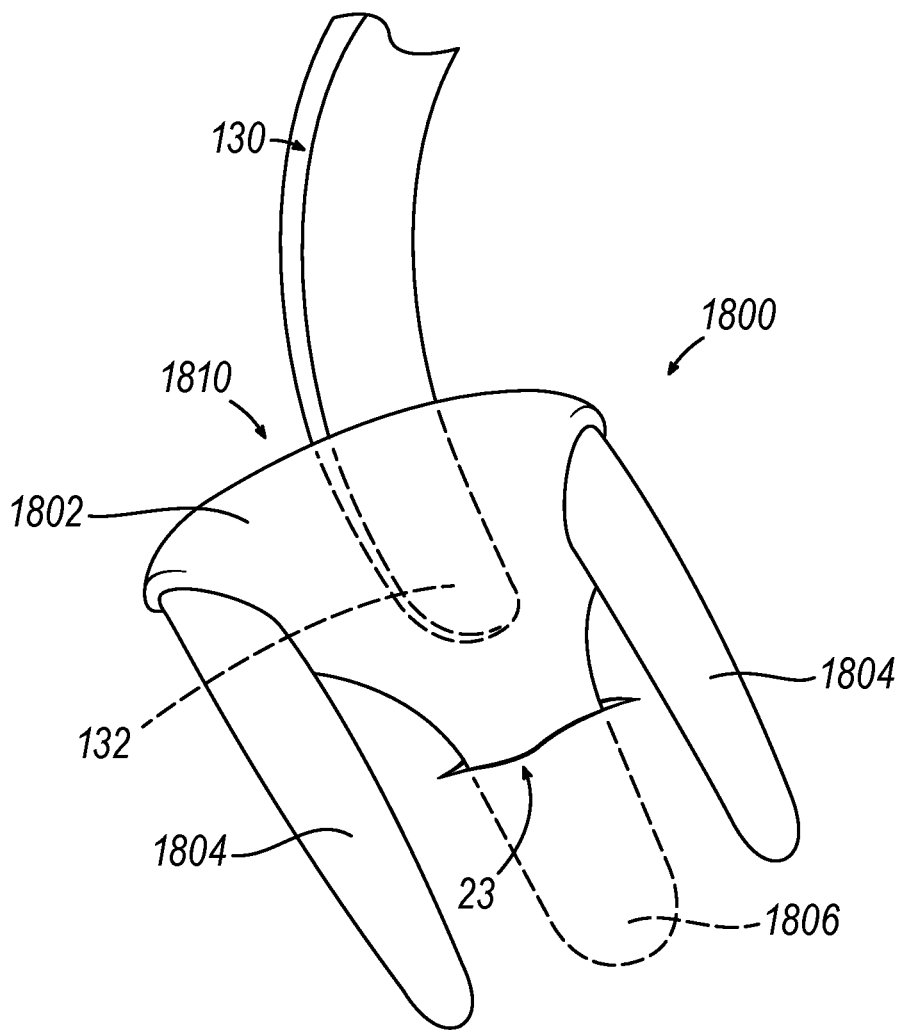
FIG. 53 depicts a perspective view of the cannula guide of FIG. 52, with the cannula guide guiding insertion of a cannula into an eye of a patient.
Figure 54:
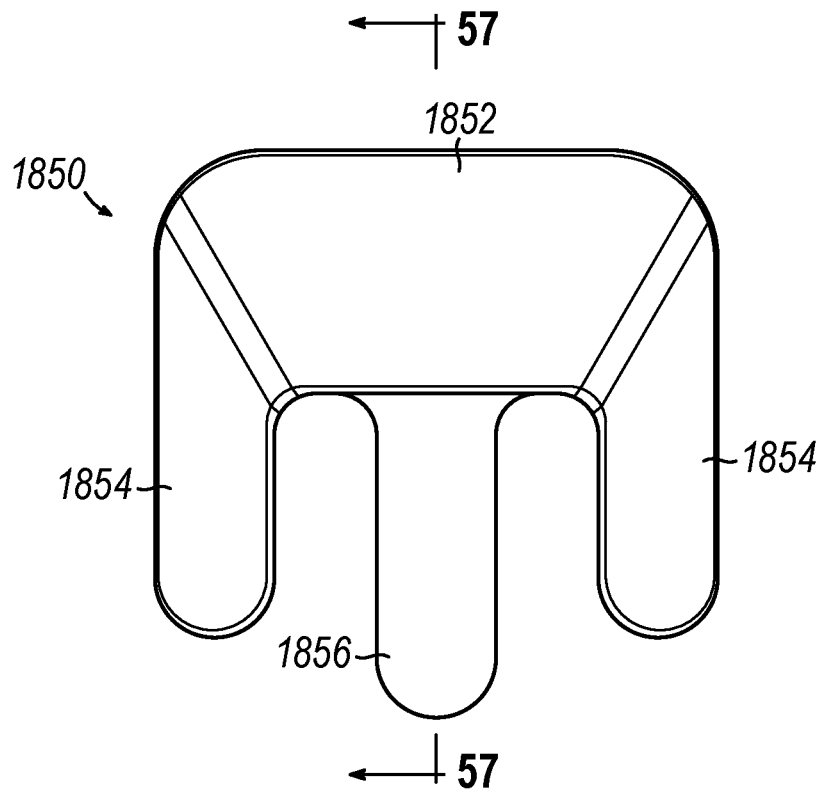
FIG. 54 depicts a top plan view of another example of a cannula guide.

FIGS. 52-53 show another example of a cannula guide (1800). Cannula guide (1800) of this example includes a body (1802), a pair of feet (1804), and a tongue (1806), with tongue (1806) being laterally interposed between feet (1804). Cannula guide (1800) further defines a proximal end (1810).

During use of cannula guide (1800), the operator may position cannula guide (1800) near a scleral incision (23) and insert tongue (1806) into the incision (23) as shown in FIG. 53. Once tongue (1806) has been inserted into the scleral incision (23), tongue (1806) may simultaneously engage the inner surface of the sclera (22) and the choroid (24); while feet (1804) may indirectly engage the outer surface of the sclera (22) (via the conjunctiva). Tongue (1806) and feet (1804) may thus cooperate to secure cannula guide (1800) to the eye (20) and stabilize cannula guide (1800) relative to the eye (20) by providing mechanical grounding against opposite surfaces of the sclera (22) simultaneously. The operator may then advance cannula (130) into a space formed between proximal end (180) and the sclera (22), continue advancing cannula (130) along a space formed between the rest of body (1802) and the sclera (22), until cannula (130) eventually enters incision (23) under tongue (1806). Cannula (130) may then continue advancement into the suprachoroidal space. Tongue (1806) may guide cannula (130) into the suprachoroidal space along a tangential path. Tongue (1806) may also protect the sclera (22) in the region near scleral incision (23) as cannula (130) is initially inserted into the scleral incision (23). When cannula (130) is disposed in the suprachoroidal space, the configuration of body (1802) allows cannula (130) to slide along an insertion axis (IA); while also allowing the operator to adjust the orientation of cannula (130) to various insertion axes (IA) at various angles (θ) relative to a central axis (CA) of the incision (23).

Figure 55:
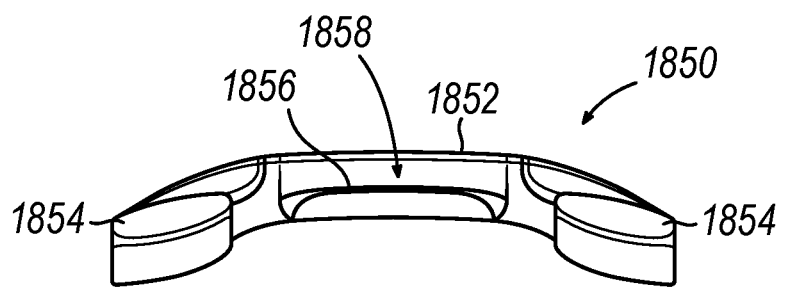
FIG. 55 depicts a front elevation view of the cannula guide of FIG. 54.
Figure 56:
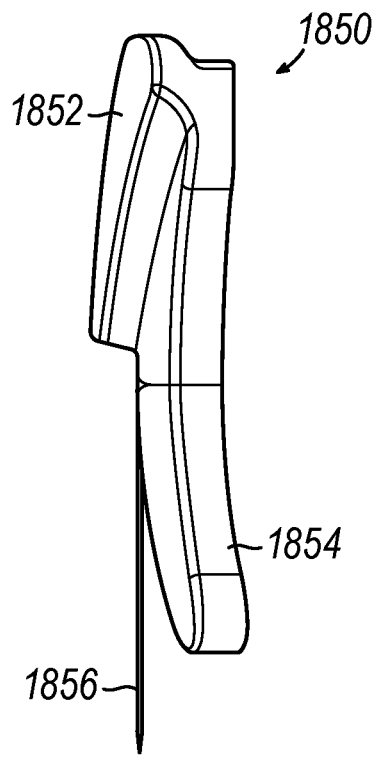
FIG. 56 depicts a side elevation view of the cannula guide of FIG. 54.
Figure 57:
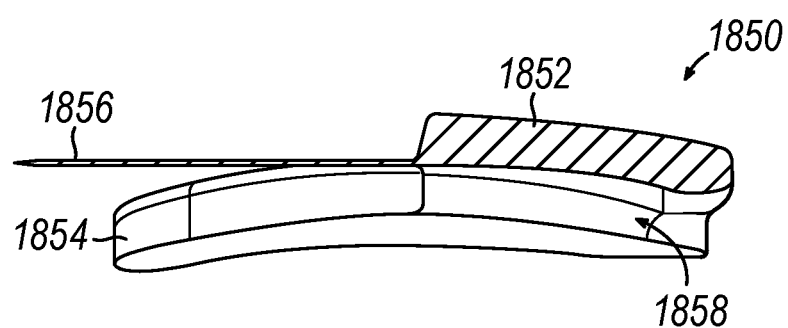
FIG. 57 depicts a cross-sectional view of the cannula guide of FIG. 54, taken along line 57-57 of FIG. 54.

FIGS. 54-57 show another example of a cannula guide (1850). Cannula guide (1850) of this example includes a body (1852), a pair of feet (1854), and a tongue (1856), with tongue (1856) being laterally interposed between feet (1854). Cannula guide (1850) further defines an inner passageway (1858) having a V shaped profile, leading toward tongue (1856). As best seen in FIGS. 55-57, body (1852) and feet (1854) extend along curves such that body (1852) and feet (1854) complement the curvature of the eye (20). It should be understood that any of the other various cannula guides described herein may also include features with curvatures complementing the curvature of the eye (20). In the present example, tongue (1856) does not extend along a curve; and instead has a straight configuration as best seen in FIGS. 56-57.

During use of cannula guide (1850), the operator may position cannula guide (1850) near a scleral incision (23) and insert tongue (1856) into the incision (23). Once tongue (1856) has been inserted into the scleral incision (23), tongue (1856) may engage the inner surface of the sclera (22); while feet (1854) may indirectly engage the outer surface of the sclera (22) (via the conjunctiva). Tongue (1856) and feet (1854) may thus cooperate to secure cannula guide (1850) to the eye (20) and stabilize cannula guide (1850) relative to the eye (20) by providing mechanical grounding against opposite surfaces of the sclera (22) simultaneously. The operator may then advance cannula (130) into through inner passageway (1858) of body (1852) and ultimately along tongue (1856). Cannula (130) may then continue advancement into the suprachoroidal space.

In some versions, inner passageway (1858) is configured to lead cannula (130) along the upper surface of tongue (1856), such that cannula (130) will be interposed between tongue (1856) and the inner surface of the sclera (22) after cannula (130) enters the incision (23). In some other versions, inner passageway (1858) is configured to lead cannula (130) along the lower surface of tongue (1856), such that cannula (130) will be interposed between tongue (1856) and the choroid (24) after cannula (130) enters the incision (23). In either case, tongue (1856) may guide cannula (130) into the suprachoroidal space along a tangential path. Tongue (1856) may also protect the choroid (24) or the sclera (22) in the region near scleral incision (23) as cannula (130) is initially inserted into the scleral incision (23), depending on whether inner passageway (1858) leads to the upper surface or lower surface of tongue (1856). When cannula (130) is disposed in the suprachoroidal space, the configuration of inner passageway (1858) allows cannula (130) to slide along an insertion axis (IA); while also allowing the operator to adjust the orientation of cannula (130) to various insertion axes (IA) at various angles (θ) relative to a central axis (CA) of the incision (23).

Figure 58:
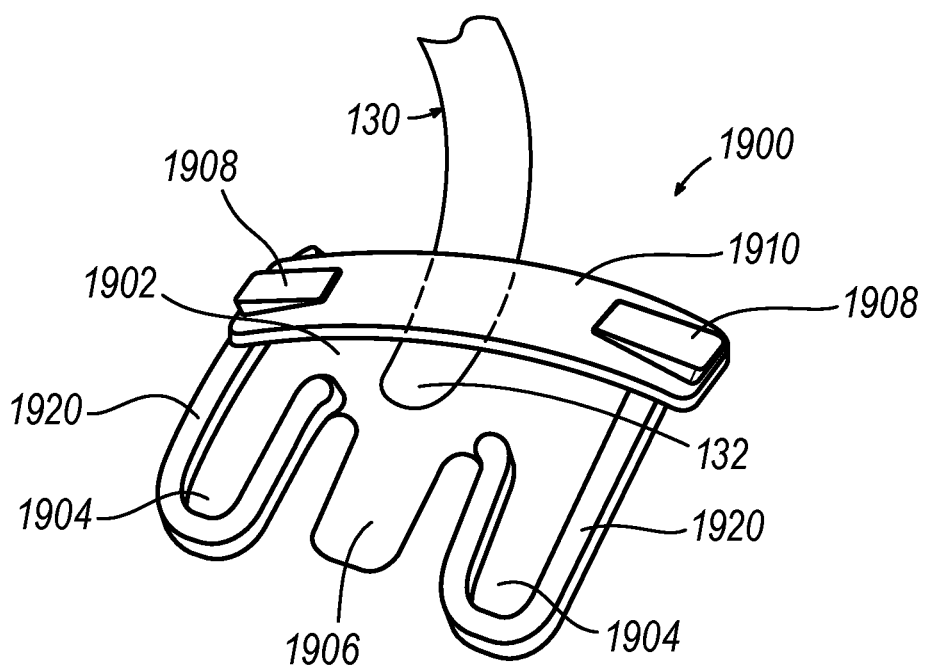
FIG. 58 depicts a perspective view of another example of a cannula guide, with a cannula positioned for insertion through the cannula guide.

FIG. 58 shows another example of a cannula guide (1900). Cannula guide (1900) of this example includes a body (1902), a pair of feet (1904), and a tongue (1906), with tongue (1906) being laterally interposed between feet (1904). A strap (1910) is secured to posts (1908) that are located at the proximal end of body (1902). In some versions, strap (1910) is elastic and is held in tension by posts (1908). In some other versions, strap (1910) is flexible yet inelastic. In either case, strap (1910) is configured to accommodate cannula (130) between strap (1910) and body (1902); while substantially retaining cannula (130) along the surface body (1902) as cannula (130) is advanced into the eye (20). Cannula guide (1900) of the present example further includes reinforcement ridges (1920) that are positioned along respective lateral edges of body (1902) and feet (1904). Reinforcement ridges (1920) are configured to provide additional rigidity to cannula guide (1900), though reinforcement ridges (1920) may be omitted in some variations.

During use of cannula guide (1900), the operator may position cannula guide (1900) near a scleral incision (23) and insert tongue (1906) into the incision (23). Once tongue (1906) has been inserted into the scleral incision (23), tongue (1906) may engage the inner surface of the sclera (22); while feet (1904) may indirectly engage the outer surface of the sclera (22) (via the conjunctiva). Tongue (1906) and feet (1904) may thus cooperate to secure cannula guide (1900) to the eye (20) and stabilize cannula guide (1900) relative to the eye (20) by providing mechanical grounding against opposite surfaces of the sclera (22) simultaneously. The operator may then advance cannula (130) through the space between strap (1910) and body (1902) and into the incision (23) along tongue (1906). Cannula (130) may then continue advancement into the suprachoroidal space. Tongue (1906) may to guide cannula (130) into the suprachoroidal space along a tangential path. Tongue (1906) may also protect the choroid (24) in the region near scleral incision (23) as cannula (130) is initially inserted into the scleral incision (23). When cannula (130) is disposed in the suprachoroidal space, the configuration of cannula guide (1900) allows cannula (130) to slide along an insertion axis (IA); while also allowing the operator to adjust the orientation of cannula (130) to various insertion axes (IA) at various angles (θ) relative to a central axis (CA) of the incision (23).

Figure 59:
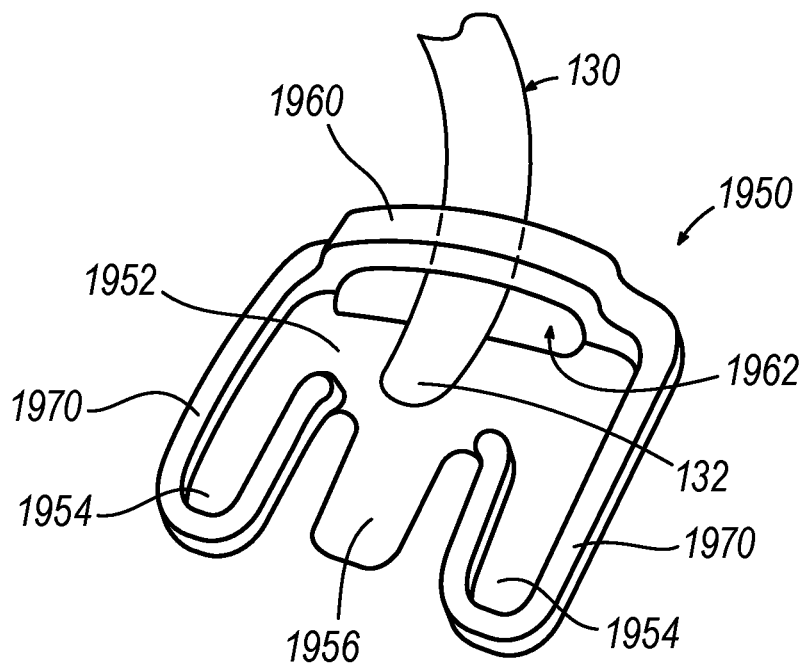
FIG. 59 depicts a perspective view of another example of a cannula guide, with a cannula positioned for insertion through the cannula guide.

FIG. 59 shows another example of a cannula guide (1950). Cannula guide (1950) of this example includes a body (1952), a pair of feet (1954), and a tongue (1956), with tongue (1956) being laterally interposed between feet (1954). A cross-beam (1960) located at the proximal end of body (1952) and cooperates with body (1952) to define a cannula insertion opening (1962). In some versions, cross-beam (1960) is rigid. Opening (1962) is configured to accommodate cannula (130) between cross-beam (1960) and body (1952); while cross-beam (1960) substantially retains cannula (130) along the surface body (1952) as cannula (130) is advanced into the eye (20). Cannula guide (1950) of the present example further includes reinforcement ridges (1970) that are positioned along respective lateral edges of body (1952) and feet (1954). Reinforcement ridges (1970) are configured to provide additional rigidity to cannula guide (1950), though reinforcement ridges (1970) may be omitted in some variations.

During use of cannula guide (1950), the operator may position cannula guide (1950) near a scleral incision (23) and insert tongue (1956) into the incision (23). Once tongue (1956) has been inserted into the scleral incision (23), tongue (1956) may engage the inner surface of the sclera (22); while feet (1954) may indirectly engage the outer surface of the sclera (22) (via the conjunctiva). Tongue (1956) and feet (1954) may thus cooperate to secure cannula guide (1950) to the eye (20) and stabilize cannula guide (1950) relative to the eye (20) by providing mechanical grounding against opposite surfaces of the sclera (22) simultaneously. The operator may then advance cannula (130) through opening (1962) and into the incision (23) along tongue (1956). Cannula (130) may then continue advancement into the suprachoroidal space. Tongue (1956) may to guide cannula (130) into the suprachoroidal space along a tangential path. Tongue (1956) may also protect the choroid (24) in the region near scleral incision (23) as cannula (130) is initially inserted into the scleral incision (23). When cannula (130) is disposed in the suprachoroidal space, the configuration of cannula guide (1950) allows cannula (130) to slide along an insertion axis (IA); while also allowing the operator to adjust the orientation of cannula (130) to various insertion axes (IA) at various angles (θ) relative to a central axis (CA) of the incision (23).

Figure 60:
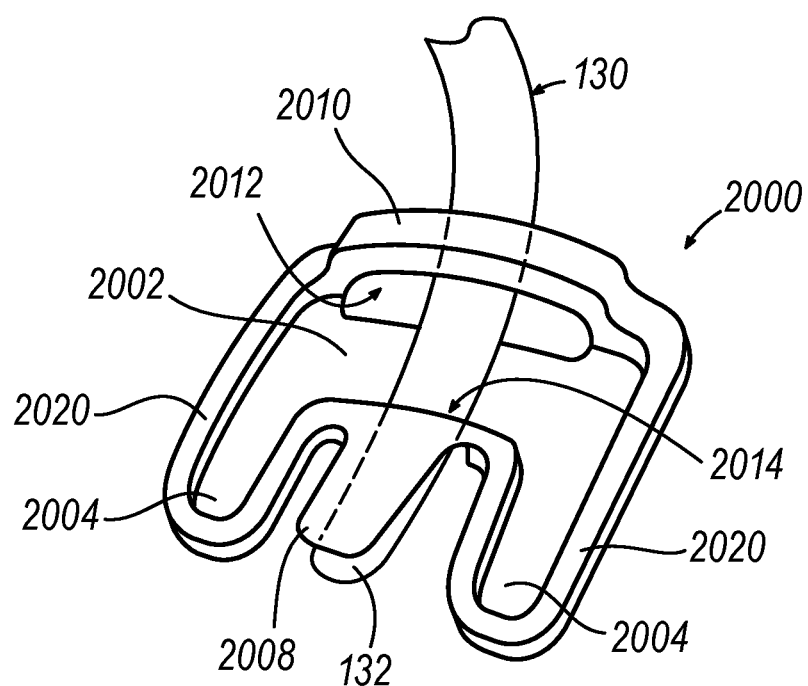
FIG. 60 depicts a perspective view of another example of a cannula guide, with a cannula positioned for insertion through the cannula guide.

FIG. 60 shows another example of a cannula guide (2000). Cannula guide (2000) of this example includes a body (2002), a pair of feet (2004), and a tongue (2006), with tongue (2006) being laterally interposed between feet (2004). A cross-beam (2010) located at the proximal end of body (2002) and cooperates with body (2002) to define a cannula insertion opening (2012). In some versions, cross-beam (2010) is rigid. Opening (2012) is configured to accommodate cannula (130) between cross-beam (2010) and body (2002); while cross-beam (2010) substantially retains cannula (130) along the surface body (2002) as cannula (130) is advanced into the eye (20). Cannula guide (2002) of the present example further includes reinforcement ridges (2020) that are positioned along respective lateral edges of body (2002) and feet (2004). Reinforcement ridges (2020) are configured to provide additional rigidity to cannula guide (2002), though reinforcement ridges (2020) may be omitted in some variations. Cannula guide (200) of the present example further includes a distal opening (2014). Distal opening (2014) is positioned at the proximal end of tongue (2008) and is configured to allow cannula (130) to pass underneath tongue (2008).

During use of cannula guide (2000), the operator may position cannula guide (2000) near a scleral incision (23) and insert tongue (2006) into the incision (23). Once tongue (2006) has been inserted into the scleral incision (23), tongue (2006) may engage the inner surface of the sclera (22); while feet (2004) may indirectly engage the outer surface of the sclera (22) (via the conjunctiva). Tongue (2006) and feet (2004) may thus cooperate to secure cannula guide (2000) to the eye (20) and stabilize cannula guide (2000) relative to the eye (20) by providing mechanical grounding against opposite surfaces of the sclera (22) simultaneously. The operator may then advance cannula (130) through openings (2012, 2014) and into the incision (23) along tongue (2008). Cannula (130) may then continue advancement into the suprachoroidal space. Tongue (2008) may to guide cannula (130) into the suprachoroidal space along a tangential path. Tongue (2008) may also protect the inner surface of the sclera (22) in the region near scleral incision (23) as cannula (130) is initially inserted into the scleral incision (23). When cannula (130) is disposed in the suprachoroidal space, the configuration of cannula guide (2000) allows cannula (130) to slide along an insertion axis (IA); while also allowing the operator to adjust the orientation of cannula (130) to various insertion axes (IA) at various angles (θ) relative to a central axis (CA) of the incision (23).

Figure 61:
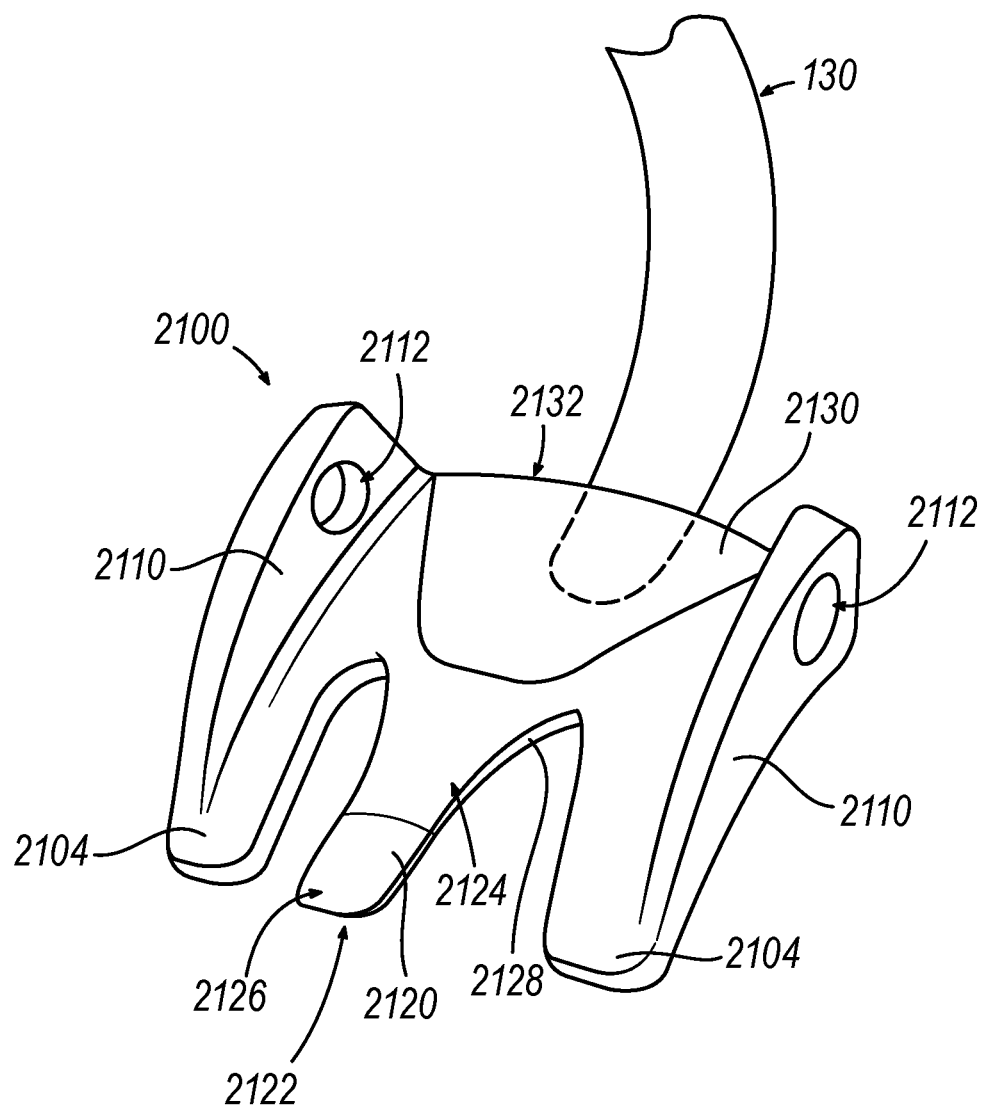
FIG. 61 depicts a perspective view of another example of a cannula guide, with a cannula positioned for insertion through the cannula guide.
Figure 62:
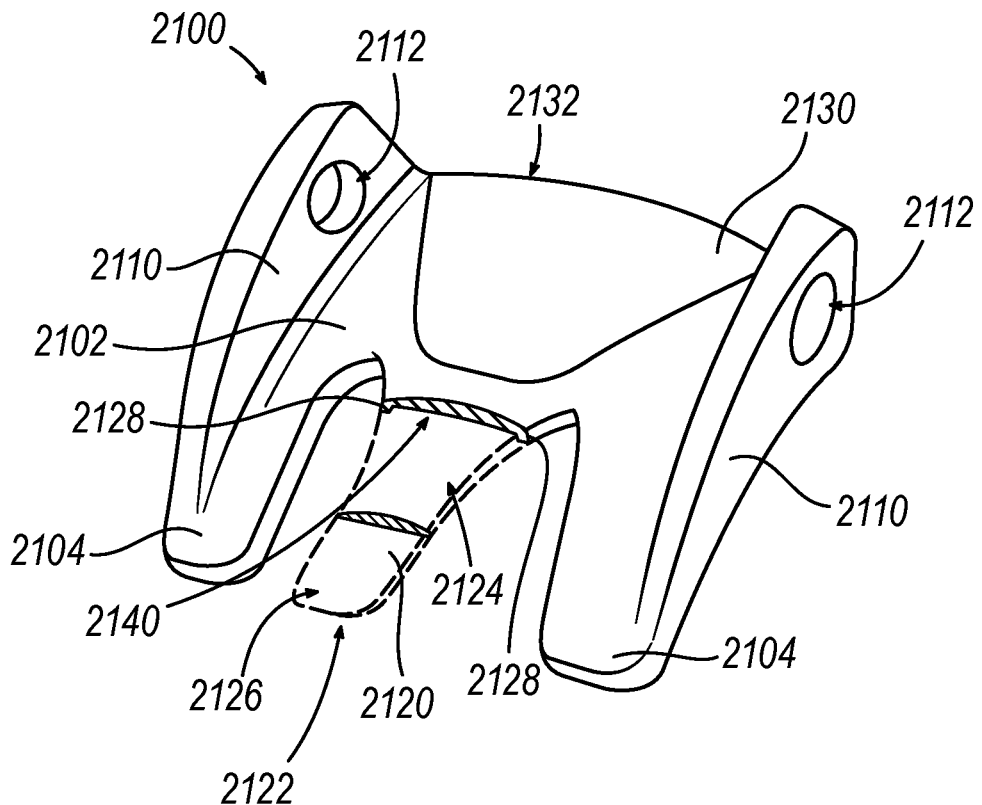
FIG. 62 depicts a schematic view of the cannula guide of FIG. 61, with cross-sectional regions of a tongue of the cannula guide emphasized.
Figure 63:
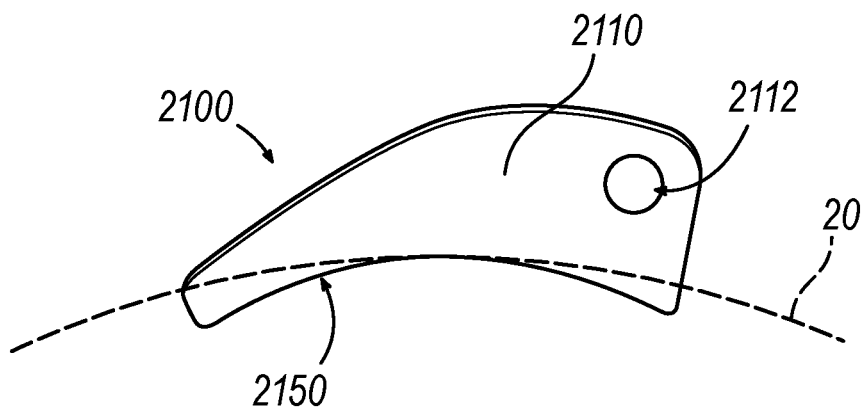
FIG. 63 depicts a side elevation view of the cannula guide of FIG. 61, with a schematic representation of an eye curvature shown in broken lines.

FIGS. 61-63 show another example of a cannula guide (2100). Cannula guide (2100) of this example includes a body (2102), a pair of feet (2104), and a tongue (2120), with tongue (2120) being laterally interposed between feet (2104). Cannula guide (2100) further includes a transparent window (2130) secured to body (2102), with window (2130) defining a proximal end (2132) of cannula guide (2100). Each foot (2104) includes a respective vertically-extending reinforcement rib (2110). Reinforcement ribs (2110) are configured to enhance the rigidity of feet (2104). Each reinforcement rib (2110) in this example defines an opening (2112). Openings (2112) are configured to receive corresponding pins, prongs, or other complementary features an applier instrument (not shown), such that the applier instrument may releasably retain cannula guide (2100) via reinforcement ribs (2110) for installation of cannula guide (2100) on an eye (20). Various other suitable features that may be used to removably couple cannula guide (2100) with an applier instrument, and various other suitable ways in which cannula guide (2100) may be installed on an eye (20), will be apparent to those skilled in the art in view of the teachings herein. Openings (2112) are thus optional.

Tongue (2120) of the present example includes a distal portion (2122) and a proximal portion (2124). Distal portion (2122) includes an upturned tip (2126), which extends obliquely relative to proximal portion (2124). This configuration of upturned tip (2126) may facilitate insertion of tongue (2120) into a scleral incision (23); and may assist in elevating the sclera (22) at the scleral incision (23) to further promote insertion of cannula (130) in the scleral incision (23). In some versions, upturned tip (2126) is substantially flat and extends obliquely relative to proximal portion (2124) along a straight path. In some other versions, upturned tip (2126) is curved and extends obliquely relative to proximal portion (2124) along a curved path. Upturned tip (2126) may also be tapered along a lateral dimension and/or along a vertical dimension, to further promote atraumatic insertion of upturned tip (2126) through the scleral incision (23).

Body (2102) and window (2130) are configured to define a gap (not shown) with the sclera (22) of the eye (20) when cannula guide (2100) is installed on the eye (20). This gap continues through proximal portion (2124) of tongue (2120). As best seen in FIG. 62, proximal portion (2124) of tongue (2120) includes sidewalls (2128) that define a passageway (2140) underneath tongue (2120). As cannula (130) is inserted along the gap (not shown) defined between the sclera (22) and the undersides of window (2130) and body (2102), cannula (130) may continue along the sclera (22) through passageway (2140) under tongue (2120). Sidewalls (2128) may assist in guiding the cannula (130) into the scleral incision (23) during this insertion. In addition, sidewalls (2128) may provide enhanced rigidity to proximal portion (2124) of tongue (2120).

As best seen in FIG. 63, the underside (2150) of cannula guide (2100) is contoured along a radius of curvature. In the present example, the radius of curvature of underside (2150) is smaller than the radius of curvature of the eye (20). While FIG. 63 shows a substantial difference between the radius of curvature of underside (2150) and the radius of curvature of the eye (20), this difference may be regarded as being exaggerated in FIG. 63 for purposes of illustration only. The difference between the radius of curvature of underside (2150) and the radius of curvature of the eye (20) may be smaller than the difference illustrated in FIG. 63. In any case, having a smaller radius of curvature on underside (2150) may promote a tighter, more secure fit between cannula guide (2100) and the eye (20) when cannula guide (2100) is installed on the eye (20). This may in turn provide greater stability in the position of cannula guide (2100) on the eye (20) as cannula (130) is being inserted into the scleral incision (23). While FIG. 63 shows the curvature of underside (2150) along the front-to-back dimension of cannula guide (2100), underside (2150) may have a similar curvature along the lateral dimension of cannula guide (2100).

During use of cannula guide (2100), the operator may position cannula guide (2100) near a scleral incision (23) and insert tongue (2120) into the incision (23) as described above. Once tongue (2120) has been inserted into the scleral incision (23), tongue (2120) may simultaneously engage the inner surface of the sclera (22) and the choroid (24); while feet (2104) may indirectly engage the outer surface of the sclera (22) (via the conjunctiva). Tongue (2120) and feet (2104) may thus cooperate to secure cannula guide (2100) to the eye (20) and stabilize cannula guide (2100) relative to the eye (20) by providing mechanical grounding against opposite surfaces of the sclera (22) simultaneously. The operator may then advance cannula (130) via proximal end (2132) into a space formed between window (2130) the sclera (22), observing this insertion through the transparency of window (2130); continue advancing cannula (130) along a space formed between (2102) and the sclera (22); and continue advancing cannula (130) under tongue (2120) via passageway (2140), until cannula (130) eventually enters incision (23) under tongue (2120). Cannula (130) may then continue advancement into the suprachoroidal space. Tongue (2120) may guide cannula (130) into the suprachoroidal space along a tangential path. Tongue (2120) may also protect the sclera (22) in the region near scleral incision (23) as cannula (130) is initially inserted into the scleral incision (23). When cannula (130) is disposed in the suprachoroidal space, the configuration of cannula guide (2100) allows cannula (130) to slide along an insertion axis (IA); while also allowing the operator to adjust the orientation of cannula (130) to various insertion axes (IA) at various angles (θ) relative to a central axis (CA) of the incision (23).

Figure 64:
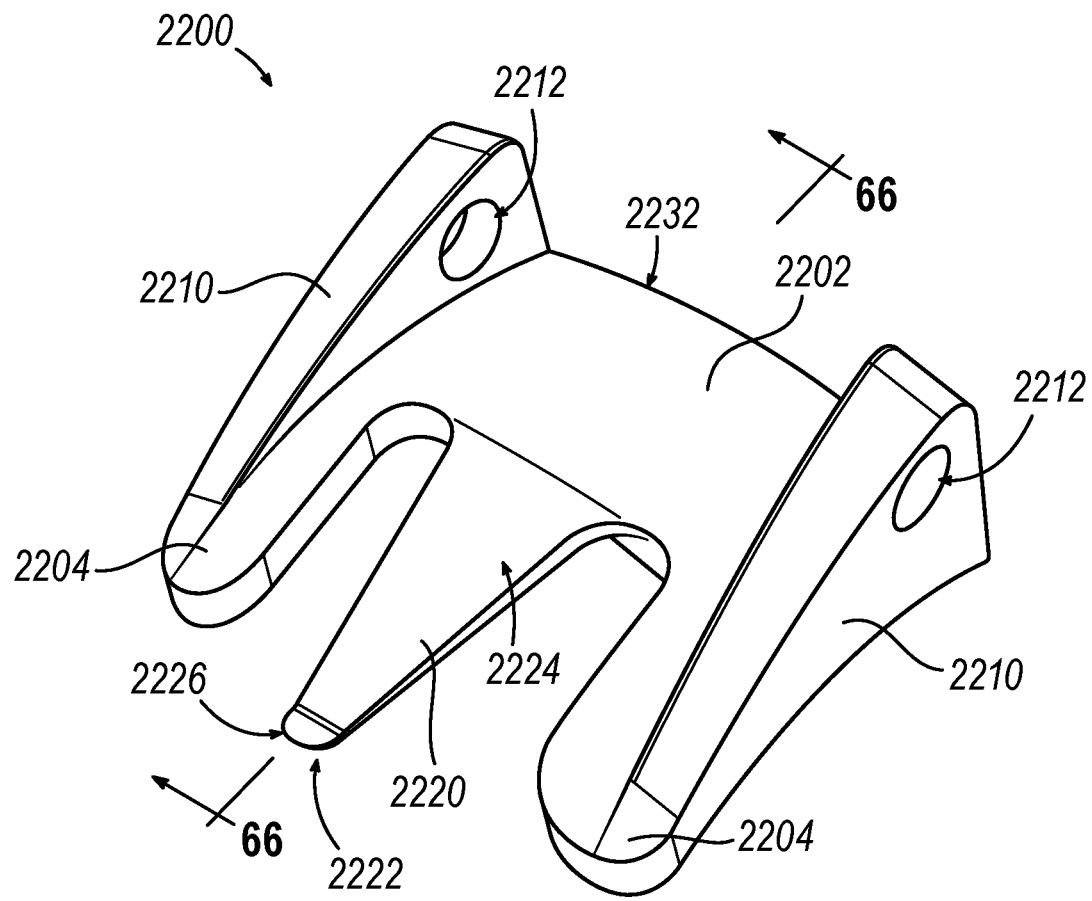
FIG. 64 depicts a perspective view of another example of a cannula guide.
Figure 65:
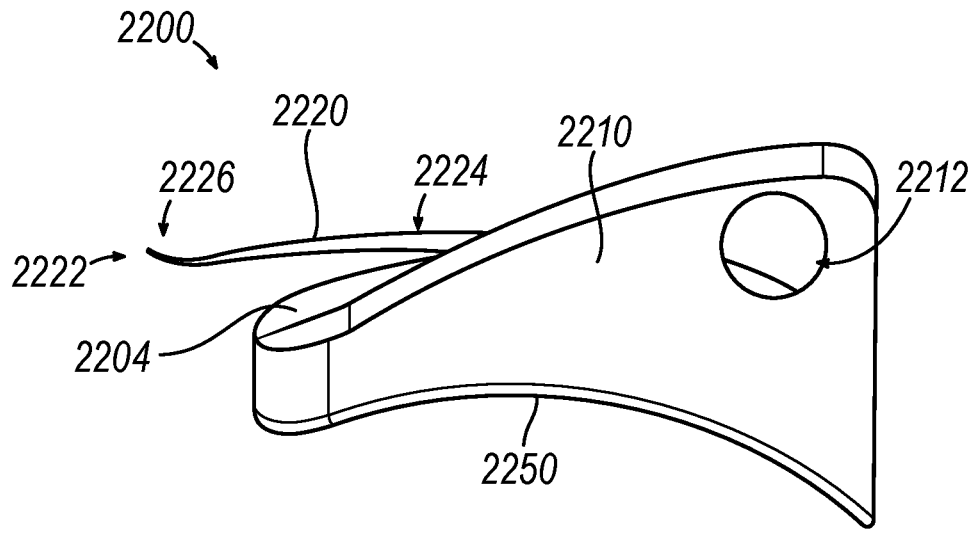
FIG. 65 depicts a side elevation view of the cannula guide of FIG. 64.
Figure 66:
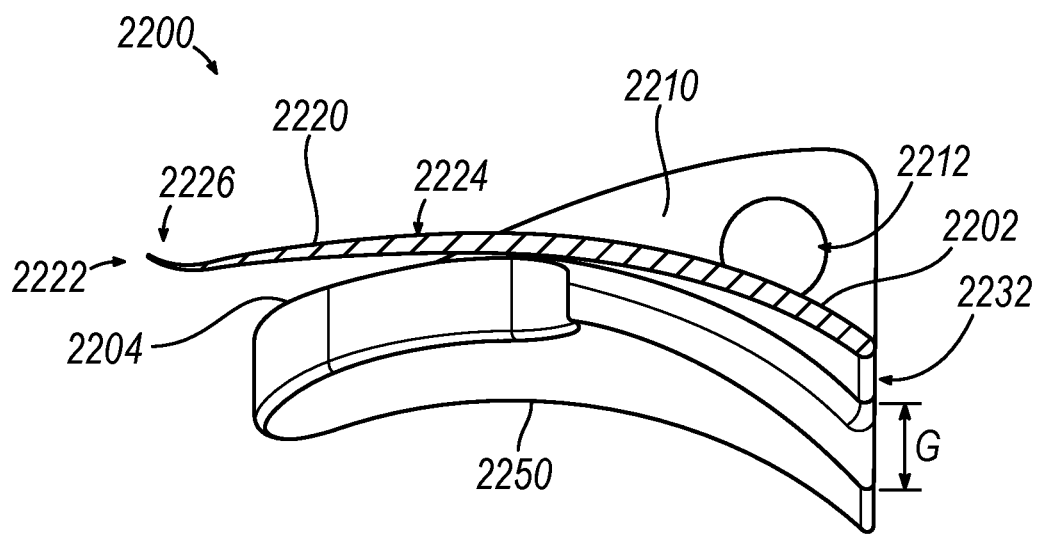
FIG. 66 depicts a cross-sectional view of the cannula guide of FIG. 64, taken along line 66-66 of FIG. 64.

FIGS. 64-66 show another example of a cannula guide (2200), which is substantially similar to cannula guide (2100) except for the differences noted below. Cannula guide (2200) of this example includes a body (2202), a pair of feet (2204), and a tongue (2220), with tongue (2220) being laterally interposed between feet (2204). Cannula guide (2200) of the present example lacks a transparent window. In some versions, body (2202) is formed of a transparent material such that the operator may readily visualize a cannula (130) interposed between body (2202) and a sclera (22). Each foot (2204) includes a respective vertically-extending reinforcement rib (2210). Reinforcement ribs (2210) are configured to enhance the rigidity of feet (2204). Each reinforcement rib (2210) in this example defines an opening (2212). Openings (2212) are configured to receive corresponding pins, prongs, or other complementary features an applier instrument (not shown), such that the applier instrument may releasably retain cannula guide (2200) via reinforcement ribs (2210) for installation of cannula guide (2200) on an eye (20). Various other suitable features that may be used to removably couple cannula guide (2200) with an applier instrument, and various other suitable ways in which cannula guide (2200) may be installed on an eye (20), will be apparent to those skilled in the art in view of the teachings herein. Openings (2212) are thus optional.

Tongue (2220) of the present example includes a distal portion (2222) and a proximal portion (2224). Distal portion (2222) includes an upturned tip (2226), which extends obliquely relative to proximal portion (2224). This configuration of upturned tip (2226) may facilitate insertion of tongue (2220) into a scleral incision (23); and may assist in elevating the sclera (22) at the scleral incision (23) to further promote insertion of cannula (130) in the scleral incision (23). In some versions, upturned tip (2226) is substantially flat and extends obliquely relative to proximal portion (2224) along a straight path. In some other versions, upturned tip (2226) is curved and extends obliquely relative to proximal portion (2224) along a curved path. Upturned tip (2226) may also be tapered along a lateral dimension and/or along a vertical dimension, to further promote atraumatic insertion of upturned tip (2126) through the scleral incision (23).

As shown in FIG. 66, body (2202) is configured to define a gap (G) with the sclera (22) of the eye (20) when cannula guide (2200) is installed on the eye (20). This gap (G) continues through proximal portion (2224) of tongue (2220). Unlike tongue (2120) of cannula guide (2100), tongue (2220) of cannula guide (2200) lacks sidewalls that define a passageway continuing from gap (G). Nevertheless, as cannula (130) is inserted along the gap (G) defined between the sclera (22) and the underside of body (2202), cannula (130) may continue along the sclera (22) under tongue (2220).

As best seen in FIGS. 65-66, the underside (2250) of cannula guide (2200) is contoured along a radius of curvature. FIG. 65 shows the curvature of underside (2250) along the front-to-back dimension of cannula guide (2100); while FIG. 66 shows the curvature of underside (2250) along the lateral dimension of cannula guide (2200). As with cannula guide (2100), the radius of curvature of underside (2250) of cannula guide (2200) may be smaller than the radius of curvature of the eye (20), to promote a tighter, more secure fit between cannula guide (2200) and the eye (20) when cannula guide (2200) is installed on the eye (20). This may in turn provide greater stability in the position of cannula guide (2200) on the eye (20) as cannula (130) is being inserted into the scleral incision (23).

During use of cannula guide (2200), the operator may position cannula guide (2200) near a scleral incision (23) and insert tongue (2220) into the incision (23) as described above. Once tongue (2220) has been inserted into the scleral incision (23), tongue (2220) may simultaneously engage the inner surface of the sclera (22) and the choroid (24); while feet (2204) may indirectly engage the outer surface of the sclera (22) (via the conjunctiva). Tongue (2220) and feet (2204) may thus cooperate to secure cannula guide (2200) to the eye (20) and stabilize cannula guide (2200) relative to the eye (20) by providing mechanical grounding against opposite surfaces of the sclera (22) simultaneously. The operator may then advance cannula (130) via proximal end (2232) into the gap (G) formed between body (2202) and the sclera (22), observing this insertion through the transparency of body (2202); and continue advancing cannula (130) under tongue (2220), until cannula (130) eventually enters incision (23) under tongue (2220). Cannula (130) may then continue advancement into the suprachoroidal space. Tongue (2220) may guide cannula (130) into the suprachoroidal space along a tangential path. Tongue (2220) may also protect the sclera

(22) in the region near scleral incision (23) as cannula (130) is initially inserted into the scleral incision (23). When cannula (130) is disposed in the suprachoroidal space, the configuration of cannula guide (2200) allows cannula (130) to slide along an insertion axis (IA); while also allowing the operator to adjust the orientation of cannula (130) to various insertion axes (IA) at various angles (θ) relative to a central axis (CA) of the incision (23).

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body sized and configured to be positioned on an eye of a patient; (b) an anchoring feature configured to secure the body to the eye of the patient; and (c) a guide feature configured to guide a cannula into a scleral incision formed in the eye of the patient along a path that is substantially tangential relative to the eye of the patient, the guide feature being sized and configured to allow the cannula to pivot laterally through a range of angular motion at the scleral incision.

Example 2

The apparatus of Example 1, the guide feature including a pair of rails, the rails cooperating to define a taper, the taper being configured to lead toward the scleral incision.

Example 3

The apparatus of any one or more of Examples 1 through 2, further comprising feet extending from the body.

Example 4

The apparatus of Example 3, the feet being configured to gather corresponding regions of a conjunctiva layer of the eye and thereby position the corresponding regions of the conjunctiva later away from the scleral incision.

Example 5

The apparatus of any one or more of Examples 3 through 4, the feet being configured to provide a mechanical ground against an outer region of a sclera layer of the eye.

Example 6

The apparatus of any one or more of Examples 1 through 5, the guide feature comprising a sliding member slidably coupled with the body, the sliding member being further configured to slidably receive the cannula.

Example 7

The apparatus of Example 6, the sliding member being configured to slide laterally relative to the body, along a dimension transversely oriented relative to a longitudinal axis defined by the cannula, to thereby allow the cannula to pivot laterally through the range of angular motion at the scleral incision.

Example 8

The apparatus of any one or more of Examples 1 through 7, the guide feature comprising one or more wire members secured to the body, the one or wire members being configured to define a cannula insertion region.

Example 9

The apparatus of Example 8, the one or more wire members including a first wire and a second wire, the second wire being shorter than the first wire such that the wires are arranged along a tapering profile.

Example 10

The apparatus of any one or more of Examples 1 through 9, the guide feature comprising a cross-beam secured to the body, the cross-beam being configured to define a cannula insertion region.

Example 11

The apparatus of any one or more of Examples 8 through 10, the cannula insertion region being configured to be parallel with an outer surface of the eye.

Example 12

The apparatus of any one or more of Examples 1 through 11, the anchoring feature comprising at least one tack.

Example 13

The apparatus of any one or more of Examples 1 through 12, the body being rotatable relative to the anchoring feature, the guide feature being rotatable with the body to thereby allow the cannula to pivot laterally through a range of angular motion at the scleral incision.

Example 14

The apparatus of Example 13, the body being rotatable relative to the anchoring feature about an axis that is substantially perpendicular to the outer surface of the eye.

Example 15

The apparatus of any one or more of Examples 1 through 14, further comprising a tongue, the tongue being sized and configured to enter the scleral incision.

Example 16

The apparatus of Example 15, the tongue being configured to define at least a portion of the guide feature, such that the tongue is configured to guide the cannula into a scleral incision formed in the eye of the patient along a path that is substantially tangential relative to the eye of the patient.

Example 17

The apparatus of Example 16, the tongue being configured to guide the cannula into a space between the tongue and an inner surface of a sclera layer of the eye.

Example 18

The apparatus of Example 16, the tongue being configured to guide the cannula into a space between the tongue and a choroid layer of the eye.

Example 19

The apparatus of any one or more of Examples 15 through 18, further comprising at least one foot, the foot and the tongue being configured to cooperatively define the anchoring feature.

Example 20

The apparatus of Example 19, the at least one foot being configured to provide a mechanical ground against an exterior region of the eye, the tongue being configured to provide a mechanical ground against an interior region of the eye.

Example 21

The apparatus of any one or more of Examples 19 through 20, the at least one foot including a first foot and a second foot, the tongue being laterally interposed between the first foot and the second foot.

Example 22

The apparatus of any one or more of Examples 1 through 21, the feature comprising a transparent window member, the transparent window member being configured to facilitate visualization of entry of a distal end of the cannula into the incision.

Example 23

The apparatus of any one or more of Examples 1 through 22, the body having an annular shape.

Example 24

The apparatus of any one or more of Examples 1 through 23, the body having an eye contacting surface contoured to complement a curvature of the eye.

Example 25

The apparatus of any one or more of Examples 1 through 24, the anchoring feature being configured to secure the body to the eye of the patient via suction.

Example 26

The apparatus of Example 25, the anchoring feature comprising one or more suction cups, the one or more suction cups being configured to engage the eye.

Example 27

The apparatus of any one or more of Examples 1 through 26, the anchoring feature comprising one or more traction features.

Example 28

The apparatus of Example 27, the one or more traction features being selected from the group consisting of microteeth, spikes, barbs, or hooks.

Example 29

The apparatus of any one or more of Examples 1 through 28, the anchoring feature comprising a securing leg, the securing leg including a sharp tip configured to pierce a sclera layer of the eye.

Example 30

The apparatus of Example 29, the securing leg being configured to slide relative to the body along an arcuate path.

Example 31

The apparatus of any one or more of Examples 29 through 30, the securing leg having an arcuate configuration.

Example 32

The apparatus of any one or more of Examples 29 through 31, the securing leg being configured to secure the body to the eye via a sclera layer of the eye without entering a vitreous region of the eye.

Example 33

The apparatus of Example 32, the securing leg being configured to secure the body to the eye via a sclera layer of the eye without penetrating a choroid layer of the eye.

Example 34

The apparatus of any one or more of Examples 29 through 33, the securing leg being pivotably coupled with the body.

Example 35

The apparatus of any one or more of Examples 29 through 34, the securing leg having a sharp tip and a region proximal to the sharp tip, the securing leg being configured to move relative to the body through a range of motion that includes the following stages: (i) entry of the sharp tip into a sclera layer of the eye, (ii) passage of the sharp tip and the region proximal to the sharp tip through the sclera layer of the eye, and (iii) exit of the sharp tip from the sclera layer of the eye while the region proximal to the sharp tip remains disposed in the sclera layer of the eye.

Example 36

The apparatus of any one or more of Examples 1 through 35, the body having an elongate shape with free ends, the free ends together defining the anchoring feature.

Example 37

The apparatus of Example 36, the free ends having tips configured to penetrate a choroid layer of the eye.

Example 38

The apparatus of any one or more of Examples 1 through 37, further comprising a resilient member, the resilient member being configured to maintain engagement between the anchoring feature and a sclera layer of the eye.

Example 39

The apparatus of Example 38, the anchoring feature including a pair of sharp features configured to penetrate the sclera layer of the eye, the resilient member being configured to bias the sharp features laterally in opposing directions.

Example 40

The apparatus of Example 39, the resilient member being configured to bias the sharp features outwardly away from each other.

Example 41

The apparatus of Example 39, the resilient member being configured to bias the sharp features inwardly toward each other.

Example 42

The apparatus of any one or more of Examples 38 through 41, the resilient member comprising a torsion spring.

Example 43

The apparatus of any one or more of Examples 38 through 42, the resilient member comprising an elastic elongate member, the elastic elongate member having a resilient bias extending along a length of the elastic elongate member.

Example 44

The apparatus of Example 43, the elastic elongate member forming the body.

Example 45

The apparatus of any one or more of Examples 43 through 44, the elastic elongate member comprising a strap.

Example 46

The apparatus of any one or more of Examples 1 through 45, further comprising a deployment instrument having a proximal end and a distal end, the body being removably coupled with the distal end of the deployment instrument.

Example 47

The apparatus of Example 46, the anchoring feature also being removably coupled with the distal end of the deployment instrument.

Example 48

The apparatus of Example 47, the deployment instrument including an actuator, the actuator being operable to drive the anchoring feature into the eye and thereby release the body and the anchoring feature from the distal end of the deployment instrument.

Example 49

The apparatus of any one or more of Examples 46 through 48, the body comprising a strap, the anchoring feature comprising a pair of tacks, the distal end of the deployment instrument being configured to hold the strap with the tacks disposed in the strap.

Example 50

The apparatus of any one or more of Examples 1 through 49, the body comprising a flexible elongate member having a first free end and a second free end, the anchoring feature comprising a first anchor and a second anchor, the first anchor being configured to anchor the first free end to the eye, the second anchor being configured to anchor the second free end to the eye, the flexible elongate member being configured to span across a portion of the eye while secured to the eye via the first and second anchors.

Example 51

The apparatus of Example 50, the flexible elongate member being elastic, the first and second anchors being configured to hold the flexible elongate member in tension while securing the flexible elongate member to the eye.

Example 52

The apparatus of any one or more of Examples 50 through 51, the flexible elongate member comprising a strap.

Example 53

The apparatus of any one or more of Examples 50 through 52, the first anchor comprising a first pin, the second anchor comprising a second pin.

Example 54

The apparatus of any one or more of Examples 50 through 52, the first anchor comprising a first suture, the second anchor comprising a second suture.

Example 55

The apparatus of any one or more of Examples 50 through 54, the guide feature being formed by an underside of the flexible elongate member, such that the flexible elongate member is configured to accommodate the cannula in a space between the eye and the underside of the flexible elongate member while the first and second anchors secure the flexible elongate member to the eye.

Example 56

The apparatus of any one or more of Examples 50 through 55, the first and second anchors each having a bent configuration and a sharp tip, the sharp tips of the first and second anchors being generally oriented toward each other.

Example 57

The apparatus of any one or more of Examples 1 through 56, further comprising a shaft extending integrally from the body, the shaft being configured for grasping by an operator to support the body.

Example 58

The apparatus of any one or more of Examples 1 through 57, the guide feature comprising a guide tab extending from the body, the guide tab being configured to guide the cannula to a space between the body and the eye.

Example 59

The apparatus of Example 58, the guide tab extending obliquely away from the body.

Example 60

The apparatus of Example 59, the guide tab having a curved configuration extending obliquely away from the body.

Example 61

The apparatus of any one or more of Examples 1 through 60, the body having a hollow interior, the hollow interior being configured to receive the cannula.

Example 62

The apparatus of Example 61, the body further defining a proximal opening and a distal opening, the proximal and distal openings being in communication with the hollow interior.

Example 63

The apparatus of Example 62, the proximal opening being larger than the distal opening.

Example 64

The apparatus of Example 63, the body further defining a taper extending from the proximal opening to the distal opening.

Example 65

The apparatus of any one or more of Examples 62 through 64, further comprising a tongue extending distally from the distal opening.

Example 66

The apparatus of Example 65, the tongue being configured to at least partially define the guide feature such that the tongue is configured to guide the cannula into a scleral incision formed in the eye of the patient along a path that is substantially tangential relative to the eye of the patient.

Example 67

The apparatus of any one or more of Examples 65 through 66, the tongue being further configured to at least partially define the anchoring feature such that the tongue is configured to secure the body to the eye.

Example 68

The apparatus of any one or more of Examples 1 through 67, further comprising an upper tongue and a lower tongue, the upper and lower tongues defining a space between the upper and lower tongues, the space between the upper and lower tongues being configured to receive the cannula.

Example 69

The apparatus of Example 68, the upper and lower tongues being configured for insertion into the scleral incision.

Example 70

The apparatus of Example 69, the upper tongue being configured to be interposed between the cannula and an inner surface of a sclera layer of the eye as the cannula is inserted in the scleral incision.

Example 71

The apparatus of any one or more of Examples 69 through 70, the lower tongue being configured to be interposed between the cannula and a choroid layer of the eye as the cannula is inserted in the scleral incision.

Example 72

The apparatus of any one or more of Examples 68 through 71, the lower tongue having a greater length than the upper tongue.

Example 73

The apparatus of any one or more of Examples 1 through 72, the body defining an opening, the apparatus further comprising a tongue extending from the body at the opening.

Example 74

The apparatus of Example 73, the body defining a plane, the tongue extending obliquely relative to the plane defined by the body.

Example 75

The apparatus of Example 74, the tongue being deflectable toward the opening, the tongue being resiliently biased to extend away from the opening.

Example 76

The apparatus of any one or more of Examples 1 through 75, the body defining a pocket, the pocket being configured to receive a distal end of the cannula and thereby enable the cannula to support the body.

Example 77

The apparatus of any one or more of Examples 1 through 76, further comprising: (a) a tongue projecting distally from the body, the tongue being sized and configured to enter the scleral incision, and (b) a film positioned over the tongue, the film and the tongue defining a space configured to receive the cannula.

Example 78

The apparatus of Example 77, the tongue having a distal end, the film defining a flap wrapped around the distal end of the tongue.

Example 79

The apparatus of any one or more of Examples 1 through 78, further comprising: (a) a tongue projecting distally from the body, the tongue being sized and configured to enter the scleral incision, and (b) a transverse member extending transversely across a proximal portion of the body, the transverse member and the body together defining an opening configured to receive the cannula.

Example 80

The apparatus of Example 79, the transverse member comprising a strap.

Example 81

The apparatus of Example 80, the strap being elastic.

Example 82

The apparatus of Example 79, the transverse member comprising a cross-beam.

Example 83

The apparatus of Example 82, the cross-beam being rigid.

Example 84

The apparatus of any one or more of Examples 79 through 83, the tongue and the transverse member being configured to cooperate to define the guide feature.

Example 85

The apparatus of any one or more of Examples 79 through 84, the guide feature being configured to guide the cannula to a space between the tongue and a sclera layer of the eye as the cannula is inserted into the scleral incision.

Example 86

The apparatus of any one or more of Examples 79 through 84, the guide feature being configured to guide the cannula to a space between the tongue and a choroid layer of the eye as the cannula is inserted into the scleral incision

V. MISCELLANEOUS

To the extent that several examples herein are described in the context of a cannula guide being positioned near an already-formed scleral incision (23), it should be understood that other kinds of procedures may be employed. For instance, in some variations of the procedures described herein, the cannula guide may be secured to the eye (20) first; and then the scleral incision (23) may be formed after the cannula guide has been secured to the eye (20). Other suitable steps and sequences that may be carried out in procedures that include a combination of a scleral incision (23) and a cannula guide will be apparent to those skilled in the art in view of the teachings herein.

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system, comprising:
   (a) an apparatus, comprising:
      (i) a body sized and configured to be positioned on an eye of a patient;
      (ii) an anchoring feature configured to secure the body to the eye of the patient;
      (iii) a guide feature configured to guide a cannula into a scleral incision formed in the eye of the patient along a path that is substantially tangential relative to the eye of the patient, the guide feature being sized and configured to allow the cannula to move within the guide feature and thereby pivot laterally relative to a central axis defined perpendicularly relative to the scleral incision through a range of angular motion at the scleral incision and within the guide feature; and
      (iv) feet extending from the body, the feet being configured to provide a mechanical ground against an outer region of a sclera layer of the eye; and
   (b) the cannula, wherein the cannula is sized and configured to move within the guide feature and thereby pivot laterally through the range of angular motion at the scleral incision.

2. The system of claim 1, the guide feature including a pair of rails, the rails cooperating to define a taper, the taper being configured to lead toward the scleral incision.

3. A system, comprising:
   (a) an apparatus, comprising:
      (i) A body sized and configured to be positioned on an eye of a patient;
      (ii) an anchoring feature configured to secure the body to the eye of the patient, the anchoring feature comprising at least one tack; and
      (iii) a guide feature configured to guide a cannula into a scleral incision formed in the eye of the patient along a path that is substantially tangential relative to the eye of the patient, the guide feature being sized and configured to allow the cannula to move within the guide feature and thereby pivot laterally relative to a central axis defined perpendicularly relative to the scleral incision through a range of angular motion at the scleral incision and within the guide feature; and
   (b) the cannula, wherein the cannula is sized and configured to move within the guide feature and thereby pivot laterally through the range of angular motion at the scleral incision.

4. An apparatus, comprising:
   (a) a body sized and configured to be positioned on an eye of a patient;
   (b) an anchoring feature configured to secure the body to the eye of the patient;
   (c) a guide feature configured to guide a cannula into a scleral incision formed in the eye of the patient along a path that is substantially tangential relative to the eye of the patient, the guide feature being sized and configured to allow the cannula to pivot laterally through a range of angular motion at the scleral incision; and
   (d) a tongue, the tongue being sized and configured to enter the scleral incision.

5. The apparatus of claim 4, the tongue being configured to define at least a portion of the guide feature, such that the tongue is configured to guide the cannula into a scleral incision formed in the eye of the patient along a path that is substantially tangential relative to the eye of the patient.

6. The system of claim 1, the body having an eye contacting surface contoured to complement a curvature of the eye.

7. The system of claim 1, the anchoring feature comprising a securing leg, the securing leg including a sharp tip configured to pierce a sclera layer of the eye, the securing leg being configured to slide relative to the body along an arcuate path.

8. The system of claim 7, the securing leg having a sharp tip and a region proximal to the sharp tip, the securing leg being configured to move relative to the body through a range of motion that includes the following stages:
   (i) entry of the sharp tip into a sclera layer of the eye,
   (ii) passage of the sharp tip and the region proximal to the sharp tip through the sclera layer of the eye, and
   (iii) exit of the sharp tip from the sclera layer of the eye while the region proximal to the sharp tip remains disposed in the sclera layer of the eye.

9. The system of claim 1, further comprising a resilient member, the resilient member being configured to maintain engagement between the anchoring feature and a sclera layer of the eye.

10. The system of claim 1, the guide feature comprising a guide tab extending from the body, the guide tab being configured to guide the cannula to a space between the body and the eye.

11. The system of claim 1, the body having a hollow interior, the hollow interior being configured to receive the cannula.

12. The system of claim 11, the body further defining a proximal opening and a distal opening, the proximal and distal openings being in communication with the hollow interior, the proximal opening being larger than the distal opening, the body further defining a taper extending from the proximal opening to the distal opening.

13. The system of claim 1, further comprising an upper tongue and a lower tongue, the upper and lower tongues defining a space between the upper and lower tongues, the space between the upper and lower tongues being configured to receive the cannula.

14. The system of claim 13, the upper and lower tongues being configured for insertion into the scleral incision.

15. The system of claim 13, the lower tongue having a greater length than the upper tongue.

16. The system of claim 1, further comprising:
   (a) a tongue projecting distally from the body, the tongue being sized and configured to enter the scleral incision, and
   (b) a transverse member extending transversely across a proximal portion of the body, the transverse member and the body together defining an opening configured to receive the cannula.

17. A system, comprising:
   (a) an apparatus, comprising:
      (i) a body sized and configured to be positioned on an eye of a patient; and
      (ii) a pair of rigid legs configured to secure the body to the eye of the patient, wherein each leg of the pair of legs has a sharp tip,
      wherein the body defines a cannula insertion region configured to guide a cannula into a scleral incision formed in the eye of the patient along a path that is substantially tangential relative to the eye of the patient, the cannula insertion region being sized and configured to allow the cannula to move within the cannula insertion region and thereby pivot laterally through a range of angular motion at the scleral incision and within the cannula insertion region for positioning a distal end of the cannula at a plurality of adjacent delivery sites within the eye of the patient; and
   (b) the cannula, wherein the cannula is sized and configured to move within the cannula insertion region and thereby pivot laterally through the range of angular motion at the scleral incision.

18. The system of claim 1, wherein the range of angular motion is up to approximately 20 degrees or up to approximately 80 degrees.

19. The system of claim 1, wherein the body is rigid.

* * * * *